(12) United States Patent
Bastiaans et al.

(10) Patent No.: US 7,569,516 B2
(45) Date of Patent: Aug. 4, 2009

(54) PLANT GROWTH REGULATION

(75) Inventors: Henricus Bastiaans, Usingen (DE); Gunter Donn, Hofheim (DE); Nathalie Knittel, Kriftel (DE); Arianna Martelletti, Sulzbach (DE); Richard Rees, Research Triangle Park, NC (US); Michael Schwall, Baden-Baden (DE)

(73) Assignee: Bayer CropScience AG, Monheim (DE)

( * ) Notice: Subject to any disclaimer, the term of this patent is extended or adjusted under 35 U.S.C. 154(b) by 170 days.

(21) Appl. No.: 10/584,489

(22) PCT Filed: Dec. 15, 2004

(86) PCT No.: PCT/EP2004/014272

§ 371 (c)(1), (2), (4) Date: Jun. 22, 2006

(87) PCT Pub. No.: WO2005/063020

PCT Pub. Date: Jul. 14, 2005

(65) Prior Publication Data

US 2007/0149406 A1 Jun. 28, 2007

(30) Foreign Application Priority Data

Dec. 24, 2003 (EP) .................................. 03029847
May 12, 2004 (EP) .................................. 04011252

(51) Int. Cl.
*A01N 43/56* (2006.01)
*A01N 43/48* (2006.01)
*A01N 43/54* (2006.01)
*A01N 43/52* (2006.01)
*A01N 43/50* (2006.01)

(52) U.S. Cl. ..................... 504/215; 534/770; 548/373.1
(58) Field of Classification Search ................. 504/215; 534/770; 548/373.1
See application file for complete search history.

(56) References Cited

U.S. PATENT DOCUMENTS

| | | | |
|---|---|---|---|
| 4,631,211 A | 12/1986 | Houghten | |
| 4,771,066 A | 9/1988 | Gehring et al. | |
| 4,787,930 A | 11/1988 | Gehring et al. | |
| 4,810,283 A | 3/1989 | Gehring et al. | |
| 5,013,659 A | 5/1991 | Bedbrook et al. | |
| 5,047,550 A | 9/1991 | D'Silva | |
| 5,232,940 A | 8/1993 | Hatton et al. | |
| 5,556,873 A | 9/1996 | Huang et al. | |
| 5,707,934 A | 1/1998 | Royalty et al. | |
| 5,776,760 A | 7/1998 | Barry et al. | |
| 6,215,042 B1 | 4/2001 | Willmitzer et al. | |
| 6,538,178 B1 | 3/2003 | Kishore | |
| 6,784,338 B1 | 8/2004 | Hofvander et al. | |

FOREIGN PATENT DOCUMENTS

| | | | |
|---|---|---|---|
| EP | 0 142 924 A2 | 5/1985 |
| EP | 0 193 259 A1 | 9/1986 |
| EP | 0 221 044 A1 | 5/1987 |
| EP | 0 242 236 A1 | 10/1987 |
| EP | 0 242 246 A1 | 10/1987 |
| EP | 0 257 993 A2 | 3/1988 |
| EP | 0 295 117 A1 | 12/1988 |
| GB | 1 444 678 | 8/1976 |
| JP | 2000-103784 A | 4/2000 |
| JP | 2002-265452 A | 9/2002 |
| WO | WO 84/02919 A1 | 8/1984 |
| WO | WO 87/03781 A1 | 2/1987 |
| WO | WO 91/13972 A1 | 9/1991 |
| WO | WO 93/06089 A1 | 4/1993 |
| WO | WO 94/21606 A1 | 9/1994 |
| WO | WO 01/40195 A2 | 6/2001 |
| WO | WO 02/066423 A1 | 8/2002 |

OTHER PUBLICATIONS

Patent Abstracts of Japan English language abstract of JP 2000-103784 A, cited as document FP2 on Form PTO/SB/08A.
Patent Abstracts of Japan English language abstract of JP 2002-265452 A, cited as document FP3 on Form PTO/SB/08A.
International Preliminary Report on Patentability for International application No. PCT/EP2004/014272, European Patent Office, Netherlands, mailed Nov. 11, 2005.
Amon, A., et al., "Mechanisms That Help the Yeast Cell Cycle Clock Tick: G2 Cyclins Transcriptionally Activate G2 Cyclins and Repress G1 Cyclins," *Cell 74*: 993-1007, Cell Press (1993).
Braun, H.-P., et al., "The general mitochondrial processing peptidase from potato is an integral part of cytochrome c reductase of the respiratory chain," *EMBO J. 11*:3219-3227, Oxford University Press (1992).

(Continued)

*Primary Examiner*—Johann R Richter
*Assistant Examiner*—Courtney Brown
(74) *Attorney, Agent, or Firm*—Sterne, Kessler, Goldstein & Fox P.L.L.C.

(57) ABSTRACT

The present invention relates to a new class of plant growth regulators. In particular, the invention relates to 5-substituted-1-arylpyrazole-3-carboxylic acid derivative of general formula (I) and a method for treatment of plants with such compounds in order to induce growth regulating responses.

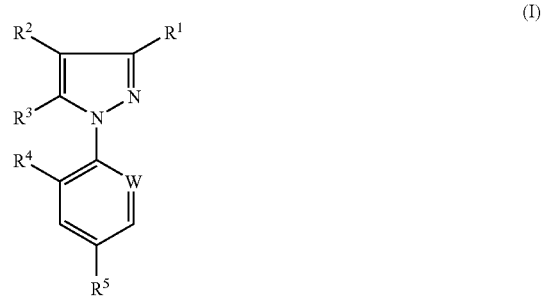

(I)

23 Claims, No Drawings

OTHER PUBLICATIONS

Biochemistry & Molecular Biology of Plants, "Chapter 11, Cell Division Regulation," Bunchanan *eds.*, pp. 542-565, American Society of Plant Physiologists, Rockville, MD (2000).

Biochemistry & Molecular Biology of Plants, Chapter 17, Biosynthesis of Hormones and Elicitor Molecules Bunchanan *eds.*, pp. 850-929, American Society of Plant Physiologists, Rockville, MD (2000).

Biochemistry & Molecular Biology of Plants, "Chapter 18, Signal Perception and Transduction," Bunchanan *eds.*, pp. 980-985, American Society of Plant Physiologists, Rockville, MD (2000).

Christou, P., "Transformation technology," *Trends Plant Sci.* 1:423-431, Elsevier Science Ltd. (1996).

Dynlacht, B.D., "Regulation of transcription by proteins that control the cell cycle," *Nature* 389:149-152, Macmillan Magazines Ltd. (1997).

Houghten, R.A., "General method for the rapid solid-phase systhesis of large numbers of peptides: Specificity of antigen-antibody interaction at the level of individual amino acids," *Proc. Natl. Acad. Sci. USA* 82:5131-5135, The National Academy of Sciences (1985).

Hunt, T., and Nasmyth, K., "Cell multiplication," *Curr. Opin. Cell. Biol.* 9:765-767, Current Biology Ltd. (1997).

Morgan, D.O., et al., "Cyclin-Dependent Kinases: Engines, Clocks, and Microprocessors," *Annu. Rev. Cell. Dev. Biol.* 13:261-291, Annual Reviews Inc. (1997).

Perry's Chemical Engineer's Handbook, $5^{TH}$ Ed, "Size Enlargement", pp. 8-57 - 8-65, McGraw-Hill Inc., New York (1973).

Sonnewald, U., et al., "Transgenic tobacco plants expressing yeast-derived invertase in etiher the cytosol, vacuole or apoplast: a powerful tool for studying sucrose metabolism and sink/source interactions," *Plant J.* 1:95-106, Blackwell Scientific Publishers and BIOS Scientific Publishers in association with the Society for Experimental Biology (1991).

Thomas, G., and Hall, M.N., "TOR signalling and control of cell growth," *Curr. Opin. Cell Biol.* 9:782-787, Current Biology Ltd. (1997).

Weed Control Handbook, "Chapter 5. The Application of Herbicides," vol. I. Fryer, J.D., and Evans, S.A. *eds.*, $5^{th}$ edition, pp. 101-103, Blackwell Scientific Publications, Oxford and Edinburgh (1968).

Wolter, F.P., et al., "*rbcS genes in Solanum tuberosum*: Conservation of transit peptide and exon shuffling during evolution," *Proc. Natl. Acad. Sci USA* 85:846-850, The National Academy of Sciences (1988).

PLANT GROWTH REGULATION

Present invention relates to the technical field of agrochemicals and methods used in agriculture for plant growth regulation. In particular, the present invention relates to a new class of plant growth regulators for the treatment of plants in order to induce growth regulating responses which result in superior growth of treated plants, certain parts of the plants or, more generally, crop yield.

The term "method for plant growth regulation" or the term "growth regulation process" or the use of the words "plant growth regulation" or other terms using the word "regulate" as used in instant specification relate to a variety of plant responses which improve some characteristic of the plant. "Plant growth regulators" are compounds which possess activity in one or more growth regulation process(es) of a plant.

This type of plant growth regulation is distinguished from pesticidal action or growth reduction, sometimes also defined as a plant growth regulation, the intention of which, however, is to destroy or stunt the growth of a plant. For this reason, the compounds used in the practice of this invention are used in amounts which are non-phytotoxic with respect to the plant being treated but which stimulate the growth of the plant or certain parts thereof Therefore, such compounds may also be called "plant stimulants", their action may be called as "plant growth stimulation".

Plant growth regulation is a desirable way to improve plants and their cropping so as to obtain improved plant growth and better conditions of agriculture practice compared to non-treated plants. This kind of molecules can either inhibit or promote cellular activities, often with a lower specificity compared to animal hormones. This means that plant growth regulators identified in plants most often regulate division, elongation and differentiation of plant cells in a way that, most often, they have multiple effects in plants.

On the molecular basis, plant growth regulators may work by affecting membrane properties, controlling gene expression or affecting enzyme activity or being active in a combination of at least two of the before mentioned types of interaction.

Plant growth regulators are chemicals either of natural origin, also called plant hormones (like non-peptide hormones e.g. auxins, giberrellins, cytokinins, ethylene, brassinosteroids or abscisic acid, and salicilic acid), lipooligosaccharides (e.g. Nod factors), peptides (e.g. systemin), fatty acid derivatives (e.g. jasmonates), and oligosaccharins (for review see: Biochemistry & Molecular Biology of the Plant (2000); eds. Buchanan, Gruissem, Jones, pp. 558-562; and 850-929) , or they can be synthetically produced compounds (like derivatives of naturally occurring plant growth hormones, ethephon).

Plant growth regulators which work at very small concentrations can be found in many cells and tissues, but they seem to be concentrated in meristems and buds. Beside the selection of the right compound it is also relevant to look for the optimal environmental conditions because there are several factors known that may affect the action of growth hormones, like (a) the concentration of the plant growth regulator itself, (b) the quantity applied to the plant, (c) the time of application in relation to flowering date, (d) temperature and humidity prior to and after treatment, (e) plant moisture content, and several others.

Plant growth regulators can be either beneficial to the plant but sometimes can be used for weed control or to induce defoliation (like synthetic auxins 2,4-D and 2,4,5-T do).

The mode of action of existing plant growth regulators often is not known. Various targets are discussed and among those, most of the affected molecules are involved in cell division regulation, like arresting the cell cycle in stage G1 or G2, respectively, others for signaling drought stress responses (Biochemistry & Molecular Biology of the Plant (2000); eds. Buchanan, Gruissem, Jones, pp. 558-560). In any case, the hormone control can be identified as an extremely complex cascade of up and down regulations which, for example, can lead to a growth stimulation of one organ or cell typus of a plant but also can lead to a repression in other organs or cell typus of the same plant.

In many cases, kinases are involved either directly or indirectly in plant hormone control and among the kinases, protein kinases are central and highly specific control molecules in respect to cell cycle control. Such kinases are discussed as targets for several plant hormones, like it is the case for auxin and abscisic acid (Biochemistry & Molecular Biology of the Plant (2000); eds. Buchanan, Gruissem, Jones, pp. 542-565 and pp. 980-985; Morgan (1997), Annu. Rev. Cell. Dev. Biol., 13, 261-291; Amon et al. (1993), Cell, 74, pp. 993-1007; Dynlacht et al. (1997), Nature, 389, pp.149-152; Hunt and Nasmyth (1997), Curr. Opin. Cell. Biol., 9, pp. 765-767; Thomas and Hall (1997), Curr. Opin. Cell. Biol., 9, pp. 782-787).

Patent publication WO 96/33614 already describes the use of a N-arylpyrazole or N-heteroarylpyrazole compound to regulate plant growth. Furthermore, Patent publication number U.S. Pat. No. 4,810,283 describes the use of N-arylpyrazoles as herbicides.

Patent publication numbers WO 87/03781, EP 0295117, U.S. Pat. Nos. 5,556,873, 4,771,066 and WO 02/066423 describe the control of insects, arachnids and helminths with 1-arylpyrazole compounds.

In view of the above, it now, surprisingly, turned out that certain 5-substituted-1-arylpyrazole-3-carboxylic acid derivatives, and especially certain 5-amino-1-arylpyrazole-3-carboxylic acid derivatives do not primarily act as herbicides but show a superior behaviour in respect to be used for plant growth regulation.

The present invention relates to the use of a compound for plant growth regulation, preferably by application of the compound to plants, to the seeds from which they grow or to the locus in which they grow, in an effective plant growth regulating, preferably non-phytotoxic amount, which compound is a 5-substituted-1-arylpyrazole-3-carboxylic acid derivative of formula (I) or an agriculturally acceptable salt thereof:

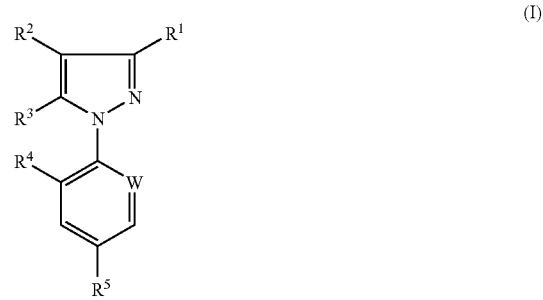

wherein:
$R^1$ is $CONR^6R^7$ or $CO_2R^8$;
W is C-halogen or N;
$R^2$ is H or $S(O)_mR^9$;

$R^3$ is $NR^{10}R^{11}$, halogen, OH, $(C_1$-$C_6)$-alkoxy, $(C_2$-$C_6)$-alkenyloxy or $(C_2$-$C_6)$-alkynyloxy;

$R^4$ is H or halogen, preferably H, Cl or Br;

$R^5$ is $(C_1$-$C_4)$-haloalkyl or $(C_1$-$C_4)$-haloalkoxy, preferably $CF_3$ or $OCF_3$;

$R^6$ is H, $(C_1$-$C_6)$-alkyl, $(C_1$-$C_6)$-haloalkyl, $(C_1$-$C_6)$-alkoxy-$(C_1$-$C_6)$-alkyl, $(C_2$-$C_6)$-alkenyl, $(C_2$-$C_6)$-haloalkenyl, $(C_2$-$C_6)$-alkynyl, $(C_2$-$C_6)$-haloalkynyl, $(C_3$-$C_7)$-cycloalkyl, $(C_3$-$C_7)$-cycloalkyl-$(C_1$-$C_6)$-alkyl, $(C_1$-$C_6)$-alkoxy, $(C_1$-$C_6)$-alkylthio, $(CH_2)_nR^{12}$, $(CH_2)_pR^{13}$, $(C_1$-$C_6)$-alkyl-CN, $(C_1$-$C_6)$-alkyl-$NR^{10}R^{11}$ or $(C_1$-$C_6)$-alkyl-$S(O)_rR^9$;

$R^7$ is H, $(C_1$-$C_6)$-alkyl, $(C_3$-$C_6)$-alkenyl or $(C_3$-$C_6)$-alkynyl; or $R^6$ and $R^7$ together with the attached N atom form a five- or six-membered saturated ring which optionally contains an additional hetero atom in the ring which is selected from O, S and N, the ring being unsubstituted or substituted by one or more radicals selected from the group consisting of halogen, $(C_1$-$C_6)$-alkyl and $(C_1$-$C_6)$-haloalkyl;

$R^8$ is H, $(C_1$-$C_6)$-alkyl, $(C_1$-$C_6)$-haloalkyl, $(C_2$-$C_6)$-alkenyl, $(C_2$-$C_6)$-alkynyl or $(CH_2)_nR^{12}$, preferably H or $(C_1$-$C_4)$-alkyl or $C_1$-$C_4)$-haloalkyl, particularly methyl or ethyl;

$R^9$ is $(C_1$-$C_6)$-alkyl or $(C_1$-$C_6)$-haloalkyl;

$R^{10}$ and $R^{11}$ are each independently H, $(C_1$-$C_6)$-alkyl, $(C_1$-$C_6)$-haloalkyl, $(C_2$-$C_6)$-alkenyl, $(C_2$-$C_6)$-haloalkenyl, $(C_2$-$C_6)$-alkynyl, $(C_3$-$C_6)$-cycloalkyl, $(C_3$-$C_6)$-cycloalkyl-$(C_1$-$C_6)$-alkyl, $COR^{14}$ or $CO_2R^{15}$; or $R^{10}$ and $R^{11}$ together with the attached N atom form a five- or six-membered saturated ring which optionally contains an additional hetero atom in the ring which is selected from O, S and N, the ring being unsubstituted or substituted by one or more radicals selected from the group consisting of halogen, $(C_1$-$C_6)$-alkyl and $(C_1$-$C_6)$-haloalkyl;

$R^{12}$ is phenyl unsubstituted or substituted by one or more radicals selected from the group consisting of halogen, $(C_1$-$C_6)$-alkyl, $(C_1$-$C_6)$-haloalkyl, $(C_1$-$C_6)$-alkoxy, $(C_1$-$C_6)$-haloalkoxy, $CO_2R^{16}$, CN, $NO_2$, $S(O)_qR^9$, $COR^{16}$, $CONR^{16}R^{17}$, $NR^{16}R^{17}$ and OH;

$R^{13}$ is heterocyclyl unsubstituted or substituted by one or more radicals selected from the group consisting of halogen, $(C_1$-$C_4)$-alkyl, $(C_1$-$C_4)$-haloalkyl, $(C_1$-$C_4)$-alkoxy, $(C_1$-$C_4)$-haloalkoxy, $NO_2$, CN, $CO_2R^{16}$, $S(O)_qR^9$, OH and oxo;

$R^{14}$ and $R^{15}$ are each independently H, $(C_1$-$C_6)$-alkyl, $(C_1$-$C_6)$-haloalkyl, $(C_2$-$C_6)$-alkenyl, $(C_2$-$C_6)$-haloalkenyl, $(C_2$-$C_6)$-alkynyl or $(C_1$-$C_6)$-alkoxy-$(C_1$-$C_4)$-alkyl;

$R^{16}$ and $R^{17}$ are each independently H, $(C_1$-$C_6)$-alkyl or $(C_1$-$C_6)$-haloalkyl;

m, q and r are each independently 0, 1 or 2;

n and p are each independently 0, 1, 2, 3 or 4; and each heterocyclyl in the above-mentioned radicals is independently a heterocyclic radical having 3 to 7 ring atoms and 1, 2 or 3 hetero atoms in the ring selected from the group consisting of N, O and S.

The invention also encompasses any stereoisomer, enantiomer, geometric isomer or tautomer, and mixtures of the compounds of formula (I) and the respective agricultirally acceptable salts thereof.

By the term "agriculturally acceptable salts" is meant salts the anions or cations of which are known and accepted in the art for the formation of salts for agricultural use.

Suitable salts with bases, e.g. formed by compounds of formula (I) containing a carboxylic acid group, include alkali metal (e.g. sodium and potassium), alkaline earth metal (e.g. calcium and magnesium) and ammonium salts. The ammonium salts include ammonium ($NH_4^+$) and ammonium salts of organic amines, (e.g. the diethanolamine, triethanolamine, octylamine, morpholine and dioctylmethylamine salts), and quaternary ammonium salts ($NR_4^+$) for example tetramethylammonium. ammonium salts. Suitable acid addition salts, e.g. formed by compounds of formula (I) containing an amino group, include salts with inorganic acids, for example hydrochlorides, sulphates, phosphates and nitrates and salts with organic acids for example acetic acid.

In the present patent specification, including the accompanying claims, the aforementioned substituents have the following meanings:

Halogen means fluorine, chlorine, bromine or iodine.

The term "halo" before the name of a radical means that this radical is partially or completely halogenated, that is to say, substituted by F, Cl, Br, or I, in any combination.

The expression "$(C_1$-$C_6)$-alkyl" means an unbranched or branched non-cyclic saturated hydrocarbon radical having 1, 2, 3, 4, 5 or 6 carbon atoms (indicated by a range of C-atoms in the parenthesis), such as, for example a methyl, ethyl, propyl, isopropyl, 1-butyl, 2-butyl, 2-methylpropyl or tert-butyl radical. The same applies to alkyl groups in composite radicals such as "alkoxy-alkyl".

Alkyl radicals and also in composite groups, unless otherwise defined, preferably have 1 to 4 carbon atoms.

"$(C_1$-$C_6)$-Haloalkyl" means an alkyl group mentioned under the expression "$(C_1$-$C_6)$-alkyl" in which one or more hydrogen atoms are replaced by the same number of identical or different halogen atoms, such as monohaloalkyl, perhaloalkyl, $CF_3$, $CHF_2$, $CH_2F$, $CHFCH_3$, $CF_3CH_2$, $CF_3CF_2$, $CHF_2CF_2$, $CH_2FCHCl$, $CH_2Cl$, $CCl_3$, $CHCl_2$ or $CH_2CH_2Cl$.

"$(C_1$-$C_6)$-Alkoxy-$(C_1$-$C_6)$-alkyl" means $(C_1$-$C_6)$-alkyl which is substituted by $(C_1$-$C_6)$-alkoxy.

"$(C_1$-$C_6)$-Alkoxy" means an alkoxy group whose carbon chain has the meaning given under the expression "$(C_1$-$C_6)$-alkyl". "Haloalkoxy" is, for example, $OCF_3$, $OCHF_2$, $OCH_2F$, $CF_3CF_2O$, $OCH_2CF_3$ or $OCH_2CH_2Cl$.

"$(C_2$-$C_6)$-Alkenyl" means an unbranched or branched non-cyclic carbon chain having a number of carbon atoms which corresponds to this stated range and which contains at least one double bond which can be located in any position of the respective unsaturated radical. "$(C_2$-$C_6)$-Alkenyl" accordingly denotes, for example, the vinyl, allyl, 2-methyl-2-propenyl, 2-butenyl, pentenyl, 2-methylpentenyl or the hexenyl group.

"$(C_2$-$C_6)$-Alkynyl" means an unbranched or branched non-cyclic carbon chain having a number of carbon atoms which corresponds to this stated range and which contains one triple bond which can be located in any position of the respective unsaturated radical. "$(C_2$-$C_6)$-Alkynyl" accordingly denotes, for example, the propargyl, 1-methyl-2-propynyl, 2-butynyl or 3-butynyl group.

"$(C_3$-$C_6)$-Cycloalkyl" denotes monocyclic alkyl radicals, such as the cyclopropyl, cyclobutyl, cyclopentyl or cyclohexyl radical.

"$(C_3$-$C_7)$-Cycloalkyl-$(C_1$-$C_6)$-alkyl" means a $(C_1$-$C_6)$-alkyl group which is substituted by a $(C_3$-$C_7)$-cycloalkyl group, for example cyclopropylmethyl.

"$(C_1$-$C_6)$-Alkyl-CN" means a $(C_1$-$C_6)$-alkyl group which is substituted by a CN group, for example cyanoethyl.

"$(Cl$-$C_6)$-Alkyl-$S(O)_rR^9$" means a $(C_1$-$C_6)$-alkyl group which is substituted by a $S(O)_rR^9$ group, for example methylthiomethyl.

A "heterocyclyl" group can be saturated, unsaturated or heteroaromatic; it preferably contains one or more, in particular 1, 2 or 3, hetero atoms in the heterocyclic ring, preferably selected from the group consisting of N, O and S; it is preferably an aliphatic heterocyclyl radical having 3 to 7 ring atoms or a heteroaromatic radical having 5 to 7 ring atoms. The heterocyclic radical can be, for example, a heteroaromatic radical or ring (heteroaryl) such as, for example, a mono-, bi- or polycyclic aromatic system in which at least 1 ring contains one or more hetero atoms, for example pyridyl, pyrimidinyl, pyridazinyl, pyrazinyl, triazinyl, thienyl, thiazolyl, thiadiazolyl, oxazolyl, isoxazolyl, furyl, pyrrolyl, pyrazolyl, imidazolyl and triazolyl, or it is a partially or fully hydrogenated radical such as oxiranyl, oxetanyl, oxolanyl (=tetrahydrofuryl), oxanyl, pyrrolidyl, piperidyl, piperazinyl, dioxolanyl, oxazolinyl, isoxazolinyl, oxazolidinyl, isoxazolidinyl and morpholinyl.

The expression "one or more radicals selected from the group consisting of" in the definition is to be understood as meaning in each case one or more identical or different radicals selected from the stated group of radicals, unless specific limitations are defined expressly.

Compounds of the stated formula (I) according to the invention or their salts in which individual radicals have one of the preferred meanings which have already been stated or are stated hereinbelow and particularly those shown in the Table examples, or in particular those in which two or more of the preferred meanings which have already been stated or which are stated hereinbelow are combined, are of particular interest, mainly because of the more potent herbicidal action, better selectivity and/or greater ease of preparation.

Of particular interest are compounds of formula (I) where a radical selected from the group of radicals $R^1$, $R^2$, $R^3$, $R^4$, $R^5$ and W is preferably defined as set forth below, wherein the definition of the radical is independent from the definitions of the other radicals of said group. Preferred compounds of formula (I) contain a combination of radicals of said group which comprise two or more preferred meanings set forth below.

In the following preferred definitions it is generally to be understood that where symbols are not specifically defined they are to be as previously defined in the description.

Preferably $R^1$ is $CONR^6R^7$.

Preferably W is C—Cl or C—Br (more preferably W is C—Cl).

Preferably $R^2$ is $S(O)_mR^9$, wherein $R^9$ is $(C_1-C_3)$-alkyl or $(C_1-C_3)$-haloalkyl (more preferably $R^9$ is $CF_3$).

Preferably $R^3$ is $NR^{10}R^{11}$, halogen, OH or $(C_1-C_3)$-alkoxy.

Preferably $R^4$ is Cl or Br (more preferably $R^4$ is Cl).

Preferably $R^5$ is $CF_3$ or $OCF_3$.

Preferably $R^6$ is H, $(C_1-C_4)$-alkyl, $(C_1-C_4)$-haloalkyl, $(C_1-C_3)$-alkoxy-$(C_1-C_3)$-alkyl-, $(C_3-C_4)$-alkenyl, $(C_3-C_4)$-haloalkenyl, $(C_3-C_4)$-alkynyl, $(C_3-C_4)$-haloalkynyl, $(C_3-C_6)$-cycloalkyl, $(C_3-C_6)$-cycloalkyl-$(C_1-C_3)$-alkyl, $(C_1-C_3)$-alkoxy, $(C_1-C_3)$-alkylthio, $(CH_2)_nR^{12}$, $(CH_2)_pR^{13}$, $(C_1-C_6)$-alkyl-CN, $(C_1-C_6)$-alkyl-$NR^{10}R^{11}$ or $(C_1-C_6)$-alkyl-$S(O)_rR^9$.

Preferably $R^7$ is H, $(C_1-C_4)$-alkyl, $(C_3-C_4)$-alkenyl or $(C_3-C_4)$-alkynyl; or preferably $R^6$ and $R^7$ together with the attached N atom form a five- or six-membered saturated ring which optionally contains an additional hetero atom in the ring which is selected from O, S and N, the ring being unsubstituted or substituted by one or more radicals selected from the group consisting of halogen, $(C_1-C_3)$-alkyl and $(C_1-C_3)$-haloalkyl.

Preferably $R^{10}$ and $R^{11}$ are each independently H, $(C_1-C_3)$-alkyl, $(C_1-C_3)$-haloalkyl, $(C_3-C_4)$-alkenyl, $(C_3-C_4)$-haloalkenyl, $(C_3-C_4)$-alkynyl, $(C_3-C_6)$-cycloalkyl, $(C_3-C_6)$-cycloalkyl-$(C_1-C_3)$-alkyl, $COR^{14}$ or $CO_2R^{15}$; or preferably $R^{10}$ and $R^{11}$ together with the attached N atom form a five- or six-membered saturated ring which optionally contains an additional hetero atom in the ring which is selected from O, S and N, the ring being unsubstituted or substituted by one or more radicals selected from the group consisting of halogen, $(C_1-C_3)$-alkyl and $(C_1-C_3)$-haloalkyl.

Preferably $R^{12}$ is phenyl unsubstituted or substituted by one or more radicals selected from the group consisting of halogen, $(C_1-C_3)$-alkyl, $(C_1-C_3)$-haloalkyl, $(C_1-C_3)$-alkoxy, $(C_1-C_3)$-haloalkoxy, $CO_2R^{16}$, CN, $NO_2$, $S(O)_qR^9$, $COR^{16}$, $CONR^{16}R^{17}$, $NR^{16}R^{17}$ and OH.

Preferably $R^{13}$ is heterocyclyl unsubstituted or substituted by one or more radicals selected from the group consisting of halogen, $(C_1-C_3)$-alkyl, $(C_1-C_3)$-haloalkyl, $(C_1-C_3)$-alkoxy, $(C_1-C_3)$-haloalkoxy, $NO_2$, CN, $CO_2R^{16}$, $S(O)_qR^9$, OH and oxo.

Preferably $R^{14}$ and $R^{15}$ are each independently H, $(C_1-C_3)$-alkyl, $(C_1-C_3)$-haloalkyl, $(C_2-C_3)$-alkenyl, $(C_2-C_3)$-haloalkenyl or $(C_2-C_3)$-alkynyl, particularly $(C_1-C_4)$-alkyl.

Preferably $R^{16}$ and $R^{17}$ are each independently H, $(C_1-C_3)$-alkyl or $(C_1-C_3)$-haloalkyl.

Preferably each heterocyclyl in the above-mentioned radicals is independently a heterocyclic radical having 3 to 6 ring atoms and 1, 2 or 3 hetero atoms in the ring selected from the group consisting of N, O and S.

A preferred class of compounds of formula (I) for the use as plant growth regulators in the invention are those in which:

$R^1$ is $CONR^6R^7$;

W is C—Cl or C—Br (more preferably W is C—Cl);

$R^2$ is $S(O)_mR^9$;

$R^3$ is $NR^{10}R^{11}$, halogen, OH, $(C_1-C_3)$-alkoxy, $(C_2-C_6)$-alkenyloxy or $(C_2-C_6)$-alkynyloxy;

$R^4$ is Cl or Br (more preferably $R^4$ is Cl);

$R^5$ is $CF_3$ or $OCF_3$;

$R^6$ is H, $(C_1-C_4)$-alkyl, $(C_1-C_4)$-haloalkyl, $(C_1-C_3)$-alkoxy-$(C_1-C_3)$-alkyl, $(C_3-C_4)$-alkenyl, $(C_3-C_4)$-haloalkenyl, $(C_3-C_4)$-alkynyl, $(C_3-C_4)$-haloalkynyl, $(C_3-C_6)$-cycloalkyl, $(C_3-C_6)$-cycloalkyl-$(C_1-C_3)$-alkyl, $(C_1-C_3)$-alkoxy, $(C_1-C_3)$-alkylthio, $(CH_2)_nR^{12}$ or $(CH_2)_pR^{13}$, $R^7$ is H, $(C_1-C_4)$-alkyl, $(C_3-C_4)$-alkenyl or $(C_3-C_4)$-alkynyl; or preferably $R^6$ and $R^7$ together with the attached N atom form a five- or six-membered saturated ring which optionally contains an additional hetero atom in the ring which is selected from O, S and N, the ring being unsubstituted or substituted by one or more radicals selected from the group consisting of halogen, $(C_1-C_3)$-alkyl and $(C_1-C_3)$-haloalkyl;

$R^9$ is $(C_1-C_3)$-alkyl or $(C_1-C_3)$-haloalkyl (more preferably $R^9$ is $CF_3$);

$R^{10}$ and $R^{11}$ are each independently H, $(C_1-C_3)$-alkyl, $(C_1-C_3)$-haloalkyl, $(C_3-C_4)$-alkenyl, $(C_3-C_4)$-haloalkenyl, $(C_3-C_4)$-alkynyl, $(C_3-C_6)$-cycloalkyl, $(C_3-C_6)$-cycloalkyl-$(C_1-C_3)$-alkyl, $COR^{14}$ or $CO_2R^{15}$; or $R^{10}$ and $R^{11}$ together with the attached N atom form a five- or six-membered saturated ring which optionally contains an additional hetero atom in the ring which is selected from O, S and N, the ring being unsubstituted or substituted by one or more radicals selected from the group consisting of halogen, $(C_1-C_3)$-alkyl and $(C_1-C_3)$-haloalkyl;

$R^{12}$ is phenyl unsubstituted or substituted by one or more radicals selected from the group consisting of halogen, $(C_1-C_3)$-alkyl, $(C_1-C_3)$-haloalkyl, $(C_1-C_3)$-alkoxy, $(C_1-C_3)$-haloalkoxy, $CO_2R^{16}$, CN, $NO_2$, $S(O)_qR^9$, $COR^{16}$, $CONR^{16}R^{17}$, $NR^{16}R^{17}$ and OH;

$R^{13}$ is heterocyclyl unsubstituted or substituted by one or more radicals selected from the group consisting of halogen, $(C_1-C_3)$-alkyl, $(C_1-C_3)$-haloalkyl, $(C_1-C_3)$-alkoxy, $(C_1-C_3)$-haloalkoxy, $NO_2$, CN, $CO_2R^{16}$, $S(O)_qR^9$, OH and oxo;

$R^{14}$ and $R^{15}$ are each independently H, $(C_1-C_3)$-alkyl, $(C_1-C_3)$-haloalkyl, $(C_2-C_3)$-alkenyl, $(C_2-C_3)$-haloalkenyl, $(C_2-C_3)$-alkynyl or $(C_1-C_6)$-alkoxy-$(C_1-C_4)$-alkyl;

$R^{16}$ and $R^{17}$ are each independently H, $(C_1-C_3)$-alkyl or $(C_1-C_3)$-haloalkyl; and each heterocyclyl in the above-mentioned radicals is independently a heterocyclic radical having 3 to 6 ring atoms and 1, 2 or 3 hetero atoms in the ring selected from the group consisting of N, O and S.

A further preferred class of compounds of formula (I) for the use as plant growth regulators in the invention are those in which:
$R^1$ is $CONR^6R^7$;
W is C—Cl;
$R^2$ is H, or $S(O)_mR^9$;
$R^3$ is $NR^{10}R^{11}$, halogen, OH or $(C_1-C_3)$-alkoxy;
$R^4$ is Cl;
$R^5$ is $CF_3$;
$R^6$ is H, $(C_1-C_4)$-alkyl, $(C_1-C_3)$-alkoxy-$(C_1-C_2)$-alkyl, $(C_3-C_4)$-alkenyl, $(C_3-C_4)$-alkynyl, $(C_3-C_6)$-cycloalkyl, $(C_3-C_6)$-cycloalkyl-$(C_1-C_2)$-alkyl, $(C_1-C_3)$-alkoxy, $(C_1-C_3)$-alkylthio, $(CH_2)_nR^{12}$ or $(CH_2)_pR^{13}$;
$R^7$ is H, $(C_1-C_3)$-alkyl, $(C_3-C_4)$-alkenyl or $(C_3-C_4)$-alkynyl;
$R^9$ is methyl, ethyl or $CF_3$;
$R^{10}$ and $R^{11}$ are each independently H, $(C_1-C_3)$-alkyl, $(C_1-C_3)$-haloalkyl, $(C_3-C_4)$-alkenyl, $(C_3-C_4)$-haloalkenyl, $(C_3-C_4)$-alkynyl, $(C_3-C_6)$-cycloalkyl, $(C_3-C_6)$-cycloalkyl-$(C_1-C_3)$-alkyl, $COR^{14}$ or $CO_2R^{15}$; or
$R^{12}$ is phenyl unsubstituted or substituted by one or more radicals selected from the group consisting of halogen, $(C_1-C_3)$-alkyl, $(C_1-C_3)$-haloalkyl, $(C_1-C_3)$-alkoxy, $CO_2R^{16}$, CN and $NO_2$;
$R^{13}$ is heterocyclyl unsubstituted or substituted by one or more radicals selected from the group consisting of halogen, $(C_1-C_3)$-alkyl, $(C_1-C_3)$-haloalkyl, $(C_1-C_3)$-alkoxy, $(C_1-C_3)$-haloalkoxy, $NO_2$, CN, $CO_2R^{16}$, $S(O)_qR^9$, OH and oxo;
$R^{14}$ and $R^{15}$ are each independently $(C_1-C_3)$-alkyl;
$R^{16}$ and $R^{17}$ are each independently H or $(C_1-C_3)$-alkyl; and each heterocyclyl in the above-mentioned radicals is independently a heterocyclic radical having 3 to 6 ring atoms and 1, 2 or 3 hetero atoms in the ring selected from the group consisting of N, O and S.

A further preferred class of compounds for the use as plant growth regulators in the invention are of formula (Ia), as depicted hereinafter, in which:
$R^1$ is $CONR^6R^7$;
W is C—Cl;
$R^2$ is H, or $S(O)_mR^9$;
$R^3$ is $NHR^{10}$;
$R^4$ is Cl;
$R^5$ is $CF_3$;
$R^6$ is H, $(C_1-C_5)$-alkyl, $(C_1-C_2)$-alkoxy-$(C_1-C_2)$-alkyl, $(C_3-C_4)$-alkenyl, $(C_3-C_4)$-alkynyl, $(C_3-C_6)$-cycloalkyl, $(C_3-C_6)$-cycloalkyl-$(C_1-C_2)$-alkyl, furfuryl or tetrahydrofurfuryl;
$R^7$ is H or $(C_1-C_3)$-alkyl;
$R^9$ is methyl, ethyl or $CF_3$; and
$R^{10}$ is H, methyl or ethyl.

A further preferred class of compounds for the use as plant growth regulators in the invention are of formula (Ib), as depicted hereinafter, in which:
$R^1$ is $CO_2R^8$;
W is C—Cl;
$R^2$ is H, or $S(O)_mR^9$;
$R^3$ is $NR^{10}R^{11}$;
$R^4$ is Cl;
$R^5$ is $CF_3$;
$R^8$ is H, methyl or ethyl;
$R^9$ is methyl, ethyl or $CF_3$;
$R^{10}$ is H, methyl or ethyl; and
$R^{11}$ is H.

A further preferred class of compounds for the use as plant growth regulators in the invention are of formula (Ic), as depicted hereinafter, in which:
$R^1$ is $CONR^6R^7$;
W is C—Cl;
$R^2$ is $S(O)_mCF_3$;
$R^3$ is $NR^{10}R^{11}$, halogen, OH or $(C_1-C_2)$-alkyl;
$R^4$ is Cl;
$R^5$ is $CF_3$;
$R^6$ is H or $(C_1-C_3)$-alkylthio;
$R^7$ is H;
$R^{10}$ is $(C_1-C_3)$-alkyl, $COR^{14}$ or $CO_2R^{15}$;
$R^{11}$, $R^{14}$ and $R^{15}$ are each independently $(C_1-C_3)$-alkyl.

Some of the compounds of formula (I) are not known in the prior art. Therefore, a further feature of the invention relates to these novel compounds of formula (I).

Thus, according to a further feature of the invention there is provided a 5-substituted-1-arylpyrazole-3-carboxylic acid derivative of formula (I), or a salt thereof as defined in formula (I),

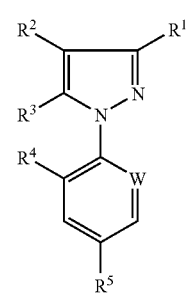

(I)

wherein:
i) $R^1$ is $CO_2R^8$;
$R^2$ is H or $S(O)_mR^9$;
$R^3$, $R^4$, $R^5$, W and m are as defined above;
$R^8$ is H; and
$R^9$ is $(C_2-C_6)$-alkyl or $(C_1-C_6)$-haloalkyl;

or ii) $R^1$ is $CONR^6R^7$;
$R^6$ is $(C_1-C_6)$-alkyl, $(C_1-C_6)$-haloalkyl, $(C_1-C_6)$-alkoxy-$(C_1-C_6)$-alkyl, $(C_2-C_6)$-alkenyl, $(C_2-C_6)$-haloalkenyl, $(C_2-C_6)$-alkynyl, $(C_2-C_6)$-haloalkynyl, $(C_3-C_7)$-cycloalkyl, $(C_3-C_7)$-cycloalkyl-$(C_1-C_6)$-alkyl, $(C_1-C_6)$-alkoxy, $(C_1-C_6)$-alkylthio, $(CH_2)_nR^{12}$, $(CH_2)_pR^{13}$, $(C_1-C_6)$-alkyl-CN, $(C_1-C_6)$-alkyl-$NR^{10}R^{11}$ or $(C_1-C_6)$-alkyl-$S(O)_rR^9$; or $R^6$ and $R^7$ together with the attached N atom form a five- or six-membered saturated ring which optionally contains an additional hetero atom in the ring which is selected from O, S and N, the ring being unsubstituted or substituted by one or more radicals selected from the group consisting of halogen, $(C_1-C_6)$-alkyl and $(C_1-C_6)$-haloalkyl; and $R^2$, $R^3$, $R^4$, $R^5$, $R^7$, $R^9$, $R^{10}$, $R^{11}$, $R^{12}$, $R^{13}$, W, n, p and r are as defined in formula (I);

with the exclusion of the compound wherein:
R$^1$ is CON(CH$_3$)$_2$; R$^2$ is CF$_3$S; R$^3$ is OH; R$^4$ is Cl; R$^5$ is CF$_3$; and W is C—Cl.

The above compound is specifically excluded because it is known, however, its use as a plant growth regulator has not yet been reported.

Compounds of formula (I) above may be prepared by the application or adaptation of known methods (i.e. methods heretofore used or described in the literature). In the following description where symbols appearing in formulae are not specifically defined, it is to be understood that they are "as hereinbefore defined" in accordance with the first definition of each symbol in the specification.

It is to be understood that in the descriptions of the following processes the sequences may be performed in different orders, and that suitable protecting groups may be required to achieve the compounds sought.

Compounds of formula (I) above may be prepared by the application or adaptation of known methods (i.e. methods heretofore used or described in the literature).

In the following description where symbols appearing in formulae are not specifically defined, it is to be understood that they are "as hereinbefore defined" in accordance with the first definition of each symbol in the specification.

It is to be understood that in the descriptions of the following processes the sequences may be performed in different orders, and that suitable protecting groups may be required to achieve the compounds sought.

According to a feature of the invention compounds of formula (I) wherein R$^1$ is CO$_2$H, R$^2$ is H or S(O)$_m$R$^9$, R$^9$ is (C$_2$-C$_6$)-alkyl or (C$_1$-C$_6$)-haloalkyl, and the other values are as defined above, may be prepared by the reaction of a corresponding compound of formula (II):

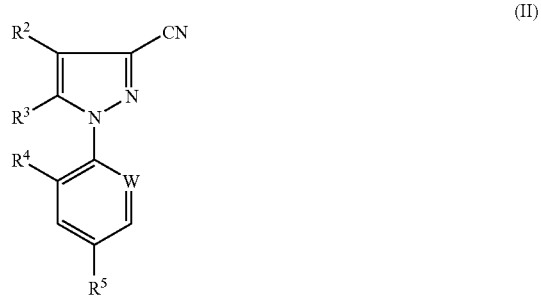

(II)

wherein R$^2$, R$^3$, R$^4$, R$^5$ and W are as defined above, using aqueous sulfuric acid, generally 40% to 60% sulfuric acid at a temperature of from 80° C. to 170° C., preferably from 120° C. to 150° C.

According to a further feature of the invention compounds of formula (I) wherein R$^1$ is CO$_2$H, R$^2$ is H, R$^3$ is NHR$^{11}$, and the other values are as defined above, may be prepared by the reaction of a corresponding compound of formula (II) above wherein R$^2$ is R$^9$SO or R$^9$SO$_2$ (preferably CF$_3$SO or CF$_3$SO$_2$), using aqueous sulfuric acid, generally 40% to 60% sulfuric acid at a temperature of from 80° C. to 170° C. preferably from 120° C. to 150° C.

According to a further feature of the invention compounds of formula (I) wherein R$^1$ is CONR$^6$R$^7$; R$^6$ is (C$_1$-C$_6$)-alkyl, (C$_1$-C$_6$)-haloalkyl, (C$_1$-C$_6$)-alkoxy-(C$_1$-C$_6$)-alkyl, (C$_2$-C$_6$)-alkenyl, (C$_2$-C$_6$)-haloalkenyl, (C$_2$-C$_6$)-alkynyl, (C$_2$-C$_6$)-haloalkynyl, (C$_3$-C$_7$)-cycloalkyl, (C$_3$-C$_7$)-cycloalkyl-(C$_1$-C$_6$)-alkyl, (C$_1$-C$_6$)-alkoxy, (CH$_2$)$_n$R$^{12}$, (CH$_2$)$_p$R$^{13}$, (C$_1$-C$_6$)-alkyl-CN, (C$_1$-C$_6$)-alkyl-NR$^{10}$R$^{11}$ or (C$_1$-C$_6$)-alkyl-S(O)$_r$R$^9$; R$^7$ is as defined above; or R$^6$ and R$^7$ together with the attached N atom form a five- or six-membered saturated ring which optionally contains an additional hetero atom in the ring which is selected from O, S and N, the ring being unsubstituted or substituted by one or more radicals selected from the group consisting of halogen, (C$_1$-C$_6$)-alkyl and (C$_1$-C$_6$)-haloalkyl; and the other values are as defined above, may be prepared by the reaction of a corresponding compound of formula (I) wherein R$^1$ is CO$_2$H, with N,N'-carbonyldiimidazole to give the corresponding imidazolide of formula (III):

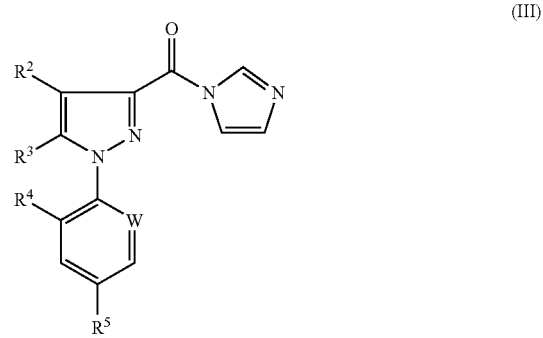

(III)

followed by the reaction, preferably in situ, with an amine of formula (IV):

HNR$^6$R$^7$ (IV)

wherein R$^6$ and R$^7$ are as defined above. The reaction is generally performed in a solvent such as tetrahydrofuran or dioxan, at a temperature of from 20° C. to 100° C., preferably from 30° C. to 70° C.

According to a further feature of the invention compounds of formula (I) wherein R$^3$ is NR$^{10}$R$^{11}$ in which at least one of R$^{10}$ and R$^{11}$ is not H, and the other values are as defined above, may be prepared by the alkylation or acylation of the corresponding compound of formula (I) wherein R$^3$ is NH$_2$, using an alkylating or acylating agent of formula (V) or (VI):

R$^{10}$-L (V)

R$^{11}$-L$^1$ (VI)

wherein R$^{10}$ and R$^{11}$ are as defined above with the exclusion of H, and L and L$^1$ are each a leaving group.

Alkylations, where R$^{10}$ and/or R$^{11}$ are each (C$_1$-C$_6$)-alkyl, (Cl-C$_6$)-haloalkyl, (C$_3$-C$_6$)-alkenyl, (C$_3$-C$_6$)-haloalkenyl, (C$_3$-C$_6$)-alkynyl, (C$_3$-C$_6$)-cycloalkyl or (C$_3$-C$_6$)-cycloalkyl-(C$_1$-C$_6$)-alkyl, and L and L$^1$ are each preferably halogen, alkylsulfonyloxy or arylsulfonyloxy (more preferably chlorine, bromine, iodine, methylsulfonyloxy or p-toluenesulfonyloxy), are generally carried out in the presence of a base, in an inert solvent such as tetrahydrofuran, dioxan, acetonitrile, toluene, diethyl ether, dichloromethane, dimethylsulfoxide or N,N-dimethylformamide, at a temperature of from −30° C. to 200° C., preferably at 20° C. to 100° C. The base is generally an alkali metal hydroxide such as potassium hydroxide, an alkali metal hydride such as sodium hydride, an alkali metal carbonate such as potassium carbonate or sodium carbonate, an alkali metal alkoxide such as sodium methoxide, an alkaline earth metal carbonate such as calcium carbonate, or an organic base such as a tertiary amine, for example triethylamine or ethyldiisopropylamine, or pyridine, or 1,8-diazabi-cyclo[5.4.0]undec-7-en (DBU).

Acylations, where $R^{10}$ and/or $R^{11}$ are each $COR^{14}$ or $CO_2R^{15}$, and L and $L^1$ are each preferably chlorine or bromine (more preferably chlorine), are performed optionally in the presence of a base. The bases, solvents and temperatures which may be used are similar to those employed for the alkylations.

By performing sequential alkylation or acylation reactions, compounds of formula (I) wherein $R^3$ is $NR^{10}R^{11}$ in which $R^{10}$ and $R^{11}$ have different values may be prepared.

According to a further feature of the invention compounds of formula (I) wherein $R^1$ is $CONR^6R^7$, $R^2$ is $S(O)_mR^9$, $R^3$ is $(C_1-C_6)$-alkoxy, $R^6$ is $(C_1-C_6)$-alkylthio, and the other values are as defined above, may be prepared by the reaction of a corresponding compound of formula (I) wherein $R^1$ is $CONHR^7$, with a compound of formula (VII):

$$R^6\text{-}L^2 \quad \text{(VII)}$$

wherein $R^6$ is $(C_1-C_6)$-alkylthio, and $L^2$ is a leaving group, generally halogen and preferably Cl.

According to a further feature of the present invention compounds wherein m is 1 or 2, and the other values are as defined above, may be prepared by oxidising a corresponding compound in which m is 0 or 1. The oxidation is generally performed using an oxidising agent such as m-chloroperbenzoic acid or sodium periodate in an inert solvent for example methylene chloride at a temperature from −40° C. to the reflux temperature of the solvent.

Compounds of formula (I) wherein $R^1$ is $CONH_2$ may be prepared from the corresponding compounds in which $R^1$ is CN according to known methods, for example by the reaction with concentrated sulfuric acid at a temperature of from 50° C. to 150° C.

Intermediate compounds of formula (II) wherein $R^3$ is $NR^{10}R^{11}$ or halogen may be prepared according to methods described in Patent Publication numbers WO 87/03781, EP 295117 and U.S. Pat. No. 5,232,940.

Intermediate compounds of formula (II) wherein $R^3$ is $(C_1-C_6)$-alkoxy may be prepared according to methods described in Patent Publication numbers EP 035809 and U.S. Pat. No. 5,047,550.

Intermediate compounds of formula (II) wherein $R^3$ is OH may be prepared according to methods described in Patent Publication number WO 01/40195.

Compounds of formula (III) are novel and as such form a further feature of the invention, and may be prepared as described above.

Compounds of formula (II), (IV), (V), (VI) and (VII) are known or may be prepared according to known methods.

A collection of compounds of formula (I) which can be synthesized by the above-mentioned processes can additionally be prepared in parallel fashion, which can be effected manually, partly automated or fully automated. In this context, it is possible to automate the procedure of the reaction, work-up or purification of the products or intermediates. In total, this is to be understood as meaning a procedure which is described, for example, by S. H. DeWitt in "Annual Reports in Combinatorial Chemistry and Molecular Diversity: Automated Synthesis", Volume 1, published by Escom, 1997, pages 69 to 77.

For carrying out the reaction and work-up in parallel fashion, a series of commercially available apparatuses can be used as they are available from, for example, Stem Corporation, Woodrolfe Road, Tollesbury, Essex, CM9 8SE, England or Radleys Discovery Technologies, Saffron Walden, Essex, CB11 3AZ, ENGLAND. To carry out the parallel purification of compounds (I) or of intermediates obtained during the preparation, there are available, inter alia, chromatographic equipment, for example from ISCO, Inc., 4700 Superior Street, Lincoln, Nebr. 68504, USA. The equipment mentioned makes possible a modular procedure, where the individual steps are automated, but manual operation has to be carried out between the steps. This can be circumvented by employing partly or fully integrated automation systems, in which the automation modules in question are operated by, for example, robots. Such automation systems can be obtained from, for example, Zymark Corporation, Zymark Center, Hopkinton, Mass. 01748, USA.

In addition to the above-described methods, compounds of formula (I) can be prepared in full or partly by solid-phase supported methods. To this end, individual intermediates or all intermediates of the synthesis or of a synthesis adapted to the procedure in question are bound to a synthesis resin. Solid-phase supported synthetic methods are described extensively in the specialist literature, for example: Barry A. Bunin in "The Combinatorial Index", published by Academic Press, 1998. The use of solid-phase supported synthesis methods permits a series of protocols known from the literature which, in turn, can be carried out manually or in an automated fashion. For example, the "teabag method" (Houghten, U.S. Pat. No. 4,631,211; Houghten et al., Proc. Natl. Acad. Sci., 1985, 82, 5131-5135) can be partly automated with products of IRORI, 11149 North Torrey Pines Road, La Jolla, Calif. 92037, USA. Solid-phase supported parallel synthesis can be automated successfully for example using equipment by Argonaut Technologies, Inc., 887 Industrial Road, San Carlos, Calif. 94070, USA or MultiSynTech GmbH, Wullener Feld 4, 58454 Witten, Germany.

The preparation in accordance with the processes described herein yields compounds of formula (I) in the form of substance collections or substance libraries. Subject matter of the present invention are therefore also libraries of the compounds of formula (I) which contain at least two compounds of formula (I), and of their precursors.

The following non-limiting Examples illustrate the preparation of the compounds of formula (I).

A. CHEMICAL EXAMPLES

In the Examples which follow, quantities (also percentages) are weight based unless stated otherwise. Ratios of solvents are volume based.

Example 1

5-Amino-1-(2,6-dichloro-4-trifluoromethylphenyl)-4-trifluoromethylthio-1H-pyrazole-3-carboxylic acid
(Compound 2.10)

A stirred mixture of 5-amino-1-(2,6-dichloro-4-trifluoromethylphenyl)-4-trifluoromethylthio-1H-pyrazole-3-carbonitrile (35.5 g, 84.3 mmol) and sulfuric acid (50%, 600 ml) was heated to 135° C. for 7 hours. The cooled mixture was added to ice water and the precipitate filtered off, washed with water and air-dried. Trituration with tetrachloromethane gave the title compound as off-white crystals (30.6 g, yield 82%), mp 199° C., $^1$H NMR (DMSO-d6): 6.66 (bs, 2H, $NH_2$), 8.23 (s, 2H, Ar—H), and 13.03 (bs, 1H, COOH).

Example 2

5-Amino-1-(2,6-dichloro-4-trifluoromethylphenyl)-4-trifluoromethylthio-1H-pyrazole-3-carboxylic acid amide (Compound 1.4)

A mixture of 5-amino-1-(2,6-dichloro-4-trifluoromethylphenyl)-4-trifluoromethylthio-1H-pyrazole-3-carboxylic acid (1.00 g, 2.27 mmol) and 1,1-dicarbonylimidazole (0.45 g, 2.72 mmol) in dioxane was heated to 50° C. for 2 hours. An aqueous solution of ammonia (33%, 80 ml) was then added and stirring continued at 50° C. for 4 hours. The cooled mixture was diluted with water and extracted with ethyl acetate/heptane (1:1). The combined organic phase was washed with aqueous potassium hydrogensulfate (5%), dried over magnesium sulfate and evaporated to give the title compound (0.980 g, yield 98%) as a white foam, $^1$H NMR (CDCl$_3$): 4.36 (bs, 2H, NH$_2$), 5.60 and 6.69 (bs, 2H, C(O)NH$_2$), and 7.82 (s, 2H, Ar—H).

Example 3

5-Amino-1-(2,6-dichloro-4-trifluoromethylphenyl)-4-trifluoromethylthio-1H-pyrazole-3-carboxylic acid cyclopropylamide (Compound 1.1)

A mixture of 5-amino-1-(2,6-dichloro-4-trifluoromethylphenyl)-4-trifluoromethylthio-1H-pyrazole-3-carboxylic acid (0.85 g, 1.83 mmol) and 1,1-dicarbonylimidazole (0.36 g, 2.20 mmol) in dioxane was heated to. 55° C. for 2 hours. Cyclopropylamine (0.20 ml, 2.83 mmol) was then added and stirring continued at 55° C. for 6 hours. The cooled mixture was diluted with water, extracted with ethyl acetate, washed with aqueous potassium hydrogensulfate (5%), dried over magnesium sulfate and evaporated to give the title compound (0.762 g, yield 87%) as off-white crystals, mp 193° C., $^1$H NMR (CDCl$_3$): 0.64 (m, 2H, cyclopropyl), 0.83 (m, 2H, cyclopropyl), 2,87 (m,1H, cyclopropyl), 4.31 (bs, 2H, NH$_2$), 6.82 (bs,1 H, C(O)NH), and 7.80 (s, 2H, Ar—H).

Example 4

5-Amino-1-(2,6-dichloro-4-trifluoromethylphenyl)-4-trifluoromethylsulfinyl-1H-pyrazole-3-carboxylic acid propargylamide (Compound 1.134)

To a suspension of 5-amino-1-(2,6-dichloro-4-trifluoromethylphenyl)-4-trifluoromethylthio-I H-pyrazole-3-carboxylic acid propargylamide (0.71 g, 1.43 mmol) in dichloromethane was slowly added a solution of m-chloroperbenzoic acid (70%, 0.41 g, 1.68 mmol) in dichloromethane. After stirring for 17 hours at 20° C., an aqueous solution of sodium sulfite/sodium hydrogen carbonate (5%: 5%, 25 ml) was added and stirring continued for 15 minutes. The aqueous phase was extracted with dichloromethane, dried over magnesium sulfate, evaporated and purified by flash chomatography (silica, heptane/ethyl acetate) to give the title compound (0.604 g, yield 86%) as white crystals, mp 207° C., $^1$H NMR (CDCl$_3$): 2.28 (t, 1H, propargyl), 4.20 (m, 2H, propargyl), 5.17 (bs, 2H, NH$_2$), 6.88 (bt, 1H, C(O)NH), and 7.83 (s, 2H, Ar—H).

Example 5

5-Amino-1-(2,6-dichloro-4-trifluoromethylphenyl)-4-trifluoromethylsulfonyl-1H-pyrazole-3-carboxylic acid amide (Compound 1.268)

A stirred mixture of 5-amino-1-(2,6-dichloro-4-trifluoromethylphenyl)-4-trifluoromethylsulfonyl-1 H-pyrazole-3-carbonitrile (1.06 g, 2.21 mmol) and concentrated sulfuric acid (1 ml) was heated to 100° C. for 3 hours. The cooled mixture was added to ice water and the precipitate filtered off, washed with water and air-dried. Purification by flash chomatography (silica, chloroform) gave the title compound (0.869 g, yield 83%) as off-white crystals, mp 217° C., $^1$H NMR (DMSO-d6): 7.39 (bs, 2H, NH$_2$), 7.57 and 7.78 (bs, 2H, C(O)NH$_2$), and 8.25 (s, 2H, Ar—H).

Example 6

5-Amino-1-(2,6-dichloro-4-trifluoromethylphenyl)-1H-pyrazole-3-carboxylic acid (Compound 2.1)

A stirred mixture of 5-amino-1-(2,6-dichloro-4-trifluoromethylphenyl)-4-trifluoromethylsulfinyl-1 H-pyrazole-3-carbonitrile (5.00 g, 11.4 mmol) and sulfuric acid (50%, 100 ml) was heated to 135° C. for 3 hours. The cooled mixture was added to ice water and the pH adjusted to 4 by the addition of aqueous sodium hydroxide (6 N, approx. 230 ml), and then extracted with ethyl acetate. The organic phase was dried over magnesium sulfate, evaporated to dryness and purified by flash chomatography (silica, chloroform/ethanol) with subsequently trituration with tetrachloromethane to give the title compound (3.00 g, yield 77%) as off-white crystals, mp 213° C., $^1$H NMR (DMSO-d6): 5.69 (bs, 2H, NH$_2$), 5.76 (s, 1H, pyrazole-H), and 8.20 (s, 2H, Ar—H).

Example 7

1-(2,6-Dichloro-4-trifluoromethylphenyl)-5-ethoxy-4-trifluoromethylthio-1H-pyrazole-3-carboxylic acid amide (Compound 3.3)

a) To a stirred suspension of sodium hydride (0.41 g, 60%, 10.3 mmol) in dioxane (150 ml) was added a solution of 1-(2,6-dichloro-4-trifluoromethylphenyl)-5-hydroxy-4-trifluoromethylthio-1H-pyrazole-3-carbonitrile (4.00 g, 8.53 mmol) in dioxane (50 ml). After gas evolution had ceased the mixture was heated to reflux and diethyl sulfate (1.25 ml, 9.47 mmol) added, and then heated under reflux for 6 hours. The cooled mixture was acidified with aqueous potassium hydrogensulfate (5%), extracted with dichloromethane, and the organic phase dried over magnesium sulfate and evaporated. The resulting gum was triturated with pentane to give 1-(2,6-dichloro-4-trifluoromethylphenyl)-5-ethoxy-4-trifluoromethylthio-1 H-pyrazole-3-carbonitrile (2.68 g, yield 70 %) as off-white crystals, mp 106° C., $^1$H NMR (CDCl$_3$): 1.36 (t, 3H, CH$_3$), 4.71 (q, 2H, OCH$_2$), and 7.76 (s, 2H, Ar—H).

b) A stirred mixture of 1-(2,6-dichloro-4-trifluoromethylpheny)-5-ethoxy-4-trifluoromethylthio-1 H-pyrazole-3-carbonitrile (0.55 g, 1.22 mmol) and concentrated sulfuric acid (0.55 ml) was heated at 100° C. for 3 hours. The cooled mixture was added to ice water and the precipitate filtered off, washed with water and air-dried. The crude product was dissolved in heptanes/ethyl acetate (1:1) and filtered. The filtrate was evaporated to give the title compound (0.42 g, yield 73%) as yellowish crystals, mp 161° C., $^1$H NMR (CDCl$_3$): 1.32 (t, 3H, CH$_3$), 4.68 (q, 2H, OCH$_2$), 5.54 and 6.69 (bs, 2H, C(O)NH$_2$), and 7.77 (s, 2H, Ar—H).

The following preferred compounds of formula (Ia), (Ib) and (Ic) shown in Tables 1 to 3 also form part of the present invention, and are obtained by, or analogously to, the above Examples 1 to 7 or the above-described general methods.

The following abbreviations are used in the Tables 1 to 3:

"Cpd" means Compound Number. Compound numbers are given for reference purposes only. RF means retention time determined from thin layer chromatography on silica gel, using ethyl acetate as eluent.

TABLE 1

Compounds of formula (Ia)

(Ia)

| Cpd | $R^2$ | $R^6$ | $R^7$ | $R^{10}$ | mp (° C.) | RF |
|---|---|---|---|---|---|---|
| 1.1 | $SCF_3$ | cyclopropyl | H | H | 193 | 0.88 |
| 1.2 | $SCF_3$ | $CH_2CH\!=\!CH$ | H | H | foam | 0.90 |
| 1.3 | $SCF_3$ | $CH_2CH\!=\!CH_2$ | H | H | 169 | 0.94 |
| 1.4 | $SCF_3$ | H | H | H | foam | 0.90 |
| 1.5 | $SCF_3$ | $CH_3$ | H | H | foam | 0.90 |
| 1.6 | $SCF_3$ | $CH_2CH_3$ | H | H | 196 | 0.93 |
| 1.7 | $SCF_3$ | $CH_2CH_2CH_3$ | H | H | 187 | 0.97 |
| 1.8 | $SCF_3$ | $CH(CH_3)_2$ | H | H | 215 | 0.90 |
| 1.9 | $SCF_3$ | $CH_2(CH_2)_3CH_3$ | H | H | 150 | 0.92 |
| 1.10 | $SCF_3$ | cyclohexyl | H | H | 172 | 0.94 |
| 1.11 | $SCF_3$ | $CH_2CH_2OCH_3$ | H | H | foam | 0.88 |
| 1.12 | $SCF_3$ | 2-tetrahydrofurfuryl | H | H | foam | 0.89 |
| 1.13 | $SCF_3$ | 2-furfuryl | H | H | foam | 0.94 |
| 1.14 | $SCF_3$ | $CH_2CN$ | H | H | | |
| 1.15 | $SCF_3$ | $CH_2CH_2CN$ | H | H | | |
| 1.16 | $SCF_3$ | $CH_2$-cyclopropyl | H | H | | |
| 1.17 | $SCF_3$ | $CH_2CH_2CH(CH_3)_2$ | H | H | | |
| 1.18 | $SCF_3$ | $CH_2CH_2N(CH_3)_2$ | H | H | | |
| 1.19 | $SCF_3$ | $CH_2CH_2CH_2OCH_3$ | H | H | | |
| 1.20 | $SCF_3$ | $CH_2CH_2SCH_3$ | H | H | | |
| 1.21 | $SCF_3$ | $CH_2CF_3$ | H | H | | |
| 1.22 | $SCF_3$ | $CH_2(CH_2)_2CH\!=\!CH_2$ | H | H | | |
| 1.23 | $SCF_3$ | $CH_2(CH_2)_4CH_3$ | H | H | | |
| 1.24 | $SCF_3$ | $CH_2(CH_2)_2SCH_3$ | H | H | | |
| 1.25 | $SCF_3$ | $CH_2C_6H_5$ | H | H | | |
| 1.26 | $SCF_3$ | $CH_2$-3-pyridyl | H | H | | |
| 1.27 | $SCF_3$ | 5-$CH_3$-furfur-2-yl | H | H | | |
| 1.28 | $SCF_3$ | $CH_2$-thiophen-2-yl | H | H | | |
| 1.29 | $SCF_3$ | $CH_2CH_2C_6H_5$ | H | H | | |
| 1.30 | $SCF_3$ | $CH_2CH_2$-3-pyridyl | H | H | | |
| 1.31 | $SCF_3$ | $CH_2(CH_2)_2$—N-imidazolyl | H | H | | |
| 1.32 | $SCF_3$ | cyclopropyl | $CH_3$ | H | | |
| 1.33 | $SCF_3$ | $CH_2CH\!=\!CH$ | $CH_3$ | H | | |
| 1.34 | $SCF_3$ | $CH_2CH\!=\!CH_2$ | $CH_3$ | H | foam | 0.87 |
| 1.35 | $SCF_3$ | $CH_3$ | $CH_3$ | H | 183 | 0.87 |
| 1.36 | $SCF_3$ | $CH_2CH_3$ | $CH_3$ | H | foam | 0.91 |
| 1.37 | $SCF_3$ | $CH_2CH_2CH_3$ | $CH_3$ | H | foam | 0.88 |
| 1.38 | $SCF_3$ | $CH(CH_3)_2$ | $CH_3$ | H | | |
| 1.39 | $SCF_3$ | $CH_2(CH_2)_3CH_3$ | $CH_3$ | H | | |
| 1.40 | $SCF_3$ | cyclohexyl | $CH_3$ | H | | |
| 1.41 | $SCF_3$ | $CH_2CH_2OCH_3$ | $CH_3$ | H | | |
| 1.42 | $SCF_3$ | 2-tetrahydrofurfuryl | $CH_3$ | H | | |
| 1.43 | $SCF_3$ | 2-furfuryl | $CH_3$ | H | | |
| 1.44 | $SCF_3$ | $CH_2CN$ | $CH_3$ | H | | |
| 1.45 | $SCF_3$ | $CH_2CH_2CN$ | $CH_3$ | H | | |
| 1.46 | $SCF_3$ | $CH_2$-cyclopropyl | $CH_3$ | H | | |
| 1.47 | $SCF_3$ | $CH_2CH_2CH(CH_3)_2$ | $CH_3$ | H | | |
| 1.48 | $SCF_3$ | $CH_2CH_2N(CH_3)_2$ | $CH_3$ | H | | |
| 1.49 | $SCF_3$ | $CH_2CH_2CH_2OCH_3$ | $CH_3$ | H | | |
| 1.50 | $SCF_3$ | $CH_2CH_2SCH_3$ | $CH_3$ | H | | |
| 1.51 | $SCF_3$ | $CH_2CF_3$ | $CH_3$ | H | | |
| 1.52 | $SCF_3$ | $CH_2(CH_2)_2CH\!=\!CH_2$ | $CH_3$ | H | | |

TABLE 1-continued

Compounds of formula (Ia)

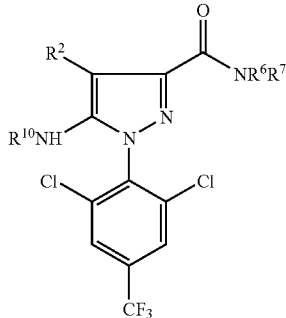

(Ia)

| Cpd | $R^2$ | $R^6$ | $R^7$ | $R^{10}$ | mp (° C.) | RF |
|---|---|---|---|---|---|---|
| 1.53 | $SCF_3$ | $CH_2(CH_2)_4CH_3$ | $CH_3$ | H | | |
| 1.54 | $SCF_3$ | $CH_2(CH_2)_2SCH_3$ | $CH_3$ | H | | |
| 1.55 | $SCF_3$ | $CH_2C_6H_5$ | $CH_3$ | H | | |
| 1.56 | $SCF_3$ | $CH_2$-3-pyridyl | $CH_3$ | H | | |
| 1.57 | $SCF_3$ | 5-$CH_3$-furfur-2-yl | $CH_3$ | H | | |
| 1.58 | $SCF_3$ | $CH_2$-thiophen-2-yl | $CH_3$ | H | | |
| 1.59 | $SCF_3$ | $CH_2CH_2C_6H_5$ | $CH_3$ | H | | |
| 1.60 | $SCF_3$ | $CH_2CH_2$-3-pyridyl | $CH_3$ | H | | |
| 1.61 | $SCF_3$ | $CH_2(CH_2)_2$—N-imidazolyl | $CH_3$ | H | | |
| 1.62 | $SCF_3$ | cyclopropyl | H | $CH_3$ | | |
| 1.63 | $SCF_3$ | $CH_2CH{=}CH$ | H | $CH_3$ | | |
| 1.64 | $SCF_3$ | $CH_2CH{=}CH_2$ | H | $CH_3$ | | |
| 1.65 | $SCF_3$ | H | H | $CH_3$ | foam | 0.90 |
| 1.66 | $SCF_3$ | $CH_3$ | H | $CH_3$ | | |
| 1.67 | $SCF_3$ | $CH_2CH_3$ | H | $CH_3$ | | |
| 1.68 | $SCF_3$ | $CH_2CH_2CH_3$ | H | $CH_3$ | | |
| 1.69 | $SCF_3$ | $CH(CH_3)_2$ | H | $CH_3$ | | |
| 1.70 | $SCF_3$ | $CH_2(CH_2)_3CH_3$ | H | $CH_3$ | | |
| 1.71 | $SCF_3$ | cyclohexyl | H | $CH_3$ | | |
| 1.72 | $SCF_3$ | $CH_2CH_2OCH_3$ | H | $CH_3$ | | |
| 1.73 | $SCF_3$ | 2-tetrahydrofurfuryl | H | $CH_3$ | | |
| 1.74 | $SCF_3$ | 2-furfuryl | H | $CH_3$ | | |
| 1.75 | $SCF_3$ | $CH_2CN$ | H | $CH_3$ | | |
| 1.76 | $SCF_3$ | $CH_2CH_2CN$ | H | $CH_3$ | | |
| 1.77 | $SCF_3$ | $CH_2$-cyclopropyl | H | $CH_3$ | | |
| 1.78 | $SCF_3$ | $CH_2CH_2CH(CH_3)_2$ | H | $CH_3$ | | |
| 1.79 | $SCF_3$ | $CH_2CH_2N(CH_3)_2$ | H | $CH_3$ | | |
| 1.80 | $SCF_3$ | $CH_2CH_2CH_2OCH_3$ | H | $CH_3$ | | |
| 1.81 | $SCF_3$ | $CH_2CH_2SCH_3$ | H | $CH_3$ | | |
| 1.82 | $SCF_3$ | $CH_2CF_3$ | H | $CH_3$ | | |
| 1.83 | $SCF_3$ | $CH_2(CH_2)_2CH{=}CH_2$ | H | $CH_3$ | | |
| 1.84 | $SCF_3$ | $CH_2(CH_2)_4CH_3$ | H | $CH_3$ | | |
| 1.85 | $SCF_3$ | $CH_2(CH_2)_2SCH_3$ | H | $CH_3$ | | |
| 1.86 | $SCF_3$ | $CH_2C_6H_5$ | H | $CH_3$ | | |
| 1.87 | $SCF_3$ | $CH_2$-3-pyridyl | H | $CH_3$ | | |
| 1.88 | $SCF_3$ | 5-$CH_3$-furfur-2-yl | H | $CH_3$ | | |
| 1.89 | $SCF_3$ | $CH_2$-thiophen-2-yl | H | $CH_3$ | | |
| 1.90 | $SCF_3$ | $CH_2CH_2C_6H_5$ | H | $CH_3$ | | |
| 1.91 | $SCF_3$ | $CH_2CH_2$-3-pyridyl | H | $CH_3$ | | |
| 1.92 | $SCF_3$ | $CH_2(CH_2)_2$—N-imidazolyl | H | $CH_3$ | | |
| 1.93 | $SCF_3$ | cyclopropyl | $CH_3$ | $CH_3$ | | |
| 1.94 | $SCF_3$ | $CH_2CH{=}CH$ | $CH_3$ | $CH_3$ | | |
| 1.95 | $SCF_3$ | $CH_2CH{=}CH_2$ | $CH_3$ | $CH_3$ | | |
| 1.96 | $SCF_3$ | $CH_3$ | $CH_3$ | $CH_3$ | foam | 0.90 |
| 1.97 | $SCF_3$ | $CH_2CH_3$ | $CH_3$ | $CH_3$ | | |
| 1.98 | $SCF_3$ | $CH_2CH_2CH_3$ | $CH_3$ | $CH_3$ | | |
| 1.99 | $SCF_3$ | $CH(CH_3)_2$ | $CH_3$ | $CH_3$ | | |
| 1.100 | $SCF_3$ | $CH_2(CH_2)_3CH_3$ | $CH_3$ | $CH_3$ | | |
| 1.101 | $SCF_3$ | cyclohexyl | $CH_3$ | $CH_3$ | | |
| 1.102 | $SCF_3$ | $CH_2CH_2OCH_3$ | $CH_3$ | $CH_3$ | | |
| 1.103 | $SCF_3$ | 2-tetrahydrofurfuryl | $CH_3$ | $CH_3$ | | |
| 1.104 | $SCF_3$ | 2-furfuryl | $CH_3$ | $CH_3$ | | |
| 1.105 | $SCF_3$ | $CH_2CN$ | $CH_3$ | $CH_3$ | | |
| 1.106 | $SCF_3$ | $CH_2CH_2CN$ | $CH_3$ | $CH_3$ | | |
| 1.107 | $SCF_3$ | $CH_2$-cyclopropyl | $CH_3$ | $CH_3$ | | |
| 1.108 | $SCF_3$ | $CH_2CH_2CH(CH_3)_2$ | $CH_3$ | $CH_3$ | | |
| 1.109 | $SCF_3$ | $CH_2CH_2N(CH_3)_2$ | $CH_3$ | $CH_3$ | | |

TABLE 1-continued

Compounds of formula (Ia)

$$\text{(Ia)}$$

| Cpd | $R^2$ | $R^6$ | $R^7$ | $R^{10}$ | mp (° C.) | RF |
|---|---|---|---|---|---|---|
| 1.110 | $SCF_3$ | $CH_2CH_2CH_2OCH_3$ | $CH_3$ | $CH_3$ | | |
| 1.111 | $SCF_3$ | $CH_2CH_2SCH_3$ | $CH_3$ | $CH_3$ | | |
| 1.112 | $SCF_3$ | $CH_2CF_3$ | $CH_3$ | $CH_3$ | | |
| 1.113 | $SCF_3$ | $CH_2(CH_2)_2CH=CH_2$ | $CH_3$ | $CH_3$ | | |
| 1.114 | $SCF_3$ | $CH_2(CH_2)_4CH_3$ | $CH_3$ | $CH_3$ | | |
| 1.115 | $SCF_3$ | $CH_2(CH_2)_2SCH_3$ | $CH_3$ | $CH_3$ | | |
| 1.116 | $SCF_3$ | $CH_2C_6H_5$ | $CH_3$ | $CH_3$ | | |
| 1.117 | $SCF_3$ | $CH_2$-3-pyridyl | $CH_3$ | $CH_3$ | | |
| 1.118 | $SCF_3$ | 5-$CH_3$-furfur-2-yl | $CH_3$ | $CH_3$ | | |
| 1.119 | $SCF_3$ | $CH_2$-thiophen-2-yl | $CH_3$ | $CH_3$ | | |
| 1.120 | $SCF_3$ | $CH_2CH_2C_6H_5$ | $CH_3$ | $CH_3$ | | |
| 1.121 | $SCF_3$ | $CH_2CH_2$-3-pyridyl | $CH_3$ | $CH_3$ | | |
| 1.122 | $SCF_3$ | $CH_2(CH_2)_2$—N-imidazolyl | $CH_3$ | $CH_3$ | | |
| 1.123 | $SCF_3$ | $CH_2CH_3$ | $CH_2CH_3$ | H | foam | 0.92 |
| 1.124 | $SCF_3$ | $CH_2CH_3$ | $CH_2CH_3$ | $CH_3$ | | |
| 1.125 | $SCF_3$ | —$CH_2(CH_2)_2CH_2$— | | H | | |
| 1.126 | $SCF_3$ | —$CH_2(CH_2)_3CH_2$— | | H | | |
| 1.127 | $SCF_3$ | —$CH_2CH_2OCH_2CH_2$— | | H | | |
| 1.128 | $SCF_3$ | —$CH_2CH_2N(CH_3)CH_2CH_2$— | | H | | |
| 1.129 | $SCF_3$ | —$CH_2(CH_2)_2CH_2$— | | $CH_3$ | | |
| 1.130 | $SCF_3$ | —$CH_2(CH_2)_3CH_2$— | | $CH_3$ | | |
| 1.131 | $SCF_3$ | —$CH_2CH_2OCH_2CH_2$— | | $CH_3$ | | |
| 1.132 | $SCF_3$ | —$CH_2CH_2N(CH_3)CH_2CH_2$— | | $CH_3$ | | |
| 1.133 | $S(O)CF_3$ | cyclopropyl | H | H | 180 | 0.93 |
| 1.134 | $S(O)CF_3$ | $CH_2CH\equiv CH$ | H | H | 207 | 0.93 |
| 1.135 | $S(O)CF_3$ | $CH_2CH=CH_2$ | H | H | oil | 0.94 |
| 1.136 | $S(O)CF_3$ | H | H | H | 224 | 0.91 |
| 1.137 | $S(O)CF_3$ | $CH_3$ | H | H | 205 | 0.90 |
| 1.138 | $S(O)CF_3$ | $CH_2CH_3$ | H | H | 211 | 0.91 |
| 1.139 | $S(O)CF_3$ | $CH_2CH_2CH_3$ | H | H | 206 | 0.96 |
| 1.140 | $S(O)CF_3$ | $CH(CH_3)_2$ | H | H | 191 | 0.89 |
| 1.141 | $S(O)CF_3$ | $CH_2(CH_2)_3CH_3$ | H | H | 171 | 0.91 |
| 1.142 | $S(O)CF_3$ | cyclohexyl | H | H | foam | 0.91 |
| 1.143 | $S(O)CF_3$ | $CH_2CH_2OCH_3$ | H | H | 164 | 0.90 |
| 1.144 | $S(O)CF_3$ | 2-tetrahydrofurfuryl | H | H | 141 | 0.91 |
| 1.145 | $S(O)CF_3$ | 2-furfuryl | H | H | foam | 0.93 |
| 1.146 | $S(O)CF_3$ | $CH_2CN$ | H | H | | |
| 1.147 | $S(O)CF_3$ | $CH_2CH_2CN$ | H | H | | |
| 1.148 | $S(O)CF_3$ | $CH_2$-cyclopropyl | H | H | | |
| 1.149 | $S(O)CF_3$ | $CH_2CH_2CH(CH_3)_2$ | H | H | | |
| 1.150 | $S(O)CF_3$ | $CH_2CH_2N(CH_3)_2$ | H | H | | |
| 1.151 | $S(O)CF_3$ | $CH_2CH_2CH_2OCH_3$ | H | H | | |
| 1.152 | $S(O)CF_3$ | $CH_2CH_2SCH_3$ | H | H | | |
| 1.153 | $S(O)CF_3$ | $CH_2CF_3$ | H | H | | |
| 1.154 | $S(O)CF_3$ | $CH_2(CH_2)_2CH=CH_2$ | H | H | | |
| 1.155 | $S(O)CF_3$ | $CH_2(CH_2)_4CH_3$ | H | H | | |
| 1.156 | $S(O)CF_3$ | $CH_2(CH_2)_2SCH_3$ | H | H | | |
| 1.157 | $S(O)CF_3$ | $CH_2C_6H_5$ | H | H | | |
| 1.158 | $S(O)CF_3$ | $CH_2$-3-pyridyl | H | H | | |
| 1.159 | $S(O)CF_3$ | 5-$CH_3$-furfur-2-yl | H | H | | |
| 1.160 | $S(O)CF_3$ | $CH_2$-thiophen-2-yl | H | H | | |
| 1.161 | $S(O)CF_3$ | $CH_2CH_2C_6H_5$ | H | H | | |
| 1.162 | $S(O)CF_3$ | $CH_2CH_2$-3-pyridyl | H | H | | |
| 1.163 | $S(O)CF_3$ | $CH_2(CH_2)_2$—N-imidazolyl | H | H | | |
| 1.164 | $S(O)CF_3$ | cyclopropyl | $CH_3$ | H | | |
| 1.165 | $S(O)CF_3$ | $CH_2CH\equiv CH$ | $CH_3$ | H | | |
| 1.166 | $S(O)CF_3$ | $CH_2CH=CH_2$ | $CH_3$ | H | foam | 0.92 |

TABLE 1-continued

Compounds of formula (Ia)

(Ia)

| Cpd | R² | R⁶ | R⁷ | R¹⁰ | mp (° C.) | RF |
|---|---|---|---|---|---|---|
| 1.167 | S(O)CF₃ | CH₃ | CH₃ | H | 196 | 0.90 |
| 1.168 | S(O)CF₃ | CH₂CH₃ | CH₃ | H | 185 | 0.91 |
| 1.169 | S(O)CF₃ | CH₂CH₂CH₃ | CH₃ | H | 156 | 0.89 |
| 1.170 | S(O)CF₃ | CH(CH₃)₂ | CH₃ | H | | |
| 1.171 | S(O)CF₃ | CH₂(CH₂)₃CH₃ | CH₃ | H | | |
| 1.172 | S(O)CF₃ | cyclohexyl | CH₃ | H | | |
| 1.173 | S(O)CF₃ | CH₂CH₂OCH₃ | CH₃ | H | | |
| 1.174 | S(O)CF₃ | 2-tetrahydrofurfuryl | CH₃ | H | | |
| 1.175 | S(O)CF₃ | 2-furfuryl | CH₃ | H | | |
| 1.176 | S(O)CF₃ | CH₂CN | CH₃ | H | | |
| 1.177 | S(O)CF₃ | CH₂CH₂CN | CH₃ | H | | |
| 1.178 | S(O)CF₃ | CH₂-cyclopropyl | CH₃ | H | | |
| 1.179 | S(O)CF₃ | CH₂CH₂CH(CH₃)₂ | CH₃ | H | | |
| 1.180 | S(O)CF₃ | CH₂CH₂N(CH₃)₂ | CH₃ | H | | |
| 1.181 | S(O)CF₃ | CH₂CH₂CH₂OCH₃ | CH₃ | H | | |
| 1.182 | S(O)CF₃ | CH₂CH₂SCH₃ | CH₃ | H | | |
| 1.183 | S(O)CF₃ | CH₂CF₃ | CH₃ | H | | |
| 1.184 | S(O)CF₃ | CH₂(CH₂)₂CH=CH₂ | CH₃ | H | | |
| 1.185 | S(O)CF₃ | CH₂(CH₂)₄CH₃ | CH₃ | H | | |
| 1.186 | S(O)CF₃ | CH₂(CH₂)₂SCH₃ | CH₃ | H | | |
| 1.187 | S(O)CF₃ | CH₂C₆H₅ | CH₃ | H | | |
| 1.188 | S(O)CF₃ | CH₂-3-pyridyl | CH₃ | H | | |
| 1.189 | S(O)CF₃ | 5-CH₃-furfur-2-yl | CH₃ | H | | |
| 1.190 | S(O)CF₃ | CH₂-thiophen-2-yl | CH₃ | H | | |
| 1.191 | S(O)CF₃ | CH₂CH₂C₆H₅ | CH₃ | H | | |
| 1.192 | S(O)CF₃ | CH₂CH₂-3-pyridyl | CH₃ | H | | |
| 1.193 | S(O)CF₃ | CH₂(CH₂)₂—N-imidazolyl | CH₃ | H | | |
| 1.194 | S(O)CF₃ | cyclopropyl | H | CH₃ | | |
| 1.195 | S(O)CF₃ | CH₂CH=CH | H | CH₃ | | |
| 1.196 | S(O)CF₃ | CH₂CH=CH₂ | H | CH₃ | | |
| 1.197 | S(O)CF₃ | H | H | CH₃ | 192 | 0.87 |
| 1.198 | S(O)CF₃ | CH₃ | H | CH₃ | | |
| 1.199 | S(O)CF₃ | CH₂CH₃ | H | CH₃ | | |
| 1.200 | S(O)CF₃ | CH₂CH₂CH₃ | H | CH₃ | | |
| 1.201 | S(O)CF₃ | CH(CH₃)₂ | H | CH₃ | | |
| 1.202 | S(O)CF₃ | CH₂(CH₂)₃CH₃ | H | CH₃ | | |
| 1.203 | S(O)CF₃ | cyclohexyl | H | CH₃ | | |
| 1.204 | S(O)CF₃ | CH₂CH₂OCH₃ | H | CH₃ | | |
| 1.205 | S(O)CF₃ | 2-tetrahydrofurfuryl | H | CH₃ | | |
| 1.206 | S(O)CF₃ | 2-furfuryl | H | CH₃ | | |
| 1.207 | S(O)CF₃ | CH₂CN | H | CH₃ | | |
| 1.208 | S(O)CF₃ | CH₂CH₂CN | H | CH₃ | | |
| 1.209 | S(O)CF₃ | CH₂-cyclopropyl | H | CH₃ | | |
| 1.210 | S(O)CF₃ | CH₂CH₂CH(CH₃)₂ | H | CH₃ | | |
| 1.211 | S(O)CF₃ | CH₂CH₂N(CH₃)₂ | H | CH₃ | | |
| 1.212 | S(O)CF₃ | CH₂CH₂CH₂OCH₃ | H | CH₃ | | |
| 1.213 | S(O)CF₃ | CH₂CH₂SCH₃ | H | CH₃ | | |
| 1.214 | S(O)CF₃ | CH₂CF₃ | H | CH₃ | | |
| 1.215 | S(O)CF₃ | CH₂(CH₂)₂CH=CH₂ | H | CH₃ | | |
| 1.216 | S(O)CF₃ | CH₂(CH₂)₄CH₃ | H | CH₃ | | |
| 1.217 | S(O)CF₃ | CH₂(CH₂)₂SCH₃ | H | CH₃ | | |
| 1.218 | S(O)CF₃ | CH₂C₆H₅ | H | CH₃ | | |
| 1.219 | S(O)CF₃ | CH₂-3-pyridyl | H | CH₃ | | |
| 1.220 | S(O)CF₃ | 5-CH₃-furfur-2-yl | H | CH₃ | | |
| 1.221 | S(O)CF₃ | CH₂-thiophen-2-yl | H | CH₃ | | |
| 1.222 | S(O)CF₃ | CH₂CH₂C₆H₅ | H | CH₃ | | |
| 1.223 | S(O)CF₃ | CH₂CH₂-3-pyridyl | H | CH₃ | | |

TABLE 1-continued

Compounds of formula (Ia)

| Cpd | $R^2$ | $R^6$ | $R^7$ | $R^{10}$ | mp (° C.) | RF |
|---|---|---|---|---|---|---|
| 1.224 | S(O)CF$_3$ | CH$_2$(CH$_2$)$_2$—N-imidazolyl | H | CH$_3$ | | |
| 1.225 | S(O)CF$_3$ | cyclopropyl | CH$_3$ | CH$_3$ | | |
| 1.226 | S(O)CF$_3$ | CH$_2$CH═CH | CH$_3$ | CH$_3$ | | |
| 1.227 | S(O)CF$_3$ | CH$_2$CH═CH$_2$ | CH$_3$ | CH$_3$ | | |
| 1.228 | S(O)CF$_3$ | CH$_3$ | CH$_3$ | CH$_3$ | 139 | 0.86 |
| 1.229 | S(O)CF$_3$ | CH$_2$CH$_3$ | CH$_3$ | CH$_3$ | | |
| 1.230 | S(O)CF$_3$ | CH$_2$CH$_2$CH$_3$ | CH$_3$ | CH$_3$ | | |
| 1.231 | S(O)CF$_3$ | CH(CH$_3$)$_2$ | CH$_3$ | CH$_3$ | | |
| 1.232 | S(O)CF$_3$ | CH$_2$(CH$_2$)$_3$CH$_3$ | CH$_3$ | CH$_3$ | | |
| 1.233 | S(O)CF$_3$ | cyclohexyl | CH$_3$ | CH$_3$ | | |
| 1.234 | S(O)CF$_3$ | CH$_2$CH$_2$OCH$_3$ | CH$_3$ | CH$_3$ | | |
| 1.235 | S(O)CF$_3$ | 2-tetrahydrofurfuryl | CH$_3$ | CH$_3$ | | |
| 1.236 | S(O)CF$_3$ | 2-furfuryl | CH$_3$ | CH$_3$ | | |
| 1.237 | S(O)CF$_3$ | CH$_2$CN | CH$_3$ | CH$_3$ | | |
| 1.238 | S(O)CF$_3$ | CH$_2$CH$_2$CN | CH$_3$ | CH$_3$ | | |
| 1.239 | S(O)CF$_3$ | CH$_2$-cyclopropyl | CH$_3$ | CH$_3$ | | |
| 1.240 | S(O)CF$_3$ | CH$_2$CH$_2$CH(CH$_3$)$_2$ | CH$_3$ | CH$_3$ | | |
| 1.241 | S(O)CF$_3$ | CH$_2$CH$_2$N(CH$_3$)$_2$ | CH$_3$ | CH$_3$ | | |
| 1.242 | S(O)CF$_3$ | CH$_2$CH$_2$CH$_2$OCH$_3$ | CH$_3$ | CH$_3$ | | |
| 1.243 | S(O)CF$_3$ | CH$_2$CH$_2$SCH$_3$ | CH$_3$ | CH$_3$ | | |
| 1.244 | S(O)CF$_3$ | CH$_2$CF$_3$ | CH$_3$ | CH$_3$ | | |
| 1.245 | S(O)CF$_3$ | CH$_2$(CH$_2$)$_2$CH═CH$_2$ | CH$_3$ | CH$_3$ | | |
| 1.246 | S(O)CF$_3$ | CH$_2$(CH$_2$)$_4$CH$_3$ | CH$_3$ | CH$_3$ | | |
| 1.247 | S(O)CF$_3$ | CH$_2$(CH$_2$)$_2$SCH$_3$ | CH$_3$ | CH$_3$ | | |
| 1.248 | S(O)CF$_3$ | CH$_2$C$_6$H$_5$ | CH$_3$ | CH$_3$ | | |
| 1.249 | S(O)CF$_3$ | CH$_2$-3-pyridyl | CH$_3$ | CH$_3$ | | |
| 1.250 | S(O)CF$_3$ | 5-CH$_3$-furfur-2-yl | CH$_3$ | CH$_3$ | | |
| 1.251 | S(O)CF$_3$ | CH$_2$-thiophen-2-yl | CH$_3$ | CH$_3$ | | |
| 1.252 | S(O)CF$_3$ | CH$_2$CH$_2$C$_6$H$_5$ | CH$_3$ | CH$_3$ | | |
| 1.253 | S(O)CF$_3$ | CH$_2$CH$_2$-3-pyridyl | CH$_3$ | CH$_3$ | | |
| 1.254 | S(O)CF$_3$ | CH$_2$(CH$_2$)$_2$—N-imidazolyl | CH$_3$ | CH$_3$ | | |
| 1.255 | S(O)CF$_3$ | CH$_2$CH$_3$ | CH$_2$CH$_3$ | H | 164 | 0.91 |
| 1.256 | S(O)CF$_3$ | CH$_2$CH$_3$ | CH$_2$CH$_3$ | CH$_3$ | | |
| 1.257 | S(O)CF$_3$ | —CH$_2$(CH$_2$)$_2$CH$_2$— | | H | | |
| 1.258 | S(O)CF$_3$ | —CH$_2$(CH$_2$)$_3$CH$_2$— | | H | | |
| 1.259 | S(O)CF$_3$ | —CH$_2$CH$_2$OCH$_2$CH$_2$— | | H | | |
| 1.260 | S(O)CF$_3$ | —CH$_2$CH$_2$N(CH$_3$)CH$_2$CH$_2$— | | H | | |
| 1.261 | S(O)CF$_3$ | —CH$_2$(CH$_2$)$_2$CH$_2$— | | CH$_3$ | | |
| 1.262 | S(O)CF$_3$ | —CH$_2$(CH$_2$)$_3$CH$_2$— | | CH$_3$ | | |
| 1.263 | S(O)CF$_3$ | —CH$_2$CH$_2$OCH$_2$CH$_2$— | | CH$_3$ | | |
| 1.264 | S(O)CF$_3$ | —CH$_2$CH$_2$N(CH$_3$)CH$_2$CH$_2$— | | CH$_3$ | | |
| 1.265 | S(O)$_2$CF$_3$ | cyclopropyl | H | H | | |
| 1.266 | S(O)$_2$CF$_3$ | CH$_2$CH═CH | H | H | | |
| 1.267 | S(O)$_2$CF$_3$ | CH$_2$CH═CH$_2$ | H | H | | |
| 1.268 | S(O)$_2$CF$_3$ | H | H | H | 217 | 0.90 |
| 1.269 | S(O)$_2$CF$_3$ | CH$_3$ | H | H | | |
| 1.270 | S(O)$_2$CF$_3$ | CH$_2$CH$_3$ | H | H | | |
| 1.271 | S(O)$_2$CF$_3$ | CH$_2$CH$_2$CH$_3$ | H | H | | |
| 1.272 | S(O)$_2$CF$_3$ | CH(CH$_3$)$_2$ | H | H | | |
| 1.273 | S(O)$_2$CF$_3$ | CH$_2$(CH$_2$)$_3$CH$_3$ | H | H | | |
| 1.274 | S(O)$_2$CF$_3$ | cyclohexyl | H | H | | |
| 1.275 | S(O)$_2$CF$_3$ | CH$_2$CH$_2$OCH$_3$ | H | H | | |
| 1.276 | S(O)$_2$CF$_3$ | 2-tetrahydrofurfuryl | H | H | | |
| 1.277 | S(O)$_2$CF$_3$ | 2-furfuryl | H | H | | |
| 1.278 | S(O)$_2$CF$_3$ | CH$_2$CN | H | H | | |
| 1.279 | S(O)$_2$CF$_3$ | CH$_2$CH$_2$CN | H | H | | |
| 1.280 | S(O)$_2$CF$_3$ | CH$_2$-cyclopropyl | H | H | | |

TABLE 1-continued

Compounds of formula (Ia)

(Ia)

| Cpd | R² | R⁶ | R⁷ | R¹⁰ | mp (° C.) | RF |
|---|---|---|---|---|---|---|
| 1.281 | S(O)₂CF₃ | CH₂CH₂CH(CH₃)₂ | H | H | | |
| 1.282 | S(O)₂CF₃ | CH₂CH₂N(CH₃)₂ | H | H | | |
| 1.283 | S(O)₂CF₃ | CH₂CH₂CH₂OCH₃ | H | H | | |
| 1.284 | S(O)₂CF₃ | CH₂CH₂SCH₃ | H | H | | |
| 1.285 | S(O)₂CF₃ | CH₂CF₃ | H | H | | |
| 1.286 | S(O)₂CF₃ | CH₂(CH₂)₂CH=CH₂ | H | H | | |
| 1.287 | S(O)₂CF₃ | CH₂(CH₂)₄CH₃ | H | H | | |
| 1.288 | S(O)₂CF₃ | CH₂(CH₂)₂SCH₃ | H | H | | |
| 1.289 | S(O)₂CF₃ | CH₂C₆H₅ | H | H | | |
| 1.290 | S(O)₂CF₃ | CH₂-3-pyridyl | H | H | | |
| 1.291 | S(O)₂CF₃ | 5-CH₃-furfur-2-yl | H | H | | |
| 1.292 | S(O)₂CF₃ | CH₂-thiophen-2-yl | H | H | | |
| 1.293 | S(O)₂CF₃ | CH₂CH₂C₆H₅ | H | H | | |
| 1.294 | S(O)₂CF₃ | CH₂CH₂-3-pyridyl | H | H | | |
| 1.295 | S(O)₂CF₃ | CH₂(CH₂)₂—N-imidazolyl | H | H | | |
| 1.296 | S(O)₂CF₃ | cyclopropyl | CH₃ | H | | |
| 1.297 | S(O)₂CF₃ | CH₂CH≡CH | CH₃ | H | | |
| 1.298 | S(O)₂CF₃ | CH₂CH=CH₂ | CH₃ | H | | |
| 1.299 | S(O)₂CF₃ | CH₃ | CH₃ | H | | |
| 1.300 | S(O)₂CF₃ | CH₂CH₃ | CH₃ | H | | |
| 1.301 | S(O)₂CF₃ | CH₂CH₂CH₃ | CH₃ | H | | |
| 1.302 | S(O)₂CF₃ | CH(CH₃)₂ | CH₃ | H | | |
| 1.303 | S(O)₂CF₃ | CH₂(CH₂)₃CH₃ | CH₃ | H | | |
| 1.304 | S(O)₂CF₃ | cyclohexyl | CH₃ | H | | |
| 1.305 | S(O)₂CF₃ | CH₂CH₂OCH₃ | CH₃ | H | | |
| 1.306 | S(O)₂CF₃ | 2-tetrahydrofurfuryl | CH₃ | H | | |
| 1.307 | S(O)₂CF₃ | 2-furfuryl | CH₃ | H | | |
| 1.308 | S(O)₂CF₃ | CH₂CN | CH₃ | H | | |
| 1.309 | S(O)₂CF₃ | CH₂CH₂CN | CH₃ | H | | |
| 1.310 | S(O)₂CF₃ | CH₂-cyclopropyl | CH₃ | H | | |
| 1.311 | S(O)₂CF₃ | CH₂CH₂CH(CH₃)₂ | CH₃ | H | | |
| 1.312 | S(O)₂CF₃ | CH₂CH₂N(CH₃)₂ | CH₃ | H | | |
| 1.313 | S(O)₂CF₃ | CH₂CH₂CH₂OCH₃ | CH₃ | H | | |
| 1.314 | S(O)₂CF₃ | CH₂CH₂SCH₃ | CH₃ | H | | |
| 1.315 | S(O)₂CF₃ | CH₂CF₃ | CH₃ | H | | |
| 1.316 | S(O)₂CF₃ | CH₂(CH₂)₂CH=CH₂ | CH₃ | H | | |
| 1.317 | S(O)₂CF₃ | CH₂(CH₂)₄CH₃ | CH₃ | H | | |
| 1.318 | S(O)₂CF₃ | CH₂(CH₂)₂SCH₃ | CH₃ | H | | |
| 1.319 | S(O)₂CF₃ | CH₂C₆H₅ | CH₃ | H | | |
| 1.320 | S(O)₂CF₃ | CH₂-3-pyridyl | CH₃ | H | | |
| 1.321 | S(O)₂CF₃ | 5-CH₃-furfur-2-yl | CH₃ | H | | |
| 1.322 | S(O)₂CF₃ | CH₂-thiophen-2-yl | CH₃ | H | | |
| 1.323 | S(O)₂CF₃ | CH₂CH₂C₆H₅ | CH₃ | H | | |
| 1.324 | S(O)₂CF₃ | CH₂CH₂-3-pyridyl | CH₃ | H | | |
| 1.325 | S(O)₂CF₃ | CH₂(CH₂)₂—N-imidazolyl | CH₃ | H | | |
| 1.326 | S(O)₂CF₃ | cyclopropyl | H | CH₃ | | |
| 1.327 | S(O)₂CF₃ | CH₂CH≡CH | H | CH₃ | | |
| 1.328 | S(O)₂CF₃ | CH₂CH=CH₂ | H | CH₃ | | |
| 1.329 | S(O)₂CF₃ | H | H | CH₃ | 219 | 0.90 |
| 1.330 | S(O)₂CF₃ | CH₃ | H | CH₃ | | |
| 1.331 | S(O)₂CF₃ | CH₂CH₃ | H | CH₃ | | |
| 1.332 | S(O)₂CF₃ | CH₂CH₂CH₃ | H | CH₃ | | |
| 1.333 | S(O)₂CF₃ | CH(CH₃)₂ | H | CH₃ | | |
| 1.334 | S(O)₂CF₃ | CH₂(CH₂)₃CH₃ | H | CH₃ | | |
| 1.335 | S(O)₂CF₃ | cyclohexyl | H | CH₃ | | |
| 1.336 | S(O)₂CF₃ | CH₂CH₂OCH₃ | H | CH₃ | | |
| 1.337 | S(O)₂CF₃ | 2-tetrahydrofurfuryl | H | CH₃ | | |

TABLE 1-continued

Compounds of formula (Ia)

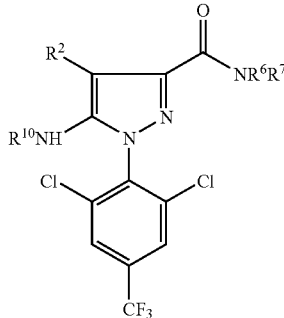

(Ia)

| Cpd | R² | R⁶ | R⁷ | R¹⁰ | mp (° C.) | RF |
|---|---|---|---|---|---|---|
| 1.338 | S(O)₂CF₃ | 2-furfuryl | H | CH₃ | | |
| 1.339 | S(O)₂CF₃ | CH₂CN | H | CH₃ | | |
| 1.340 | S(O)₂CF₃ | CH₂CH₂CN | H | CH₃ | | |
| 1.341 | S(O)₂CF₃ | CH₂-cyclopropyl | H | CH₃ | | |
| 1.342 | S(O)₂CF₃ | CH₂CH₂CH(CH₃)₂ | H | CH₃ | | |
| 1.343 | S(O)₂CF₃ | CH₂CH₂N(CH₃)₂ | H | CH₃ | | |
| 1.344 | S(O)₂CF₃ | CH₂CH₂CH₂OCH₃ | H | CH₃ | | |
| 1.345 | S(O)₂CF₃ | CH₂CH₂SCH₃ | H | CH₃ | | |
| 1.346 | S(O)₂CF₃ | CH₂CF₃ | H | CH₃ | | |
| 1.347 | S(O)₂CF₃ | CH₂(CH₂)₂CH=CH₂ | H | CH₃ | | |
| 1.348 | S(O)₂CF₃ | CH₂(CH₂)₄CH₃ | H | CH₃ | | |
| 1.349 | S(O)₂CF₃ | CH₂(CH₂)₂SCH₃ | H | CH₃ | | |
| 1.350 | S(O)₂CF₃ | CH₂C₆H₅ | H | CH₃ | | |
| 1.351 | S(O)₂CF₃ | CH₂-3-pyridyl | H | CH₃ | | |
| 1.352 | S(O)₂CF₃ | 5-CH₃-furfur-2-yl | H | CH₃ | | |
| 1.353 | S(O)₂CF₃ | CH₂-thiophen-2-yl | H | CH₃ | | |
| 1.354 | S(O)₂CF₃ | CH₂CH₂C₆H₅ | H | CH₃ | | |
| 1.355 | S(O)₂CF₃ | CH₂CH₂-3-pyridyl | H | CH₃ | | |
| 1.356 | S(O)₂CF₃ | CH₂(CH₂)₂—N-imidazolyl | H | CH₃ | | |
| 1.357 | S(O)₂CF₃ | cyclopropyl | CH₃ | CH₃ | | |
| 1.358 | S(O)₂CF₃ | CH₂CH≡CH | CH₃ | CH₃ | | |
| 1.359 | S(O)₂CF₃ | CH₂CH=CH₂ | CH₃ | CH₃ | | |
| 1.360 | S(O)₂CF₃ | CH₃ | CH₃ | CH₃ | | |
| 1.361 | S(O)₂CF₃ | CH₂CH₃ | CH₃ | CH₃ | | |
| 1.362 | S(O)₂CF₃ | CH₂CH₂CH₃ | CH₃ | CH₃ | | |
| 1.363 | S(O)₂CF₃ | CH(CH₃)₂ | CH₃ | CH₃ | | |
| 1.364 | S(O)₂CF₃ | CH₂(CH₂)₃CH₃ | CH₃ | CH₃ | | |
| 1.365 | S(O)₂CF₃ | cyclohexyl | CH₃ | CH₃ | | |
| 1.366 | S(O)₂CF₃ | CH₂CH₂OCH₃ | CH₃ | CH₃ | | |
| 1.367 | S(O)₂CF₃ | 2-tetrahydrofurfuryl | CH₃ | CH₃ | | |
| 1.368 | S(O)₂CF₃ | 2-furfuryl | CH₃ | CH₃ | | |
| 1.369 | S(O)₂CF₃ | CH₂CN | CH₃ | CH₃ | | |
| 1.370 | S(O)₂CF₃ | CH₂CH₂CN | CH₃ | CH₃ | | |
| 1.371 | S(O)₂CF₃ | CH₂-cyclopropyl | CH₃ | CH₃ | | |
| 1.372 | S(O)₂CF₃ | CH₂CH₂CH(CH₃)₂ | CH₃ | CH₃ | | |
| 1.373 | S(O)₂CF₃ | CH₂CH₂N(CH₃)₂ | CH₃ | CH₃ | | |
| 1.374 | S(O)₂CF₃ | CH₂CH₂CH₂OCH₃ | CH₃ | CH₃ | | |
| 1.375 | S(O)₂CF₃ | CH₂CH₂SCH₃ | CH₃ | CH₃ | | |
| 1.376 | S(O)₂CF₃ | CH₂CF₃ | CH₃ | CH₃ | | |
| 1.377 | S(O)₂CF₃ | CH₂(CH₂)₂CH=CH₂ | CH₃ | CH₃ | | |
| 1.378 | S(O)₂CF₃ | CH₂(CH₂)₄CH₃ | CH₃ | CH₃ | | |
| 1.379 | S(O)₂CF₃ | CH₂(CH₂)₂SCH₃ | CH₃ | CH₃ | | |
| 1.380 | S(O)₂CF₃ | CH₂C₆H₅ | CH₃ | CH₃ | | |
| 1.381 | S(O)₂CF₃ | CH₂-3-pyridyl | CH₃ | CH₃ | | |
| 1.382 | S(O)₂CF₃ | 5-CH₃-furfur-2-yl | CH₃ | CH₃ | | |
| 1.383 | S(O)₂CF₃ | CH₂-thiophen-2-yl | CH₃ | CH₃ | | |
| 1.384 | S(O)₂CF₃ | CH₂CH₂C₆H₅ | CH₃ | CH₃ | | |
| 1.385 | S(O)₂CF₃ | CH₂CH₂-3-pyridyl | CH₃ | CH₃ | | |
| 1.386 | S(O)₂CF₃ | CH₂(CH₂)₂—N-imidazolyl | CH₃ | CH₃ | | |
| 1.387 | S(O)₂CF₃ | CH₂CH₃ | CH₂CH₃ | H | | |
| 1.388 | S(O)₂CF₃ | CH₂CH₃ | CH₂CH₃ | CH₃ | | |
| 1.389 | S(O)₂CF₃ | —CH₂(CH₂)₂CH₂— | | H | | |
| 1.390 | S(O)₂CF₃ | —CH₂(CH₂)₃CH₂— | | H | | |
| 1.391 | S(O)₂CF₃ | —CH₂CH₂OCH₂CH₂— | | H | | |
| 1.392 | S(O)₂CF₃ | —CH₂CH₂N(CH₃)CH₂CH₂— | | H | | |
| 1.393 | S(O)₂CF₃ | —CH₂(CH₂)₂CH₂— | | CH₃ | | |
| 1.394 | S(O)₂CF₃ | —CH₂(CH₂)₃CH₂— | | CH₃ | | |

TABLE 1-continued

Compounds of formula (Ia)

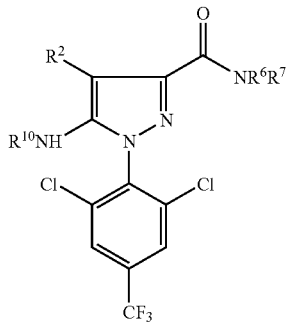

(Ia)

| Cpd | $R^2$ | $R^6$ | $R^7$ | $R^{10}$ | mp (° C.) | RF |
|---|---|---|---|---|---|---|
| 1.395 | S(O)$_2$CF$_3$ | —CH$_2$CH$_2$OCH$_2$CH$_2$— | | CH$_3$ | | |
| 1.396 | S(O)$_2$CF$_3$ | —CH$_2$CH$_2$N(CH$_3$)CH$_2$CH$_2$— | | CH$_3$ | | |
| 1.397 | H | cyclopropyl | H | H | | |
| 1.398 | H | CH$_2$CH=CH | H | H | | |
| 1.399 | H | CH$_2$CH=CH$_2$ | H | H | oil | 0.84 |
| 1.400 | H | H | H | H | foam | 0.81 |
| 1.401 | H | CH$_3$ | H | H | | |
| 1.402 | H | CH$_2$CH$_3$ | H | H | | |
| 1.403 | H | CH$_2$CH$_2$CH$_3$ | H | H | | |
| 1.404 | H | CH(CH$_3$)$_2$ | H | H | | |
| 1.405 | H | CH$_2$(CH$_2$)$_3$CH$_3$ | H | H | | |
| 1.406 | H | cyclohexyl | H | H | | |
| 1.407 | H | CH$_2$CH$_2$OCH$_3$ | H | H | | |
| 1.408 | H | 2-tetrahydrofurfuryl | H | H | | |
| 1.409 | H | 2-furfuryl | H | H | | |
| 1.410 | H | CH$_2$CN | H | H | | |
| 1.411 | H | CH$_2$CH$_2$CN | H | H | | |
| 1.412 | H | CH$_2$-cyclopropyl | H | H | | |
| 1.413 | H | CH$_2$CH$_2$CH(CH$_3$)$_2$ | H | H | | |
| 1.414 | H | CH$_2$CH$_2$N(CH$_3$)$_2$ | H | H | | |
| 1.415 | H | CH$_2$CH$_2$CH$_2$OCH$_3$ | H | H | | |
| 1.416 | H | CH$_2$CH$_2$SCH$_3$ | H | H | | |
| 1.417 | H | CH$_2$CF$_3$ | H | H | | |
| 1.418 | H | CH$_2$(CH$_2$)$_2$CH=CH$_2$ | H | H | | |
| 1.419 | H | CH$_2$(CH$_2$)$_4$CH$_3$ | H | H | | |
| 1.420 | H | CH$_2$(CH$_2$)$_2$SCH$_3$ | H | H | | |
| 1.421 | H | CH$_2$C$_6$H$_5$ | H | H | | |
| 1.422 | H | CH$_2$-3-pyridyl | H | H | | |
| 1.423 | H | 5-CH$_3$-furfur-2-yl | H | H | | |
| 1.424 | H | CH$_2$-thiophen-2-yl | H | H | | |
| 1.425 | H | CH$_2$CH$_2$C$_6$H$_5$ | H | H | | |
| 1.426 | H | CH$_2$CH$_2$-3-pyridyl | H | H | | |
| 1.427 | H | CH$_2$(CH$_2$)$_2$—N-imidazolyl | H | H | | |
| 1.428 | H | cyclopropyl | CH$_3$ | H | | |
| 1.429 | H | CH$_2$CH=CH | CH$_3$ | H | | |
| 1.430 | H | CH$_2$CH=CH$_2$ | CH$_3$ | H | | |
| 1.431 | H | CH$_3$ | CH$_3$ | H | | |
| 1.432 | H | CH$_2$CH$_3$ | CH$_3$ | H | | |
| 1.433 | H | CH$_2$CH$_2$CH$_3$ | CH$_3$ | H | | |
| 1.434 | H | CH(CH$_3$)$_2$ | CH$_3$ | H | | |
| 1.435 | H | CH$_2$(CH$_2$)$_3$CH$_3$ | CH$_3$ | H | | |
| 1.436 | H | cyclohexyl | CH$_3$ | H | | |
| 1.437 | H | CH$_2$CH$_2$OCH$_3$ | CH$_3$ | H | | |
| 1.438 | H | 2-tetrahydrofurfuryl | CH$_3$ | H | | |
| 1.439 | H | 2-furfuryl | CH$_3$ | H | | |
| 1.440 | H | CH$_2$CN | CH$_3$ | H | | |
| 1.441 | H | CH$_2$CH$_2$CN | CH$_3$ | H | | |
| 1.442 | H | CH$_2$-cyclopropyl | CH$_3$ | H | | |
| 1.443 | H | CH$_2$CH$_2$CH(CH$_3$)$_2$ | CH$_3$ | H | | |
| 1.444 | H | CH$_2$CH$_2$N(CH$_3$)$_2$ | CH$_3$ | H | | |
| 1.445 | H | CH$_2$CH$_2$CH$_2$OCH$_3$ | CH$_3$ | H | | |
| 1.446 | H | CH$_2$CH$_2$SCH$_3$ | CH$_3$ | H | | |
| 1.447 | H | CH$_2$CF$_3$ | CH$_3$ | H | | |
| 1.448 | H | CH$_2$(CH$_2$)$_2$CH=CH$_2$ | CH$_3$ | H | | |
| 1.449 | H | CH$_2$(CH$_2$)$_4$CH$_3$ | CH$_3$ | H | | |
| 1.450 | H | CH$_2$(CH$_2$)$_2$SCH$_3$ | CH$_3$ | H | | |
| 1.451 | H | CH$_2$C$_6$H$_5$ | CH$_3$ | H | | |

TABLE 1-continued

Compounds of formula (Ia)

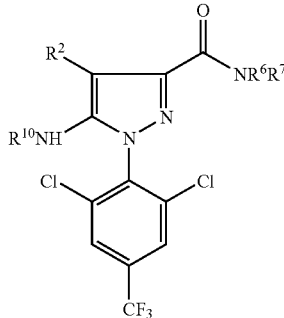

(Ia)

| Cpd | $R^2$ | $R^6$ | $R^7$ | $R^{10}$ | mp (° C.) | RF |
|---|---|---|---|---|---|---|
| 1.452 | H | $CH_2$-3-pyridyl | $CH_3$ | H | | |
| 1.453 | H | 5-$CH_3$-furfur-2-yl | $CH_3$ | H | | |
| 1.454 | H | $CH_2$-thiophen-2-yl | $CH_3$ | H | | |
| 1.455 | H | $CH_2CH_2C_6H_5$ | $CH_3$ | H | | |
| 1.456 | H | $CH_2CH_2$-3-pyridyl | $CH_3$ | H | | |
| 1.457 | H | $CH_2(CH_2)_2$—N-imidazolyl | $CH_3$ | H | | |
| 1.458 | H | cyclopropyl | H | $CH_3$ | | |
| 1.459 | H | $CH_2CH\!\!=\!\!CH$ | H | $CH_3$ | | |
| 1.460 | H | $CH_2CH\!\!=\!\!CH_2$ | H | $CH_3$ | | |
| 1.461 | H | H | H | $CH_3$ | 80 | 0.68 |
| 1.462 | H | $CH_3$ | H | $CH_3$ | | |
| 1.463 | H | $CH_2CH_3$ | H | $CH_3$ | | |
| 1.464 | H | $CH_2CH_2CH_3$ | H | $CH_3$ | | |
| 1.465 | H | $CH(CH_3)_2$ | H | $CH_3$ | | |
| 1.466 | H | $CH_2(CH_2)_3CH_3$ | H | $CH_3$ | | |
| 1.467 | H | cyclohexyl | H | $CH_3$ | | |
| 1.468 | H | $CH_2CH_2OCH_3$ | H | $CH_3$ | | |
| 1.469 | H | 2-tetrahydrofurfuryl | H | $CH_3$ | | |
| 1.470 | H | 2-furfuryl | H | $CH_3$ | | |
| 1.471 | H | $CH_2CN$ | H | $CH_3$ | | |
| 1.472 | H | $CH_2CH_2CN$ | H | $CH_3$ | | |
| 1.473 | H | $CH_2$-cyclopropyl | H | $CH_3$ | | |
| 1.474 | H | $CH_2CH_2CH(CH_3)_2$ | H | $CH_3$ | | |
| 1.475 | H | $CH_2CH_2N(CH_3)_2$ | H | $CH_3$ | | |
| 1.476 | H | $CH_2CH_2CH_2OCH_3$ | H | $CH_3$ | | |
| 1.477 | H | $CH_2CH_2SCH_3$ | H | $CH_3$ | | |
| 1.478 | H | $CH_2CF_3$ | H | $CH_3$ | | |
| 1.479 | H | $CH_2(CH_2)_2CH\!\!=\!\!CH_2$ | H | $CH_3$ | | |
| 1.480 | H | $CH_2(CH_2)_4CH_3$ | H | $CH_3$ | | |
| 1.481 | H | $CH_2(CH_2)_2SCH_3$ | H | $CH_3$ | | |
| 1.482 | H | $CH_2C_6H_5$ | H | $CH_3$ | | |
| 1.483 | H | $CH_2$-3-pyridyl | H | $CH_3$ | | |
| 1.484 | H | 5-$CH_3$-furfur-2-yl | H | $CH_3$ | | |
| 1.485 | H | $CH_2$-thiophen-2-yl | H | $CH_3$ | | |
| 1.486 | H | $CH_2CH_2C_6H_5$ | H | $CH_3$ | | |
| 1.487 | H | $CH_2CH_2$-3-pyridyl | H | $CH_3$ | | |
| 1.488 | H | $CH_2(CH_2)_2$—N-imidazolyl | H | $CH_3$ | | |
| 1.489 | H | cyclopropyl | $CH_3$ | $CH_3$ | | |
| 1.490 | H | $CH_2CH\!\!=\!\!CH$ | $CH_3$ | $CH_3$ | | |
| 1.491 | H | $CH_2CH\!\!=\!\!CH_2$ | $CH_3$ | $CH_3$ | | |
| 1.492 | H | $CH_3$ | $CH_3$ | $CH_3$ | | |
| 1.493 | H | $CH_2CH_3$ | $CH_3$ | $CH_3$ | | |
| 1.494 | H | $CH_2CH_2CH_3$ | $CH_3$ | $CH_3$ | | |
| 1.495 | H | $CH(CH_3)_2$ | $CH_3$ | $CH_3$ | | |
| 1.496 | H | $CH_2(CH_2)_3CH_3$ | $CH_3$ | $CH_3$ | | |
| 1.497 | H | cyclohexyl | $CH_3$ | $CH_3$ | | |
| 1.498 | H | $CH_2CH_2OCH_3$ | $CH_3$ | $CH_3$ | | |
| 1.499 | H | 2-tetrahydrofurfuryl | $CH_3$ | $CH_3$ | | |
| 1.500 | H | 2-furfuryl | $CH_3$ | $CH_3$ | | |
| 1.501 | H | $CH_2CN$ | $CH_3$ | $CH_3$ | | |
| 1.502 | H | $CH_2CH_2CN$ | $CH_3$ | $CH_3$ | | |
| 1.503 | H | $CH_2$-cyclopropyl | $CH_3$ | $CH_3$ | | |
| 1.504 | H | $CH_2CH_2CH(CH_3)_2$ | $CH_3$ | $CH_3$ | | |
| 1.505 | H | $CH_2CH_2N(CH_3)_2$ | $CH_3$ | $CH_3$ | | |
| 1.506 | H | $CH_2CH_2CH_2OCH_3$ | $CH_3$ | $CH_3$ | | |
| 1.507 | H | $CH_2CH_2SCH_3$ | $CH_3$ | $CH_3$ | | |
| 1.508 | H | $CH_2CF_3$ | $CH_3$ | $CH_3$ | | |

TABLE 1-continued

Compounds of formula (Ia)

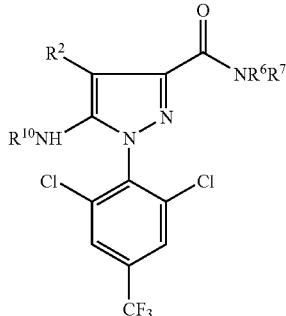

(Ia)

| Cpd | R² | R⁶ | R⁷ | R¹⁰ | mp (° C.) | RF |
|---|---|---|---|---|---|---|
| 1.509 | H | CH₂(CH₂)₂CH=CH₂ | CH₃ | CH₃ | | |
| 1.510 | H | CH₂(CH₂)₄CH₃ | CH₃ | CH₃ | | |
| 1.511 | H | CH₂(CH₂)₂SCH₃ | CH₃ | CH₃ | | |
| 1.512 | H | CH₂C₆H₅ | CH₃ | CH₃ | | |
| 1.513 | H | CH₂-3-pyridyl | CH₃ | CH₃ | | |
| 1.514 | H | 5-CH₃-furfur-2-yl | CH₃ | CH₃ | | |
| 1.515 | H | CH₂-thiophen-2-yl | CH₃ | CH₃ | | |
| 1.516 | H | CH₂CH₂C₆H₅ | CH₃ | CH₃ | | |
| 1.517 | H | CH₂CH₂-3-pyridyl | CH₃ | CH₃ | | |
| 1.518 | H | CH₂(CH₂)₂—N-imidazolyl | CH₃ | CH₃ | | |
| 1.519 | H | CH₂CH₃ | CH₂CH₃ | H | | |
| 1.520 | H | CH₂CH₃ | CH₂CH₃ | CH₃ | | |
| 1.521 | H | —CH₂(CH₂)₂CH₂— | | H | | |
| 1.522 | H | —CH₂(CH₂)₃CH₂— | | H | | |
| 1.523 | H | —CH₂CH₂OCH₂CH₂— | | H | | |
| 1.524 | H | —CH₂CH₂N(CH₃)CH₂CH₂— | | H | | |
| 1.525 | H | —CH₂(CH₂)₂CH₂— | | CH₃ | | |
| 1.526 | H | —CH₂(CH₂)₃CH₂— | | CH₃ | | |
| 1.527 | H | —CH₂CH₂OCH₂CH₂— | | CH₃ | | |
| 1.528 | H | —CH₂CH₂N(CH₃)CH₂CH₂— | | CH₃ | | |
| 1.529 | SCH₂CH₃ | cyclopropyl | H | H | | |
| 1.530 | SCH₂CH₃ | CH₂CH=CH | H | H | | |
| 1.531 | SCH₂CH₃ | CH₂CH=CH₂ | H | H | | |
| 1.532 | SCH₂CH₃ | H | H | H | 189 | 0.81 |
| 1.533 | SCH₂CH₃ | CH₃ | H | H | | |
| 1.534 | SCH₂CH₃ | CH₂CH₃ | H | H | | |
| 1.535 | SCH₂CH₃ | CH₂CH₂CH₃ | H | H | | |
| 1.536 | SCH₂CH₃ | CH(CH₃)₂ | H | H | | |
| 1.537 | SCH₂CH₃ | CH₂(CH₂)₃CH₃ | H | H | | |
| 1.538 | SCH₂CH₃ | cyclohexyl | H | H | | |
| 1.539 | SCH₂CH₃ | CH₂CH₂OCH₃ | H | H | | |
| 1.540 | SCH₂CH₃ | 2-tetrahydrofurfuryl | H | H | | |
| 1.541 | SCH₂CH₃ | 2-furfuryl | H | H | | |
| 1.542 | SCH₂CH₃ | CH₂CN | H | H | | |
| 1.543 | SCH₂CH₃ | CH₂CH₂CN | H | H | | |
| 1.544 | SCH₂CH₃ | CH₂-cyclopropyl | H | H | | |
| 1.545 | SCH₂CH₃ | CH₂CH₂CH(CH₃)₂ | H | H | | |
| 1.546 | SCH₂CH₃ | CH₂CH₂N(CH₃)₂ | H | H | | |
| 1.547 | SCH₂CH₃ | CH₂CH₂CH₂OCH₃ | H | H | | |
| 1.548 | SCH₂CH₃ | CH₂CH₂SCH₃ | H | H | | |
| 1.549 | SCH₂CH₃ | CH₂CF₃ | H | H | | |
| 1.550 | SCH₂CH₃ | CH₂(CH₂)₂CH=CH₂ | H | H | | |
| 1.551 | SCH₂CH₃ | CH₂(CH₂)₄CH₃ | H | H | | |
| 1.552 | SCH₂CH₃ | CH₂(CH₂)₂SCH₃ | H | H | | |
| 1.553 | SCH₂CH₃ | CH₂C₆H₅ | H | H | | |
| 1.554 | SCH₂CH₃ | CH₂-3-pyridyl | H | H | | |
| 1.555 | SCH₂CH₃ | 5-CH₃-furfur-2-yl | H | H | | |
| 1.556 | SCH₂CH₃ | CH₂-thiophen-2-yl | H | H | | |
| 1.557 | SCH₂CH₃ | CH₂CH₂C₆H₅ | H | H | | |
| 1.558 | SCH₂CH₃ | CH₂CH₂-3-pyridyl | H | H | | |
| 1.559 | SCH₂CH₃ | CH₂(CH₂)₂—N-imidazolyl | H | H | | |
| 1.560 | SCH₂CH₃ | cyclopropyl | CH₃ | H | | |
| 1.561 | SCH₂CH₃ | CH₂CH=CH | CH₃ | H | | |
| 1.562 | SCH₂CH₃ | CH₂CH=CH₂ | CH₃ | H | | |
| 1.563 | SCH₂CH₃ | CH₃ | CH₃ | H | | |
| 1.564 | SCH₂CH₃ | CH₂CH₃ | CH₃ | H | | |
| 1.565 | SCH₂CH₃ | CH₂CH₂CH₃ | CH₃ | H | | |

TABLE 1-continued

Compounds of formula (Ia)

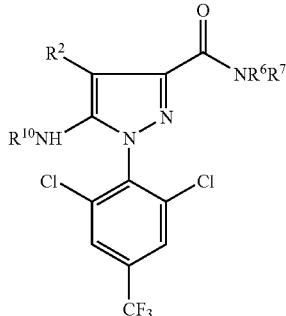

| Cpd | $R^2$ | $R^6$ | $R^7$ | $R^{10}$ | mp (° C.) | RF |
|---|---|---|---|---|---|---|
| 1.566 | $SCH_2CH_3$ | $CH(CH_3)_2$ | $CH_3$ | H | | |
| 1.567 | $SCH_2CH_3$ | $CH_2(CH_2)_3CH_3$ | $CH_3$ | H | | |
| 1.568 | $SCH_2CH_3$ | cyclohexyl | $CH_3$ | H | | |
| 1.569 | $SCH_2CH_3$ | $CH_2CH_2OCH_3$ | $CH_3$ | H | | |
| 1.570 | $SCH_2CH_3$ | 2-tetrahydrofurfuryl | $CH_3$ | H | | |
| 1.571 | $SCH_2CH_3$ | 2-furfuryl | $CH_3$ | H | | |
| 1.572 | $SCH_2CH_3$ | $CH_2CN$ | $CH_3$ | H | | |
| 1.573 | $SCH_2CH_3$ | $CH_2CH_2CN$ | $CH_3$ | H | | |
| 1.574 | $SCH_2CH_3$ | $CH_2$-cyclopropyl | $CH_3$ | H | | |
| 1.575 | $SCH_2CH_3$ | $CH_2CH_2CH(CH_3)_2$ | $CH_3$ | H | | |
| 1.576 | $SCH_2CH_3$ | $CH_2CH_2N(CH_3)_2$ | $CH_3$ | H | | |
| 1.577 | $SCH_2CH_3$ | $CH_2CH_2CH_2OCH_3$ | $CH_3$ | H | | |
| 1.578 | $SCH_2CH_3$ | $CH_2CH_2SCH_3$ | $CH_3$ | H | | |
| 1.579 | $SCH_2CH_3$ | $CH_2CF_3$ | $CH_3$ | H | | |
| 1.580 | $SCH_2CH_3$ | $CH_2(CH_2)_2CH=CH_2$ | $CH_3$ | H | | |
| 1.581 | $SCH_2CH_3$ | $CH_2(CH_2)_4CH_3$ | $CH_3$ | H | | |
| 1.582 | $SCH_2CH_3$ | $CH_2(CH_2)_2SCH_3$ | $CH_3$ | H | | |
| 1.583 | $SCH_2CH_3$ | $CH_2C_6H_5$ | $CH_3$ | H | | |
| 1.584 | $SCH_2CH_3$ | $CH_2$-3-pyridyl | $CH_3$ | H | | |
| 1.585 | $SCH_2CH_3$ | 5-$CH_3$-furfur-2-yl | $CH_3$ | H | | |
| 1.586 | $SCH_2CH_3$ | $CH_2$-thiophen-2-yl | $CH_3$ | H | | |
| 1.587 | $SCH_2CH_3$ | $CH_2CH_2C_6H_5$ | $CH_3$ | H | | |
| 1.588 | $SCH_2CH_3$ | $CH_2CH_2$-3-pyridyl | $CH_3$ | H | | |
| 1.589 | $SCH_2CH_3$ | $CH_2(CH_2)_2$—N-imidazolyl | $CH_3$ | H | | |
| 1.590 | $SCH_2CH_3$ | cyclopropyl | H | $CH_3$ | | |
| 1.591 | $SCH_2CH_3$ | $CH_2CH=CH$ | H | $CH_3$ | | |
| 1.592 | $SCH_2CH_3$ | $CH_2CH=CH_2$ | H | $CH_3$ | | |
| 1.593 | $SCH_2CH_3$ | H | H | $CH_3$ | | |
| 1.594 | $SCH_2CH_3$ | $CH_3$ | H | $CH_3$ | | |
| 1.595 | $SCH_2CH_3$ | $CH_2CH_3$ | H | $CH_3$ | | |
| 1.596 | $SCH_2CH_3$ | $CH_2CH_2CH_3$ | H | $CH_3$ | | |
| 1.597 | $SCH_2CH_3$ | $CH(CH_3)_2$ | H | $CH_3$ | | |
| 1.598 | $SCH_2CH_3$ | $CH_2(CH_2)_3CH_3$ | H | $CH_3$ | | |
| 1.599 | $SCH_2CH_3$ | cyclohexyl | H | $CH_3$ | | |
| 1.600 | $SCH_2CH_3$ | $CH_2CH_2OCH_3$ | H | $CH_3$ | | |
| 1.601 | $SCH_2CH_3$ | 2-tetrahydrofurfuryl | H | $CH_3$ | | |
| 1.602 | $SCH_2CH_3$ | 2-furfuryl | H | $CH_3$ | | |
| 1.603 | $SCH_2CH_3$ | $CH_2CN$ | H | $CH_3$ | | |
| 1.604 | $SCH_2CH_3$ | $CH_2CH_2CN$ | H | $CH_3$ | | |
| 1.605 | $SCH_2CH_3$ | $CH_2$-cyclopropyl | H | $CH_3$ | | |
| 1.606 | $SCH_2CH_3$ | $CH_2CH_2CH(CH_3)_2$ | H | $CH_3$ | | |
| 1.607 | $SCH_2CH_3$ | $CH_2CH_2N(CH_3)_2$ | H | $CH_3$ | | |
| 1.608 | $SCH_2CH_3$ | $CH_2CH_2CH_2OCH_3$ | H | $CH_3$ | | |
| 1.609 | $SCH_2CH_3$ | $CH_2CH_2SCH_3$ | H | $CH_3$ | | |
| 1.610 | $SCH_2CH_3$ | $CH_2CF_3$ | H | $CH_3$ | | |
| 1.611 | $SCH_2CH_3$ | $CH_2(CH_2)_2CH=CH_2$ | H | $CH_3$ | | |
| 1.612 | $SCH_2CH_3$ | $CH_2(CH_2)_4CH_3$ | H | $CH_3$ | | |
| 1.613 | $SCH_2CH_3$ | $CH_2(CH_2)_2SCH_3$ | H | $CH_3$ | | |
| 1.614 | $SCH_2CH_3$ | $CH_2C_6H_5$ | H | $CH_3$ | | |
| 1.615 | $SCH_2CH_3$ | $CH_2$-3-pyridyl | H | $CH_3$ | | |
| 1.616 | $SCH_2CH_3$ | 5-$CH_3$-furfur-2-yl | H | $CH_3$ | | |
| 1.617 | $SCH_2CH_3$ | $CH_2$-thiophen-2-yl | H | $CH_3$ | | |
| 1.618 | $SCH_2CH_3$ | $CH_2CH_2C_6H_5$ | H | $CH_3$ | | |
| 1.619 | $SCH_2CH_3$ | $CH_2CH_2$-3-pyridyl | H | $CH_3$ | | |
| 1.620 | $SCH_2CH_3$ | $CH_2(CH_2)_2$—N-imidazolyl | H | $CH_3$ | | |
| 1.621 | $SCH_2CH_3$ | cyclopropyl | $CH_3$ | $CH_3$ | | |
| 1.622 | $SCH_2CH_3$ | $CH_2CH=CH$ | $CH_3$ | $CH_3$ | | |

TABLE 1-continued

Compounds of formula (Ia)

(Ia)

| Cpd | R² | R⁶ | R⁷ | R¹⁰ | mp (° C.) | RF |
|---|---|---|---|---|---|---|
| 1.623 | SCH₂CH₃ | CH₂CH=CH₂ | CH₃ | CH₃ | | |
| 1.624 | SCH₂CH₃ | CH₃ | CH₃ | CH₃ | | |
| 1.625 | SCH₂CH₃ | CH₂CH₃ | CH₃ | CH₃ | | |
| 1.626 | SCH₂CH₃ | CH₂CH₂CH₃ | CH₃ | CH₃ | | |
| 1.627 | SCH₂CH₃ | CH(CH₃)₂ | CH₃ | CH₃ | | |
| 1.628 | SCH₂CH₃ | CH₂(CH₂)₃CH₃ | CH₃ | CH₃ | | |
| 1.629 | SCH₂CH₃ | cyclohexyl | CH₃ | CH₃ | | |
| 1.630 | SCH₂CH₃ | CH₂CH₂OCH₃ | CH₃ | CH₃ | | |
| 1.631 | SCH₂CH₃ | 2-tetrahydrofurfuryl | CH₃ | CH₃ | | |
| 1.632 | SCH₂CH₃ | 2-furfuryl | CH₃ | CH₃ | | |
| 1.633 | SCH₂CH₃ | CH₂CN | CH₃ | CH₃ | | |
| 1.634 | SCH₂CH₃ | CH₂CH₂CN | CH₃ | CH₃ | | |
| 1.635 | SCH₂CH₃ | CH₂-cyclopropyl | CH₃ | CH₃ | | |
| 1.636 | SCH₂CH₃ | CH₂CH₂CH(CH₃)₂ | CH₃ | CH₃ | | |
| 1.637 | SCH₂CH₃ | CH₂CH₂N(CH₃)₂ | CH₃ | CH₃ | | |
| 1.638 | SCH₂CH₃ | CH₂CH₂CH₂OCH₃ | CH₃ | CH₃ | | |
| 1.639 | SCH₂CH₃ | CH₂CH₂SCH₃ | CH₃ | CH₃ | | |
| 1.640 | SCH₂CH₃ | CH₂CF₃ | CH₃ | CH₃ | | |
| 1.641 | SCH₂CH₃ | CH₂(CH₂)₂CH=CH₂ | CH₃ | CH₃ | | |
| 1.642 | SCH₂CH₃ | CH₂(CH₂)₄CH₃ | CH₃ | CH₃ | | |
| 1.643 | SCH₂CH₃ | CH₂(CH₂)₂SCH₃ | CH₃ | CH₃ | | |
| 1.644 | SCH₂CH₃ | CH₂C₆H₅ | CH₃ | CH₃ | | |
| 1.645 | SCH₂CH₃ | CH₂-3-pyridyl | CH₃ | CH₃ | | |
| 1.646 | SCH₂CH₃ | 5-CH₃-furfur-2-yl | CH₃ | CH₃ | | |
| 1.647 | SCH₂CH₃ | CH₂-thiophen-2-yl | CH₃ | CH₃ | | |
| 1.648 | SCH₂CH₃ | CH₂CH₂C₆H₅ | CH₃ | CH₃ | | |
| 1.649 | SCH₂CH₃ | CH₂CH₂-3-pyridyl | CH₃ | CH₃ | | |
| 1.650 | SCH₂CH₃ | CH₂(CH₂)₂—N-imidazolyl | CH₃ | CH₃ | | |
| 1.651 | SCH₂CH₃ | CH₂CH₃ | CH₂CH₃ | H | | |
| 1.652 | SCH₂CH₃ | CH₂CH₃ | CH₂CH₃ | CH₃ | | |
| 1.653 | SCH₂CH₃ | —CH₂(CH₂)₂CH₂— | | H | | |
| 1.654 | SCH₂CH₃ | —CH₂(CH₂)₃CH₂— | | H | | |
| 1.655 | SCH₂CH₃ | —CH₂CH₂OCH₂CH₂— | | H | | |
| 1.656 | SCH₂CH₃ | —CH₂CH₂N(CH₃)CH₂CH₂— | | H | | |
| 1.657 | SCH₂CH₃ | —CH₂(CH₂)₂CH₂— | | CH₃ | | |
| 1.658 | SCH₂CH₃ | —CH₂(CH₂)₃CH₂— | | CH₃ | | |
| 1.659 | SCH₂CH₃ | —CH₂CH₂OCH₂CH₂— | | CH₃ | | |
| 1.660 | SCH₂CH₃ | —CH₂CH₂N(CH₃)CH₂CH₂— | | CH₃ | | |
| 1.661 | S(O)CH₂CH₃ | cyclopropyl | H | H | | |
| 1.662 | S(O)CH₂CH₃ | CH₂CH=CH | H | H | | |
| 1.663 | S(O)CH₂CH₃ | CH₂CH=CH₂ | H | H | | |
| 1.664 | S(O)CH₂CH₃ | H | H | H | 176 | 0.52 |
| 1.665 | S(O)CH₂CH₃ | CH₃ | H | H | | |
| 1.666 | S(O)CH₂CH₃ | CH₂CH₃ | H | H | | |
| 1.667 | S(O)CH₂CH₃ | CH₂CH₂CH₃ | H | H | | |
| 1.668 | S(O)CH₂CH₃ | CH(CH₃)₂ | H | H | | |
| 1.669 | S(O)CH₂CH₃ | CH₂(CH₂)₃CH₃ | H | H | | |
| 1.670 | S(O)CH₂CH₃ | cyclohexyl | H | H | | |
| 1.671 | S(O)CH₂CH₃ | CH₂CH₂OCH₃ | H | H | | |
| 1.672 | S(O)CH₂CH₃ | 2-tetrahydrofurfuryl | H | H | | |
| 1.673 | S(O)CH₂CH₃ | 2-furfuryl | H | H | | |
| 1.674 | S(O)CH₂CH₃ | CH₂CN | H | H | | |
| 1.675 | S(O)CH₂CH₃ | CH₂CH₂CN | H | H | | |
| 1.676 | S(O)CH₂CH₃ | CH₂-cyclopropyl | H | H | | |
| 1.677 | S(O)CH₂CH₃ | CH₂CH₂CH(CH₃)₂ | H | H | | |
| 1.678 | S(O)CH₂CH₃ | CH₂CH₂N(CH₃)₂ | H | H | | |
| 1.679 | S(O)CH₂CH₃ | CH₂CH₂CH₂OCH₃ | H | H | | |

TABLE 1-continued

Compounds of formula (Ia)

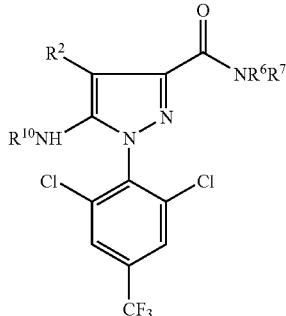

(Ia)

| Cpd | $R^2$ | $R^6$ | $R^7$ | $R^{10}$ | mp (° C.) | RF |
|---|---|---|---|---|---|---|
| 1.680 | S(O)CH$_2$CH$_3$ | CH$_2$CH$_2$SCH$_3$ | H | H | | |
| 1.681 | S(O)CH$_2$CH$_3$ | CH$_2$CF$_3$ | H | H | | |
| 1.682 | S(O)CH$_2$CH$_3$ | CH$_2$(CH$_2$)$_2$CH=CH$_2$ | H | H | | |
| 1.683 | S(O)CH$_2$CH$_3$ | CH$_2$(CH$_2$)$_4$CH$_3$ | H | H | | |
| 1.684 | S(O)CH$_2$CH$_3$ | CH$_2$(CH$_2$)$_2$SCH$_3$ | H | H | | |
| 1.685 | S(O)CH$_2$CH$_3$ | CH$_2$C$_6$H$_5$ | H | H | | |
| 1.686 | S(O)CH$_2$CH$_3$ | CH$_2$-3-pyridyl | H | H | | |
| 1.687 | S(O)CH$_2$CH$_3$ | 5-CH$_3$-furfur-2-yl | H | H | | |
| 1.688 | S(O)CH$_2$CH$_3$ | CH$_2$-thiophen-2-yl | H | H | | |
| 1.689 | S(O)CH$_2$CH$_3$ | CH$_2$CH$_2$C$_6$H$_5$ | H | H | | |
| 1.690 | S(O)CH$_2$CH$_3$ | CH$_2$CH$_2$-3-pyridyl | H | H | | |
| 1.691 | S(O)CH$_2$CH$_3$ | CH$_2$(CH$_2$)$_2$—N-imidazolyl | H | H | | |
| 1.692 | S(O)CH$_2$CH$_3$ | cyclopropyl | CH$_3$ | H | | |
| 1.693 | S(O)CH$_2$CH$_3$ | CH$_2$CH=CH | CH$_3$ | H | | |
| 1.694 | S(O)CH$_2$CH$_3$ | CH$_2$CH=CH$_2$ | CH$_3$ | H | | |
| 1.695 | S(O)CH$_2$CH$_3$ | CH$_3$ | CH$_3$ | H | | |
| 1.696 | S(O)CH$_2$CH$_3$ | CH$_2$CH$_3$ | CH$_3$ | H | | |
| 1.697 | S(O)CH$_2$CH$_3$ | CH$_2$CH$_2$CH$_3$ | CH$_3$ | H | | |
| 1.698 | S(O)CH$_2$CH$_3$ | CH(CH$_3$)$_2$ | CH$_3$ | H | | |
| 1.699 | S(O)CH$_2$CH$_3$ | CH$_2$(CH$_2$)$_3$CH$_3$ | CH$_3$ | H | | |
| 1.700 | S(O)CH$_2$CH$_3$ | cyclohexyl | CH$_3$ | H | | |
| 1.701 | S(O)CH$_2$CH$_3$ | CH$_2$CH$_2$OCH$_3$ | CH$_3$ | H | | |
| 1.702 | S(O)CH$_2$CH$_3$ | 2-tetrahydrofurfuryl | CH$_3$ | H | | |
| 1.703 | S(O)CH$_2$CH$_3$ | 2-furfuryl | CH$_3$ | H | | |
| 1.704 | S(O)CH$_2$CH$_3$ | CH$_2$CN | CH$_3$ | H | | |
| 1.705 | S(O)CH$_2$CH$_3$ | CH$_2$CH$_2$CN | CH$_3$ | H | | |
| 1.706 | S(O)CH$_2$CH$_3$ | CH$_2$-cyclopropyl | CH$_3$ | H | | |
| 1.707 | S(O)CH$_2$CH$_3$ | CH$_2$CH$_2$CH(CH$_3$)$_2$ | CH$_3$ | H | | |
| 1.708 | S(O)CH$_2$CH$_3$ | CH$_2$CH$_2$N(CH$_3$)$_2$ | CH$_3$ | H | | |
| 1.709 | S(O)CH$_2$CH$_3$ | CH$_2$CH$_2$CH$_2$OCH$_3$ | CH$_3$ | H | | |
| 1.710 | S(O)CH$_2$CH$_3$ | CH$_2$CH$_2$SCH$_3$ | CH$_3$ | H | | |
| 1.711 | S(O)CH$_2$CH$_3$ | CH$_2$CF$_3$ | CH$_3$ | H | | |
| 1.712 | S(O)CH$_2$CH$_3$ | CH$_2$(CH$_2$)$_2$CH=CH$_2$ | CH$_3$ | H | | |
| 1.713 | S(O)CH$_2$CH$_3$ | CH$_2$(CH$_2$)$_4$CH$_3$ | CH$_3$ | H | | |
| 1.714 | S(O)CH$_2$CH$_3$ | CH$_2$(CH$_2$)$_2$SCH$_3$ | CH$_3$ | H | | |
| 1.715 | S(O)CH$_2$CH$_3$ | CH$_2$C$_6$H$_5$ | CH$_3$ | H | | |
| 1.716 | S(O)CH$_2$CH$_3$ | CH$_2$-3-pyridyl | CH$_3$ | H | | |
| 1.717 | S(O)CH$_2$CH$_3$ | 5-CH$_3$-furfur-2-yl | CH$_3$ | H | | |
| 1.718 | S(O)CH$_2$CH$_3$ | CH$_2$-thiophen-2-yl | CH$_3$ | H | | |
| 1.719 | S(O)CH$_2$CH$_3$ | CH$_2$CH$_2$C$_6$H$_5$ | CH$_3$ | H | | |
| 1.720 | S(O)CH$_2$CH$_3$ | CH$_2$CH$_2$-3-pyridyl | CH$_3$ | H | | |
| 1.721 | S(O)CH$_2$CH$_3$ | CH$_2$(CH$_2$)$_2$—N-imidazolyl | CH$_3$ | H | | |
| 1.722 | S(O)CH$_2$CH$_3$ | cyclopropyl | H | CH$_3$ | | |
| 1.723 | S(O)CH$_2$CH$_3$ | CH$_2$CH=CH | H | CH$_3$ | | |
| 1.724 | S(O)CH$_2$CH$_3$ | CH$_2$CH=CH$_2$ | H | CH$_3$ | | |
| 1.725 | S(O)CH$_2$CH$_3$ | H | H | CH$_3$ | | |
| 1.726 | S(O)CH$_2$CH$_3$ | CH$_3$ | H | CH$_3$ | | |
| 1.727 | S(O)CH$_2$CH$_3$ | CH$_2$CH$_3$ | H | CH$_3$ | | |
| 1.728 | S(O)CH$_2$CH$_3$ | CH$_2$CH$_2$CH$_3$ | H | CH$_3$ | | |
| 1.729 | S(O)CH$_2$CH$_3$ | CH(CH$_3$)$_2$ | H | CH$_3$ | | |
| 1.730 | S(O)CH$_2$CH$_3$ | CH$_2$(CH$_2$)$_3$CH$_3$ | H | CH$_3$ | | |
| 1.731 | S(O)CH$_2$CH$_3$ | cyclohexyl | H | CH$_3$ | | |
| 1.732 | S(O)CH$_2$CH$_3$ | CH$_2$CH$_2$OCH$_3$ | H | CH$_3$ | | |
| 1.733 | S(O)CH$_2$CH$_3$ | 2-tetrahydrofurfuryl | H | CH$_3$ | | |
| 1.734 | S(O)CH$_2$CH$_3$ | 2-furfuryl | H | CH$_3$ | | |
| 1.735 | S(O)CH$_2$CH$_3$ | CH$_2$CN | H | CH$_3$ | | |
| 1.736 | S(O)CH$_2$CH$_3$ | CH$_2$CH$_2$CN | H | CH$_3$ | | |

TABLE 1-continued

Compounds of formula (Ia)

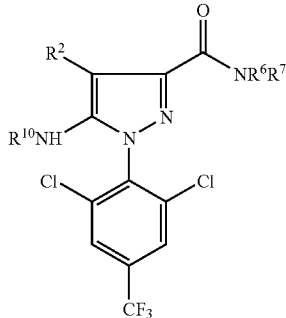

| Cpd | $R^2$ | $R^6$ | $R^7$ | $R^{10}$ | mp (° C.) | RF |
|---|---|---|---|---|---|---|
| 1.737 | S(O)CH$_2$CH$_3$ | CH$_2$-cyclopropyl | H | CH$_3$ | | |
| 1.738 | S(O)CH$_2$CH$_3$ | CH$_2$CH$_2$CH(CH$_3$)$_2$ | H | CH$_3$ | | |
| 1.739 | S(O)CH$_2$CH$_3$ | CH$_2$CH$_2$N(CH$_3$)$_2$ | H | CH$_3$ | | |
| 1.740 | S(O)CH$_2$CH$_3$ | CH$_2$CH$_2$CH$_2$OCH$_3$ | H | CH$_3$ | | |
| 1.741 | S(O)CH$_2$CH$_3$ | CH$_2$CH$_2$SCH$_3$ | H | CH$_3$ | | |
| 1.742 | S(O)CH$_2$CH$_3$ | CH$_2$CF$_3$ | H | CH$_3$ | | |
| 1.743 | S(O)CH$_2$CH$_3$ | CH$_2$(CH$_2$)$_2$CH=CH$_2$ | H | CH$_3$ | | |
| 1.744 | S(O)CH$_2$CH$_3$ | CH$_2$(CH$_2$)$_4$CH$_3$ | H | CH$_3$ | | |
| 1.745 | S(O)CH$_2$CH$_3$ | CH$_2$(CH$_2$)$_2$SCH$_3$ | H | CH$_3$ | | |
| 1.746 | S(O)CH$_2$CH$_3$ | CH$_2$C$_6$H$_5$ | H | CH$_3$ | | |
| 1.747 | S(O)CH$_2$CH$_3$ | CH$_2$-3-pyridyl | H | CH$_3$ | | |
| 1.748 | S(O)CH$_2$CH$_3$ | 5-CH$_3$-furfur-2-yl | H | CH$_3$ | | |
| 1.749 | S(O)CH$_2$CH$_3$ | CH$_2$-thiophen-2-yl | H | CH$_3$ | | |
| 1.750 | S(O)CH$_2$CH$_3$ | CH$_2$CH$_2$C$_6$H$_5$ | H | CH$_3$ | | |
| 1.751 | S(O)CH$_2$CH$_3$ | CH$_2$CH$_2$-3-pyridyl | H | CH$_3$ | | |
| 1.752 | S(O)CH$_2$CH$_3$ | CH$_2$(CH$_2$)$_2$—N-imidazolyl | H | CH$_3$ | | |
| 1.753 | S(O)CH$_2$CH$_3$ | cyclopropyl | CH$_3$ | CH$_3$ | | |
| 1.754 | S(O)CH$_2$CH$_3$ | CH$_2$CH=CH | CH$_3$ | CH$_3$ | | |
| 1.755 | S(O)CH$_2$CH$_3$ | CH$_2$CH=CH$_2$ | CH$_3$ | CH$_3$ | | |
| 1.756 | S(O)CH$_2$CH$_3$ | CH$_3$ | CH$_3$ | CH$_3$ | | |
| 1.757 | S(O)CH$_2$CH$_3$ | CH$_2$CH$_3$ | CH$_3$ | CH$_3$ | | |
| 1.758 | S(O)CH$_2$CH$_3$ | CH$_2$CH$_2$CH$_3$ | CH$_3$ | CH$_3$ | | |
| 1.759 | S(O)CH$_2$CH$_3$ | CH(CH$_3$)$_2$ | CH$_3$ | CH$_3$ | | |
| 1.760 | S(O)CH$_2$CH$_3$ | CH$_2$(CH$_2$)$_3$CH$_3$ | CH$_3$ | CH$_3$ | | |
| 1.761 | S(O)CH$_2$CH$_3$ | cyclohexyl | CH$_3$ | CH$_3$ | | |
| 1.762 | S(O)CH$_2$CH$_3$ | CH$_2$CH$_2$OCH$_3$ | CH$_3$ | CH$_3$ | | |
| 1.763 | S(O)CH$_2$CH$_3$ | 2-tetrahydrofurfuryl | CH$_3$ | CH$_3$ | | |
| 1.764 | S(O)CH$_2$CH$_3$ | 2-furfuryl | CH$_3$ | CH$_3$ | | |
| 1.765 | S(O)CH$_2$CH$_3$ | CH$_2$CN | CH$_3$ | CH$_3$ | | |
| 1.766 | S(O)CH$_2$CH$_3$ | CH$_2$CH$_2$CN | CH$_3$ | CH$_3$ | | |
| 1.767 | S(O)CH$_2$CH$_3$ | CH$_2$-cyclopropyl | CH$_3$ | CH$_3$ | | |
| 1.768 | S(O)CH$_2$CH$_3$ | CH$_2$CH$_2$CH(CH$_3$)$_2$ | CH$_3$ | CH$_3$ | | |
| 1.769 | S(O)CH$_2$CH$_3$ | CH$_2$CH$_2$N(CH$_3$)$_2$ | CH$_3$ | CH$_3$ | | |
| 1.770 | S(O)CH$_2$CH$_3$ | CH$_2$CH$_2$CH$_2$OCH$_3$ | CH$_3$ | CH$_3$ | | |
| 1.771 | S(O)CH$_2$CH$_3$ | CH$_2$CH$_2$SCH$_3$ | CH$_3$ | CH$_3$ | | |
| 1.772 | S(O)CH$_2$CH$_3$ | CH$_2$CF$_3$ | CH$_3$ | CH$_3$ | | |
| 1.773 | S(O)CH$_2$CH$_3$ | CH$_2$(CH$_2$)$_2$CH=CH$_2$ | CH$_3$ | CH$_3$ | | |
| 1.774 | S(O)CH$_2$CH$_3$ | CH$_2$(CH$_2$)$_4$CH$_3$ | CH$_3$ | CH$_3$ | | |
| 1.775 | S(O)CH$_2$CH$_3$ | CH$_2$(CH$_2$)$_2$SCH$_3$ | CH$_3$ | CH$_3$ | | |
| 1.776 | S(O)CH$_2$CH$_3$ | CH$_2$C$_6$H$_5$ | CH$_3$ | CH$_3$ | | |
| 1.777 | S(O)CH$_2$CH$_3$ | CH$_2$-3-pyridyl | CH$_3$ | CH$_3$ | | |
| 1.778 | S(O)CH$_2$CH$_3$ | 5-CH$_3$-furfur-2-yl | CH$_3$ | CH$_3$ | | |
| 1.779 | S(O)CH$_2$CH$_3$ | CH$_2$-thiophen-2-yl | CH$_3$ | CH$_3$ | | |
| 1.780 | S(O)CH$_2$CH$_3$ | CH$_2$CH$_2$C$_6$H$_5$ | CH$_3$ | CH$_3$ | | |
| 1.781 | S(O)CH$_2$CH$_3$ | CH$_2$CH$_2$-3-pyridyl | CH$_3$ | CH$_3$ | | |
| 1.782 | S(O)CH$_2$CH$_3$ | CH$_2$(CH$_2$)$_2$—N-imidazolyl | CH$_3$ | CH$_3$ | | |
| 1.783 | S(O)CH$_2$CH$_3$ | CH$_2$CH$_3$ | CH$_2$CH$_3$ | H | | |
| 1.784 | S(O)CH$_2$CH$_3$ | CH$_2$CH$_3$ | CH$_2$CH$_3$ | CH$_3$ | | |
| 1.785 | S(O)CH$_2$CH$_3$ | —CH$_2$(CH$_2$)$_2$CH$_2$— | | H | | |
| 1.786 | S(O)CH$_2$CH$_3$ | —CH$_2$(CH$_2$)$_3$CH$_2$— | | H | | |
| 1.787 | S(O)CH$_2$CH$_3$ | —CH$_2$CH$_2$OCH$_2$CH$_2$— | | H | | |
| 1.788 | S(O)CH$_2$CH$_3$ | —CH$_2$CH$_2$N(CH$_3$)CH$_2$CH$_2$— | | H | | |
| 1.789 | S(O)CH$_2$CH$_3$ | —CH$_2$(CH$_2$)$_2$CH$_2$— | | CH$_3$ | | |
| 1.790 | S(O)CH$_2$CH$_3$ | —CH$_2$(CH$_2$)$_3$CH$_2$— | | CH$_3$ | | |
| 1.791 | S(O)CH$_2$CH$_3$ | —CH$_2$CH$_2$OCH$_2$CH$_2$— | | CH$_3$ | | |
| 1.792 | S(O)CH$_2$CH$_3$ | —CH$_2$CH$_2$N(CH$_3$)CH$_2$CH$_2$— | | CH$_3$ | | |
| 1.793 | S(O)$_2$CH$_2$CH$_3$ | cyclopropyl | H | H | | |

TABLE 1-continued

Compounds of formula (Ia)

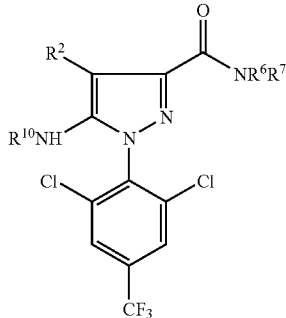

(Ia)

| Cpd | R² | R⁶ | R⁷ | R¹⁰ | mp (° C.) | RF |
|---|---|---|---|---|---|---|
| 1.794 | S(O)₂CH₂CH₃ | CH₂CH=CH | H | H | | |
| 1.795 | S(O)₂CH₂CH₃ | CH₂CH=CH₂ | H | H | | |
| 1.796 | S(O)₂CH₂CH₃ | H | H | H | 224 | 0.75 |
| 1.797 | S(O)₂CH₂CH₃ | CH₃ | H | H | | |
| 1.798 | S(O)₂CH₂CH₃ | CH₂CH₃ | H | H | | |
| 1.799 | S(O)₂CH₂CH₃ | CH₂CH₂CH₃ | H | H | | |
| 1.800 | S(O)₂CH₂CH₃ | CH(CH₃)₂ | H | H | | |
| 1.801 | S(O)₂CH₂CH₃ | CH₂(CH₂)₃CH₃ | H | H | | |
| 1.802 | S(O)₂CH₂CH₃ | cyclohexyl | H | H | | |
| 1.803 | S(O)₂CH₂CH₃ | CH₂CH₂OCH₃ | H | H | | |
| 1.804 | S(O)₂CH₂CH₃ | 2-tetrahydrofurfuryl | H | H | | |
| 1.805 | S(O)₂CH₂CH₃ | 2-furfuryl | H | H | | |
| 1.806 | S(O)₂CH₂CH₃ | CH₂CN | H | H | | |
| 1.807 | S(O)₂CH₂CH₃ | CH₂CH₂CN | H | H | | |
| 1.808 | S(O)₂CH₂CH₃ | CH₂-cyclopropyl | H | H | | |
| 1.809 | S(O)₂CH₂CH₃ | CH₂CH₂CH(CH₃)₂ | H | H | | |
| 1.810 | S(O)₂CH₂CH₃ | CH₂CH₂N(CH₃)₂ | H | H | | |
| 1.811 | S(O)₂CH₂CH₃ | CH₂CH₂CH₂OCH₃ | H | H | | |
| 1.812 | S(O)₂CH₂CH₃ | CH₂CH₂SCH₃ | H | H | | |
| 1.813 | S(O)₂CH₂CH₃ | CH₂CF₃ | H | H | | |
| 1.814 | S(O)₂CH₂CH₃ | CH₂(CH₂)₂CH=CH₂ | H | H | | |
| 1.815 | S(O)₂CH₂CH₃ | CH₂(CH₂)₄CH₃ | H | H | | |
| 1.816 | S(O)₂CH₂CH₃ | CH₂(CH₂)₂SCH₃ | H | H | | |
| 1.817 | S(O)₂CH₂CH₃ | CH₂C₆H₅ | H | H | | |
| 1.818 | S(O)₂CH₂CH₃ | CH₂-3-pyridyl | H | H | | |
| 1.819 | S(O)₂CH₂CH₃ | 5-CH₃-furfur-2-yl | H | H | | |
| 1.820 | S(O)₂CH₂CH₃ | CH₂-thiophen-2-yl | H | H | | |
| 1.821 | S(O)₂CH₂CH₃ | CH₂CH₂C₆H₅ | H | H | | |
| 1.822 | S(O)₂CH₂CH₃ | CH₂CH₂-3-pyridyl | H | H | | |
| 1.823 | S(O)₂CH₂CH₃ | CH₂(CH₂)₂—N-imidazolyl | H | H | | |
| 1.824 | S(O)₂CH₂CH₃ | cyclopropyl | CH₃ | H | | |
| 1.825 | S(O)₂CH₂CH₃ | CH₂CH=CH | CH₃ | H | | |
| 1.826 | S(O)₂CH₂CH₃ | CH₂CH=CH₂ | CH₃ | H | | |
| 1.827 | S(O)₂CH₂CH₃ | CH₃ | CH₃ | H | | |
| 1.828 | S(O)₂CH₂CH₃ | CH₂CH₃ | CH₃ | H | | |
| 1.829 | S(O)₂CH₂CH₃ | CH₂CH₂CH₃ | CH₃ | H | | |
| 1.830 | S(O)₂CH₂CH₃ | CH(CH₃)₂ | CH₃ | H | | |
| 1.831 | S(O)₂CH₂CH₃ | CH₂(CH₂)₃CH₃ | CH₃ | H | | |
| 1.832 | S(O)₂CH₂CH₃ | cyclohexyl | CH₃ | H | | |
| 1.833 | S(O)₂CH₂CH₃ | CH₂CH₂OCH₃ | CH₃ | H | | |
| 1.834 | S(O)₂CH₂CH₃ | 2-tetrahydrofurfuryl | CH₃ | H | | |
| 1.835 | S(O)₂CH₂CH₃ | 2-furfuryl | CH₃ | H | | |
| 1.836 | S(O)₂CH₂CH₃ | CH₂CN | CH₃ | H | | |
| 1.837 | S(O)₂CH₂CH₃ | CH₂CH₂CN | CH₃ | H | | |
| 1.838 | S(O)₂CH₂CH₃ | CH₂-cyclopropyl | CH₃ | H | | |
| 1.839 | S(O)₂CH₂CH₃ | CH₂CH₂CH(CH₃)₂ | CH₃ | H | | |
| 1.840 | S(O)₂CH₂CH₃ | CH₂CH₂N(CH₃)₂ | CH₃ | H | | |
| 1.841 | S(O)₂CH₂CH₃ | CH₂CH₂CH₂OCH₃ | CH₃ | H | | |
| 1.842 | S(O)₂CH₂CH₃ | CH₂CH₂SCH₃ | CH₃ | H | | |
| 1.843 | S(O)₂CH₂CH₃ | CH₂CF₃ | CH₃ | H | | |
| 1.844 | S(O)₂CH₂CH₃ | CH₂(CH₂)₂CH=CH₂ | CH₃ | H | | |
| 1.845 | S(O)₂CH₂CH₃ | CH₂(CH₂)₄CH₃ | CH₃ | H | | |
| 1.846 | S(O)₂CH₂CH₃ | CH₂(CH₂)₂SCH₃ | CH₃ | H | | |
| 1.847 | S(O)₂CH₂CH₃ | CH₂C₆H₅ | CH₃ | H | | |
| 1.848 | S(O)₂CH₂CH₃ | CH₂-3-pyridyl | CH₃ | H | | |
| 1.849 | S(O)₂CH₂CH₃ | 5-CH₃-furfur-2-yl | CH₃ | H | | |
| 1.850 | S(O)₂CH₂CH₃ | CH₂-thiophen-2-yl | CH₃ | H | | |

TABLE 1-continued

Compounds of formula (Ia)

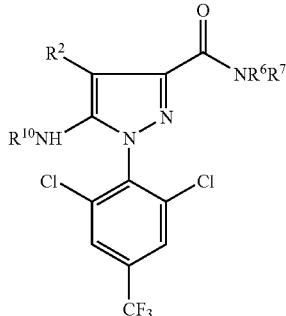

(Ia)

| Cpd | R² | R⁶ | R⁷ | R¹⁰ | mp (° C.) | RF |
|---|---|---|---|---|---|---|
| 1.851 | S(O)₂CH₂CH₃ | CH₂CH₂C₆H₅ | CH₃ | H | | |
| 1.852 | S(O)₂CH₂CH₃ | CH₂CH₂-3-pyridyl | CH₃ | H | | |
| 1.853 | S(O)₂CH₂CH₃ | CH₂(CH₂)₂—N-imidazolyl | CH₃ | H | | |
| 1.854 | S(O)₂CH₂CH₃ | cyclopropyl | H | CH₃ | | |
| 1.855 | S(O)₂CH₂CH₃ | CH₂CH≡CH | H | CH₃ | | |
| 1.856 | S(O)₂CH₂CH₃ | CH₂CH═CH₂ | H | CH₃ | | |
| 1.857 | S(O)₂CH₂CH₃ | H | H | CH₃ | | |
| 1.858 | S(O)₂CH₂CH₃ | CH₃ | H | CH₃ | | |
| 1.859 | S(O)₂CH₂CH₃ | CH₂CH₃ | H | CH₃ | | |
| 1.860 | S(O)₂CH₂CH₃ | CH₂CH₂CH₃ | H | CH₃ | | |
| 1.861 | S(O)₂CH₂CH₃ | CH(CH₃)₂ | H | CH₃ | | |
| 1.862 | S(O)₂CH₂CH₃ | CH₂(CH₂)₃CH₃ | H | CH₃ | | |
| 1.863 | S(O)₂CH₂CH₃ | cyclohexyl | H | CH₃ | | |
| 1.864 | S(O)₂CH₂CH₃ | CH₂CH₂OCH₃ | H | CH₃ | | |
| 1.865 | S(O)₂CH₂CH₃ | 2-tetrahydrofurfuryl | H | CH₃ | | |
| 1.866 | S(O)₂CH₂CH₃ | 2-furfuryl | H | CH₃ | | |
| 1.867 | S(O)₂CH₂CH₃ | CH₂CN | H | CH₃ | | |
| 1.868 | S(O)₂CH₂CH₃ | CH₂CH₂CN | H | CH₃ | | |
| 1.869 | S(O)₂CH₂CH₃ | CH₂-cyclopropyl | H | CH₃ | | |
| 1.870 | S(O)₂CH₂CH₃ | CH₂CH₂CH(CH₃)₂ | H | CH₃ | | |
| 1.871 | S(O)₂CH₂CH₃ | CH₂CH₂N(CH₃)₂ | H | CH₃ | | |
| 1.872 | S(O)₂CH₂CH₃ | CH₂CH₂CH₂OCH₃ | H | CH₃ | | |
| 1.873 | S(O)₂CH₂CH₃ | CH₂CH₂SCH₃ | H | CH₃ | | |
| 1.874 | S(O)₂CH₂CH₃ | CH₂CF₃ | H | CH₃ | | |
| 1.875 | S(O)₂CH₂CH₃ | CH₂(CH₂)₂CH═CH₂ | H | CH₃ | | |
| 1.876 | S(O)₂CH₂CH₃ | CH₂(CH₂)₄CH₃ | H | CH₃ | | |
| 1.877 | S(O)₂CH₂CH₃ | CH₂(CH₂)₂SCH₃ | H | CH₃ | | |
| 1.878 | S(O)₂CH₂CH₃ | CH₂C₆H₅ | H | CH₃ | | |
| 1.879 | S(O)₂CH₂CH₃ | CH₂-3-pyridyl | H | CH₃ | | |
| 1.880 | S(O)₂CH₂CH₃ | 5-CH₃-furfur-2-yl | H | CH₃ | | |
| 1.881 | S(O)₂CH₂CH₃ | CH₂-thiophen-2-yl | H | CH₃ | | |
| 1.882 | S(O)₂CH₂CH₃ | CH₂CH₂C₆H₅ | H | CH₃ | | |
| 1.883 | S(O)₂CH₂CH₃ | CH₂CH₂-3-pyridyl | H | CH₃ | | |
| 1.884 | S(O)₂CH₂CH₃ | CH₂(CH₂)₂—N-imidazolyl | H | CH₃ | | |
| 1.885 | S(O)₂CH₂CH₃ | cyclopropyl | CH₃ | CH₃ | | |
| 1.886 | S(O)₂CH₂CH₃ | CH₂CH≡CH | CH₃ | CH₃ | | |
| 1.887 | S(O)₂CH₂CH₃ | CH₂CH═CH₂ | CH₃ | CH₃ | | |
| 1.888 | S(O)₂CH₂CH₃ | CH₃ | CH₃ | CH₃ | | |
| 1.889 | S(O)₂CH₂CH₃ | CH₂CH₃ | CH₃ | CH₃ | | |
| 1.890 | S(O)₂CH₂CH₃ | CH₂CH₂CH₃ | CH₃ | CH₃ | | |
| 1.891 | S(O)₂CH₂CH₃ | CH(CH₃)₂ | CH₃ | CH₃ | | |
| 1.892 | S(O)₂CH₂CH₃ | CH₂(CH₂)₃CH₃ | CH₃ | CH₃ | | |
| 1.893 | S(O)₂CH₂CH₃ | cyclohexyl | CH₃ | CH₃ | | |
| 1.894 | S(O)₂CH₂CH₃ | CH₂CH₂OCH₃ | CH₃ | CH₃ | | |
| 1.895 | S(O)₂CH₂CH₃ | 2-tetrahydrofurfuryl | CH₃ | CH₃ | | |
| 1.896 | S(O)₂CH₂CH₃ | 2-furfuryl | CH₃ | CH₃ | | |
| 1.897 | S(O)₂CH₂CH₃ | CH₂CN | CH₃ | CH₃ | | |
| 1.898 | S(O)₂CH₂CH₃ | CH₂CH₂CN | CH₃ | CH₃ | | |
| 1.899 | S(O)₂CH₂CH₃ | CH₂-cyclopropyl | CH₃ | CH₃ | | |
| 1.900 | S(O)₂CH₂CH₃ | CH₂CH₂CH(CH₃)₂ | CH₃ | CH₃ | | |
| 1.901 | S(O)₂CH₂CH₃ | CH₂CH₂N(CH₃)₂ | CH₃ | CH₃ | | |
| 1.902 | S(O)₂CH₂CH₃ | CH₂CH₂CH₂OCH₃ | CH₃ | CH₃ | | |
| 1.903 | S(O)₂CH₂CH₃ | CH₂CH₂SCH₃ | CH₃ | CH₃ | | |
| 1.904 | S(O)₂CH₂CH₃ | CH₂CF₃ | CH₃ | CH₃ | | |
| 1.905 | S(O)₂CH₂CH₃ | CH₂(CH₂)₂CH═CH₂ | CH₃ | CH₃ | | |
| 1.906 | S(O)₂CH₂CH₃ | CH₂(CH₂)₄CH₃ | CH₃ | CH₃ | | |
| 1.907 | S(O)₂CH₂CH₃ | CH₂(CH₂)₂SCH₃ | CH₃ | CH₃ | | |

TABLE 1-continued

Compounds of formula (Ia)

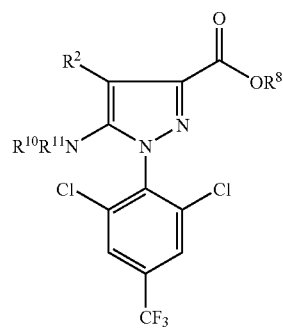

(Ia)

| Cpd | $R^2$ | $R^6$ | $R^7$ | $R^{10}$ | mp (° C.) | RF |
|---|---|---|---|---|---|---|
| 1.908 | $S(O)_2CH_2CH_3$ | $CH_2C_6H_5$ | $CH_3$ | $CH_3$ | | |
| 1.909 | $S(O)_2CH_2CH_3$ | $CH_2$-3-pyridyl | $CH_3$ | $CH_3$ | | |
| 1.910 | $S(O)_2CH_2CH_3$ | 5-$CH_3$-furfur-2-yl | $CH_3$ | $CH_3$ | | |
| 1.911 | $S(O)_2CH_2CH_3$ | $CH_2$-thiophen-2-yl | $CH_3$ | $CH_3$ | | |
| 1.912 | $S(O)_2CH_2CH_3$ | $CH_2CH_2C_6H_5$ | $CH_3$ | $CH_3$ | | |
| 1.913 | $S(O)_2CH_2CH_3$ | $CH_2CH_2$-3-pyridyl | $CH_3$ | $CH_3$ | | |
| 1.914 | $S(O)_2CH_2CH_3$ | $CH_2(CH_2)_2$—N-imidazolyl | $CH_3$ | $CH_3$ | | |
| 1.915 | $S(O)_2CH_2CH_3$ | $CH_2CH_3$ | $CH_2CH_3$ | H | | |
| 1.916 | $S(O)_2CH_2CH_3$ | $CH_2CH_3$ | $CH_2CH_3$ | $CH_3$ | | |
| 1.917 | $S(O)_2CH_2CH_3$ | —$CH_2(CH_2)_2CH_2$— | | H | | |
| 1.918 | $S(O)_2CH_2CH_3$ | —$CH_2(CH_2)_3CH_2$— | | H | | |
| 1.919 | $S(O)_2CH_2CH_3$ | —$CH_2CH_2OCH_2CH_2$— | | H | | |
| 1.920 | $S(O)_2CH_2CH_3$ | —$CH_2CH_2N(CH_3)CH_2CH_2$— | | H | | |
| 1.921 | $S(O)_2CH_2CH_3$ | —$CH_2(CH_2)_2CH_2$— | | $CH_3$ | | |
| 1.922 | $S(O)_2CH_2CH_3$ | —$CH_2(CH_2)_3CH_2$— | | $CH_3$ | | |
| 1.923 | $S(O)_2CH_2CH_3$ | —$CH_2CH_2OCH_2CH_2$— | | $CH_3$ | | |
| 1.924 | $S(O)_2CH_2CH_3$ | —$CH_2CH_2N(CH_3)CH_2CH_2$— | | $CH_3$ | | |

TABLE 2

Compounds of formula (Ib)

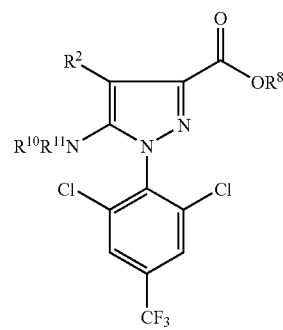

(Ib)

| Cpd | $R^2$ | $R^8$ | $R^{10}$ | $R^{11}$ | mp (° C.) | RF |
|---|---|---|---|---|---|---|
| 2.1 | H | H | H | H | 213 | 0.03 |
| 2.2 | H | H | $CH_3$ | H | | |
| 2.3 | H | H | $CH_3$ | $CH_3$ | | |
| 2.4 | H | $CH_3$ | H | H | | |
| 2.5 | H | $CH_3$ | $CH_3$ | H | | |
| 2.6 | H | $CH_3$ | $CH_3$ | $CH_3$ | | |
| 2.7 | H | $CH_2CH_3$ | H | H | | |
| 2.8 | H | $CH_2CH_3$ | $CH_3$ | H | | |
| 2.9 | H | $CH_2CH_3$ | $CH_3$ | $CH_3$ | | |
| 2.10 | $SCF_3$ | H | H | H | 199 | 0.59 |
| 2.11 | $SCF_3$ | H | $CH_3$ | H | 150 | 0.28 |
| 2.12 | $SCF_3$ | H | $CH_3$ | $CH_3$ | | |
| 2.13 | $SCF_3$ | $CH_3$ | H | H | | |
| 2.14 | $SCF_3$ | $CH_3$ | $CH_3$ | H | | |
| 2.15 | $SCF_3$ | $CH_3$ | $CH_3$ | $CH_3$ | | |
| 2.16 | $SCF_3$ | $CH_2CH_3$ | H | H | | |
| 2.17 | $SCF_3$ | $CH_2CH_3$ | $CH_3$ | H | | |
| 2.18 | $SCF_3$ | $CH_2CH_3$ | $CH_3$ | $CH_3$ | | |
| 2.19 | $S(O)CF_3$ | H | H | H | | |
| 2.20 | $S(O)CF_3$ | H | $CH_3$ | H | | |
| 2.21 | $S(O)CF_3$ | H | $CH_3$ | $CH_3$ | | |
| 2.22 | $S(O)CF_3$ | $CH_3$ | H | H | | |
| 2.23 | $S(O)CF_3$ | $CH_3$ | $CH_3$ | H | | |
| 2.24 | $S(O)CF_3$ | $CH_3$ | $CH_3$ | $CH_3$ | | |
| 2.25 | $S(O)CF_3$ | $CH_2CH_3$ | H | H | | |
| 2.26 | $S(O)CF_3$ | $CH_2CH_3$ | $CH_3$ | H | | |

TABLE 2-continued

Compounds of formula (Ib)

| Cpd | R² | R⁸ | R¹⁰ | R¹¹ | mp (° C.) | RF |
|---|---|---|---|---|---|---|
| 2.27 | S(O)CF₃ | CH₂CH₃ | CH₃ | CH₃ | | |
| 2.28 | S(O)₂CF₃ | H | H | H | | |
| 2.29 | S(O)₂CF₃ | H | CH₃ | H | | |
| 2.30 | S(O)₂CF₃ | H | CH₃ | CH₃ | | |
| 2.31 | S(O)₂CF₃ | CH₃ | H | H | | |
| 2.32 | S(O)₂CF₃ | CH₃ | CH₃ | H | | |
| 2.33 | S(O)₂CF₃ | CH₃ | CH₃ | CH₃ | | |
| 2.34 | S(O)₂CF₃ | CH₂CH₃ | H | H | | |
| 2.35 | S(O)₂CF₃ | CH₂CH₃ | CH₃ | H | | |
| 2.36 | S(O)₂CF₃ | CH₂CH₃ | CH₃ | CH₃ | | |
| 2.37 | SCH₂CH₃ | H | H | H | | |
| 2.38 | SCH₂CH₃ | H | CH₃ | H | | |
| 2.39 | SCH₂CH₃ | H | CH₃ | CH₃ | | |
| 2.40 | SCH₂CH₃ | CH₃ | H | H | | |
| 2.41 | SCH₂CH₃ | CH₃ | CH₃ | H | | |
| 2.42 | SCH₂CH₃ | CH₃ | CH₃ | CH₃ | | |
| 2.43 | SCH₂CH₃ | CH₂CH₃ | H | H | | |
| 2.44 | SCH₂CH₃ | CH₂CH₃ | CH₃ | H | | |
| 2.45 | SCH₂CH₃ | CH₂CH₃ | CH₃ | CH₃ | | |
| 2.46 | S(O)CH₂CH₃ | H | H | H | | |
| 2.47 | S(O)CH₂CH₃ | H | CH₃ | H | | |
| 2.48 | S(O)CH₂CH₃ | H | CH₃ | CH₃ | | |
| 2.49 | S(O)CH₂CH₃ | CH₃ | H | H | | |
| 2.50 | S(O)CH₂CH₃ | CH₃ | CH₃ | H | | |
| 2.51 | S(O)CH₂CH₃ | CH₃ | CH₃ | CH₃ | | |
| 2.52 | S(O)CH₂CH₃ | CH₂CH₃ | H | H | | |
| 2.53 | S(O)CH₂CH₃ | CH₂CH₃ | CH₃ | H | | |
| 2.54 | S(O)CH₂CH₃ | CH₂CH₃ | CH₃ | CH₃ | | |
| 2.55 | S(O)₂CH₂CH₃ | H | H | H | | |
| 2.56 | S(O)₂CH₂CH₃ | H | CH₃ | H | | |
| 2.57 | S(O)₂CH₂CH₃ | H | CH₃ | CH₃ | | |
| 2.58 | S(O)₂CH₂CH₃ | CH₃ | H | H | | |
| 2.59 | S(O)₂CH₂CH₃ | CH₃ | CH₃ | H | | |
| 2.60 | S(O)₂CH₂CH₃ | CH₃ | CH₃ | CH₃ | | |
| 2.61 | S(O)₂CH₂CH₃ | CH₂CH₃ | H | H | | |
| 2.62 | S(O)₂CH₂CH₃ | CH₂CH₃ | CH₃ | H | | |
| 2.63 | S(O)₂CH₂CH₃ | CH₂CH₃ | CH₃ | CH₃ | | |
| 2.64 | SCH₃ | H | H | H | | |
| 2.65 | SCH₃ | H | CH₃ | H | | |
| 2.66 | SCH₃ | H | CH₃ | CH₃ | | |
| 2.67 | SCH₃ | CH₃ | H | H | | |
| 2.68 | SCH₃ | CH₃ | CH₃ | H | | |
| 2.69 | SCH₃ | CH₃ | CH₃ | CH₃ | | |
| 2.70 | SCH₃ | CH₂CH₃ | H | H | | |
| 2.71 | SCH₃ | CH₂CH₃ | CH₃ | H | | |
| 2.72 | SCH₃ | CH₂CH₃ | CH₃ | CH₃ | | |
| 2.73 | S(O)CH₃ | H | H | H | | |
| 2.74 | S(O)CH₃ | H | CH₃ | H | | |
| 2.75 | S(O)CH₃ | H | CH₃ | CH₃ | | |
| 2.76 | S(O)CH₃ | CH₃ | H | H | | |
| 2.77 | S(O)CH₃ | CH₃ | CH₃ | H | | |
| 2.78 | S(O)CH₃ | CH₃ | CH₃ | CH₃ | | |
| 2.79 | S(O)CH₃ | CH₂CH₃ | H | H | | |
| 2.80 | S(O)CH₃ | CH₂CH₃ | CH₃ | H | | |
| 2.81 | S(O)CH₃ | CH₂CH₃ | CH₃ | CH₃ | | |
| 2.82 | S(O)₂CH₃ | H | H | H | | |
| 2.83 | S(O)₂CH₃ | H | CH₃ | H | | |
| 2.84 | S(O)₂CH₃ | H | CH₃ | CH₃ | | |
| 2.85 | S(O)₂CH₃ | CH₃ | H | H | | |
| 2.86 | S(O)₂CH₃ | CH₃ | CH₃ | H | | |
| 2.87 | S(O)₂CH₃ | CH₃ | CH₃ | CH₃ | | |
| 2.89 | S(O)₂CH₃ | CH₂CH₃ | H | H | | |
| 2.90 | S(O)₂CH₃ | CH₂CH₃ | CH₃ | H | | |
| 2.91 | S(O)₂CH₃ | CH₂CH₃ | CH₃ | CH₃ | | |
| 2.92 | SCClF₂ | H | H | H | | |
| 2.93 | SCClF₂ | H | CH₃ | H | | |
| 2.94 | SCClF₂ | H | CH₃ | CH₃ | | |
| 2.95 | SCClF₂ | CH₃ | H | H | | |
| 2.96 | SCClF₂ | CH₃ | CH₃ | H | | |
| 2.97 | SCClF₂ | CH₃ | CH₃ | CH₃ | | |
| 2.98 | SCClF₂ | CH₂CH₃ | H | H | | |
| 2.99 | SCClF₂ | CH₂CH₃ | CH₃ | H | | |
| 2.100 | SCClF₂ | CH₂CH₃ | CH₃ | CH₃ | | |
| 2.101 | S(O)CClF₂ | H | H | H | | |
| 2.102 | S(O)CClF₂ | H | CH₃ | H | | |
| 2.103 | S(O)CClF₂ | H | CH₃ | CH₃ | | |
| 2.104 | S(O)OClF₂ | CH₃ | H | H | | |
| 2.105 | S(O)CClF₂ | CH₃ | CH₃ | H | | |
| 2.106 | S(O)CClF₂ | CH₃ | CH₃ | CH₃ | | |
| 2.107 | S(O)CClF₂ | CH₂CH₃ | H | H | | |
| 2.108 | S(O)CClF₂ | CH₂CH₃ | CH₃ | H | | |
| 2.109 | S(O)CClF₂ | CH₂CH₃ | CH₃ | CH₃ | | |
| 2.110 | S(O)₂CClF₂ | H | H | H | | |
| 2.111 | S(O)₂CClF₂ | H | CH₃ | H | | |
| 2.112 | S(O)₂CClF₂ | H | CH₃ | CH₃ | | |
| 2.113 | S(O)₂CClF₂ | CH₃ | H | H | | |
| 2.114 | S(O)₂CClF₂ | CH₃ | CH₃ | H | | |
| 2.115 | S(O)₂CClF₂ | CH₃ | CH₃ | CH₃ | | |
| 2.116 | S(O)₂CClF₂ | CH₂CH₃ | H | H | | |
| 2.117 | S(O)₂CClF₂ | CH₂CH₃ | CH₃ | H | | |
| 2.118 | S(O)₂CClF₂ | CH₂CH₃ | CH₃ | CH₃ | | |
| 2.119 | SCCl₂F | H | H | H | | |
| 2.120 | SCCl₂F | H | CH₃ | H | | |
| 2.121 | SCCl₂F | H | CH₃ | CH₃ | | |
| 2.122 | SCCl₂F | CH₃ | H | H | | |
| 2.123 | SCCl₂F | CH₃ | CH₃ | H | | |
| 2.124 | SCCl₂F | CH₃ | CH₃ | CH₃ | | |
| 2.125 | SCCl₂F | CH₂CH₃ | H | H | | |
| 2.126 | SCCl₂F | CH₂HH₃ | CH₃ | H | | |
| 2.127 | SCCl₂F | CH₂CH₃ | CH₃ | CH₃ | | |
| 2.128 | S(O)CCl₂F | H | H | H | | |
| 2.129 | S(O)CCl₂F | H | CH₃ | H | | |
| 2.130 | S(O)CCl₂F | H | CH₃ | CH₃ | | |
| 2.131 | S(O)CCl₂F | CH₃ | H | H | | |
| 2.132 | S(O)CCl₂F | CH₃ | CH₃ | H | | |
| 2.133 | S(O)CCl₂F | CH₃ | CH₃ | CH₃ | | |
| 2.134 | S(O)CCl₂F | CH₂CH₃ | H | H | | |
| 2.135 | S(O)CCl₂F | CH₂CH₃ | CH₃ | H | | |
| 2.136 | S(O)CCl₂F | CH₂CH₃ | CH₃ | CH₃ | | |
| 2.137 | S(O)₂CCl₂F | H | H | H | | |
| 2.138 | S(O)₂CCl₂F | H | CH₃ | H | | |
| 2.139 | S(O)₂CCl₂F | H | CH₃ | CH₃ | | |
| 2.140 | S(O)₂CCl₂F | CH₃ | H | H | | |
| 2.141 | S(O)₂CCl₂F | CH₃ | CH₃ | H | | |

TABLE 2-continued

Compounds of formula (Ib)

| Cpd | $R^2$ | $R^8$ | $R^{10}$ | $R^{11}$ | mp (° C.) | RF |
|---|---|---|---|---|---|---|
| 2.142 | $S(O)_2CCl_2F$ | $CH_3$ | $CH_3$ | $CH_3$ | | |
| 2.143 | $S(O)_2CCl_2F$ | $CH_2CH_3$ | H | H | | |
| 2.144 | $S(O)_2CCl_2F$ | $CH_2CH_3$ | $CH_3$ | H | | |
| 2.145 | $S(O)_2CCl_2F$ | $CH_2CH_3$ | $CH_3$ | $CH_3$ | | |

TABLE 3

Compounds of formula (Ic)

| Cpd | $R^2$ | $R^3$ | $R^6$ | $R^7$ | mp (° C.) | RF |
|---|---|---|---|---|---|---|
| 3.1 | $SCF_3$ | Br | H | H | | |
| 3.2 | $SCF_3$ | OH | H | H | 198 | 0.05 |
| 3.3 | $SCF_3$ | $OCH_2CH_3$ | H | H | 161 | 0.09 |
| 3.4 | $SCF_3$ | $OCH_2CH_3$ | $SCH(CH_3)_2$ | H | wax | 0.92 |
| 3.5 | $SCF_3$ | $OCH_3$ | H | H | | |
| 3.6 | $SCF_3$ | $OCH_2CH=CH_2$ | H | H | | |
| 3.7 | $SCF_3$ | $N(CH_3)_2$ | H | H | | |
| 3.8 | $SCF_3$ | $N(CH_3)COCH_3$ | H | H | | |
| 3.9 | $SCF_3$ | $N(CH_3)CO_2CH_3$ | H | H | | |
| 3.10 | $S(O)CF_3$ | Br | H | H | 179 | 0.92 |
| 3.11 | $S(O)CF_3$ | OH | H | H | | |
| 3.12 | $S(O)CF_3$ | $OCH_2CH_3$ | H | H | | |
| 3.13 | $S(O)CF_3$ | $OCH_2CH_3$ | $SCH(CH_3)_2$ | H | | |
| 3.14 | $S(O)CF_3$ | $OCH_3$ | H | H | | |
| 3.15 | $S(O)CF_3$ | $OCH_2CH=CH_2$ | H | H | | |
| 3.16 | $S(O)CF_3$ | $N(CH_3)_2$ | H | H | | |
| 3.17 | $S(O)CF_3$ | $N(CH_3)COCH_3$ | H | H | | |
| 3.18 | $S(O)CF_3$ | $N(CH_3)CO_2CH_3$ | H | H | | |
| 3.19 | $S(O)CF_3$ | $N(CH_3)_2$ | cyclopropyl | H | | |
| 3.20 | $S(O)CF_3$ | $N(CH_3)_2$ | $CH_2CH=CH$ | H | | |
| 3.21 | $S(O)CF_3$ | $N(CH_3)_2$ | $CH_2CH=CH_2$ | H | | |
| 3.22 | $S(O)CF_3$ | $N(CH_3)_2$ | $CH_3$ | H | | |
| 3.23 | $S(O)CF_3$ | $N(CH_3)_2$ | $CH_2CH_3$ | H | | |
| 3.24 | $S(O)CF_3$ | $N(CH_3)_2$ | $CH_2CH_2CH_3$ | H | | |
| 3.25 | $S(O)CF_3$ | $N(CH_3)_2$ | $CH(CH_3)_2$ | H | | |
| 3.26 | $S(O)CF_3$ | $N(CH_3)_2$ | $CH_2(CH_2)_3CH_3$ | H | | |
| 3.27 | $S(O)CF_3$ | $N(CH_3)_2$ | cyclohexyl | H | | |
| 3.28 | $S(O)CF_3$ | $N(CH_3)_2$ | $CH_2CH_2OCH_3$ | H | | |

TABLE 3-continued

Compounds of formula (Ic)

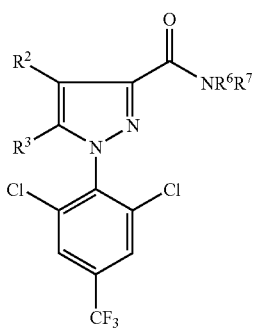

(Ic)

| Cpd | $R^2$ | $R^3$ | $R^6$ | $R^7$ | mp (° C.) | RF |
|---|---|---|---|---|---|---|
| 3.29 | S(O)CF$_3$ | N(CH$_3$)$_2$ | 2-tetrahydrofurfuryl | H | | |
| 3.30 | S(O)CF$_3$ | N(CH$_3$)$_2$ | 2-furfuryl | H | | |
| 3.31 | S(O)CF$_3$ | N(CH$_3$)$_2$ | CH$_2$CN | H | | |
| 3.32 | S(O)CF$_3$ | N(CH$_3$)$_2$ | CH$_2$CH$_2$CN | H | | |
| 3.33 | S(O)CF$_3$ | N(CH$_3$)$_2$ | CH$_2$-cyclopropyl | H | | |
| 3.34 | S(O)CF$_3$ | N(CH$_3$)$_2$ | CH$_2$CH$_2$CH(CH$_3$)$_2$ | H | | |
| 3.35 | S(O)CF$_3$ | N(CH$_3$)$_2$ | CH$_2$CH$_2$N(CH$_3$)$_2$ | H | | |
| 3.36 | S(O)CF$_3$ | N(CH$_3$)$_2$ | CH$_2$CH$_2$CH$_2$OCH$_3$ | H | | |
| 3.37 | S(O)CF$_3$ | N(CH$_3$)$_2$ | CH$_2$CH$_2$SCH$_3$ | H | | |
| 3.38 | S(O)CF$_3$ | N(CH$_3$)$_2$ | CH$_2$CF$_3$ | H | | |
| 3.39 | S(O)CF$_3$ | N(CH$_3$)$_2$ | CH$_2$(CH$_2$)$_2$CH=CH$_2$ | H | | |
| 3.40 | S(O)CF$_3$ | N(CH$_3$)$_2$ | CH$_2$(CH$_2$)$_4$CH$_3$ | H | | |
| 3.41 | S(O)CF$_3$ | N(CH$_3$)$_2$ | CH$_2$(CH$_2$)$_2$SCH$_3$ | H | | |
| 3.42 | S(O)CF$_3$ | N(CH$_3$)$_2$ | CH$_2$C$_6$H$_5$ | H | | |
| 3.43 | S(O)CF$_3$ | N(CH$_3$)$_2$ | CH$_2$-3-pyridyl | H | | |
| 3.44 | S(O)CF$_3$ | N(CH$_3$)$_2$ | 5-CH$_3$-furfur-2-yl | H | | |
| 3.45 | S(O)CF$_3$ | N(CH$_3$)$_2$ | CH$_2$-thiophen-2-yl | H | | |
| 3.46 | S(O)CF$_3$ | N(CH$_3$)$_2$ | CH$_2$CH$_2$C$_6$H$_5$ | H | | |
| 3.47 | S(O)CF$_3$ | N(CH$_3$)$_2$ | CH$_2$CH$_2$-3-pyridyl | H | | |
| 3.48 | S(O)CF$_3$ | N(CH$_3$)$_2$ | CH$_2$(CH$_2$)$_2$-N-imidazolyl | H | | |
| 3.49 | S(O)CF$_3$ | N(CH$_3$)$_2$ | cyclopropyl | CH$_3$ | | |
| 3.50 | S(O)CF$_3$ | N(CH$_3$)$_2$ | CH$_2$CH=CH | CH$_3$ | | |
| 3.51 | S(O)CF$_3$ | N(CH$_3$)$_2$ | CH$_2$CH=CH$_2$ | CH$_3$ | | |
| 3.52 | S(O)CF$_3$ | N(CH$_3$)$_2$ | CH$_3$ | CH$_3$ | | |
| 3.53 | S(O)CF$_3$ | N(CH$_3$)$_2$ | CH$_2$CH$_3$ | CH$_3$ | | |
| 3.54 | S(O)CF$_3$ | N(CH$_3$)$_2$ | CH$_2$CH$_2$CH$_3$ | CH$_3$ | | |
| 3.55 | S(O)CF$_3$ | N(CH$_3$)$_2$ | CH(CH$_3$)$_2$ | CH$_3$ | | |
| 3.56 | S(O)CF$_3$ | N(CH$_3$)$_2$ | CH$_2$(CH$_2$)$_3$CH$_3$ | CH$_3$ | | |
| 3.57 | S(O)CF$_3$ | N(CH$_3$)$_2$ | cyclohexyl | CH$_3$ | | |
| 3.58 | S(O)CF$_3$ | N(CH$_3$)$_2$ | CH$_2$CH$_2$OCH$_3$ | CH$_3$ | | |
| 3.59 | S(O)CF$_3$ | N(CH$_3$)$_2$ | 2-tetrahydrofurfuryl | CH$_3$ | | |
| 3.60 | S(O)CF$_3$ | N(CH$_3$)$_2$ | 2-furfuryl | CH$_3$ | | |
| 3.61 | S(O)CF$_3$ | N(CH$_3$)$_2$ | CH$_2$CN | CH$_3$ | | |
| 3.62 | S(O)CF$_3$ | N(CH$_3$)$_2$ | CH$_2$CH$_2$CN | CH$_3$ | | |
| 3.63 | S(O)CF$_3$ | N(CH$_3$)$_2$ | CH$_2$-cyclopropyl | CH$_3$ | | |
| 3.64 | S(O)CF$_3$ | N(CH$_3$)$_2$ | CH$_2$CH$_2$CH(CH$_3$)$_2$ | CH$_3$ | | |
| 3.65 | S(O)CF$_3$ | N(CH$_3$)$_2$ | CH$_2$CH$_2$N(CH$_3$)$_2$ | CH$_3$ | | |
| 3.66 | S(O)CF$_3$ | N(CH$_3$)$_2$ | CH$_2$CH$_2$CH$_2$OCH$_3$ | CH$_3$ | | |
| 3.67 | S(O)CF$_3$ | N(CH$_3$)$_2$ | CH$_2$CH$_2$SCH$_3$ | CH$_3$ | | |
| 3.68 | S(O)CF$_3$ | N(CH$_3$)$_2$ | CH$_2$CF$_3$ | CH$_3$ | | |
| 3.69 | S(O)CF$_3$ | N(CH$_3$)$_2$ | CH$_2$(CH$_2$)$_2$CH=CH$_2$ | CH$_3$ | | |
| 3.70 | S(O)CF$_3$ | N(CH$_3$)$_2$ | CH$_2$(CH$_2$)$_4$CH$_3$ | CH$_3$ | | |
| 3.71 | S(O)CF$_3$ | N(CH$_3$)$_2$ | CH$_2$(CH$_2$)$_2$SCH$_3$ | CH$_3$ | | |
| 3.72 | S(O)CF$_3$ | N(CH$_3$)$_2$ | CH$_2$C$_6$H$_5$ | CH$_3$ | | |
| 3.73 | S(O)CF$_3$ | N(CH$_3$)$_2$ | CH$_2$-3-pyridyl | CH$_3$ | | |
| 3.74 | S(O)CF$_3$ | N(CH$_3$)$_2$ | 5-CH$_3$-furfur-2-yl | CH$_3$ | | |
| 3.75 | S(O)CF$_3$ | N(CH$_3$)$_2$ | CH$_2$-thiophen-2-yl | CH$_3$ | | |
| 3.76 | S(O)CF$_3$ | N(CH$_3$)$_2$ | CH$_2$CH$_2$C$_6$H$_5$ | CH$_3$ | | |
| 3.77 | S(O)CF$_3$ | N(CH$_3$)$_2$ | CH$_2$CH$_2$-3-pyridyl | CH$_3$ | | |
| 3.78 | S(O)CF$_3$ | N(CH$_3$)$_2$ | CH$_2$(CH$_2$)$_2$—N—imidazolyl | CH$_3$ | | |
| 3.79 | S(O)CF$_3$ | N(CH$_3$)$_2$ | CH$_2$CH$_3$ | CH$_2$CH$_3$ | | |
| 3.80 | S(O)CF$_3$ | N(CH$_3$)$_2$ | —CH$_2$(CH$_2$)$_2$CH$_2$— | | | |
| 3.81 | S(O)CF$_3$ | N(CH$_3$)$_2$ | —CH$_2$(CH$_2$)$_3$CH$_2$— | | | |
| 3.82 | S(O)CF$_3$ | N(CH$_3$)$_2$ | —CH$_2$CH$_2$OCH$_2$CH$_2$— | | | |
| 3.83 | S(O)CF$_3$ | N(CH$_3$)$_2$ | —CH$_2$CH$_2$N(CH$_3$)CH$_2$CH$_2$— | | | |

TABLE 3-continued

Compounds of formula (Ic)

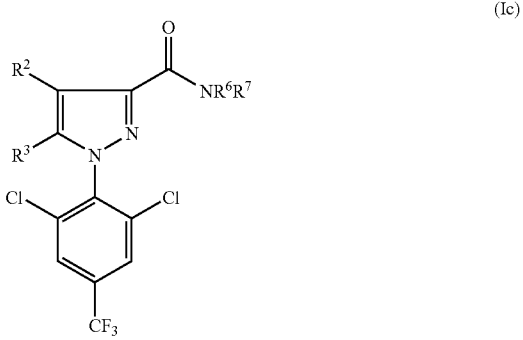

| Cpd | $R^2$ | $R^3$ | $R^6$ | $R^7$ | mp (° C.) | RF |
|---|---|---|---|---|---|---|
| 3.84 | $S(O)_2CF_3$ | Br | H | H | | |
| 3.85 | $S(O)_2CF_3$ | CH | H | H | | |
| 3.86 | $S(O)_2CF_3$ | $OCH_2CH_3$ | H | H | | |
| 3.87 | $S(O)_2CF_3$ | $OCH_2CH_3$ | $SCH(CH_3)_2$ | H | | |
| 3.88 | $S(O)_2CF_3$ | $OCH_3$ | H | H | | |
| 3.89 | $S(O)_2CF_3$ | $OCH_2CH=CH_2$ | H | H | | |
| 3.90 | $S(O)_2CF_3$ | $N(CH_3)_2$ | H | H | | |
| 3.91 | $S(O)_2CF_3$ | $N(CH_3)COCH_3$ | H | H | | |
| 3.92 | $S(O)_2CF_3$ | $N(CH_3)CO_2CH_3$ | H | H | | |

Another aspect of the invention is a method for plant growth regulation which plants are monocotyledoneous or dicotyledoneous crop plants, preferably selected from the group of economically important field crops such as, for example wheat, barley, rye, triticale, rice, maize, sugar beet, cotton, or soybeans, particularly maize, wheat, and soybean, as well as vegetables and ornamentals, said method comprising applying to said plants, to the seeds from which they grow or to the locus in which they grow, a non-phytotoxic, effective plant growth regulating amount of one or more compounds of formula (I).

A further aspect of the invention is a method for plant growth regulation, which plants are monocotyledoneous or dicotyledoneous crop plants, preferably selected from the group of economically important field crops such as, for example wheat, barley, rye, triticale, rice, maize, sugar beet, cotton, or soybeans, particularly maize, wheat, and soybean, as well as vegetables and ornamentals, said method comprising applying to said plants, to the seeds from which they grow or to the locus in which they grow, a non-phytotoxic, effective plant growth regulating amount of a compound having the formula (I) in a mixture with carriers and/or surfactants.

A further aspect of the invention is a method for plant growth regulation, which plants are monocotyledoneous or dicotyledoneous crop plants, preferably selected from the group of economically important field crops such as, for example wheat, barley, rye, triticale, rice, maize, sugar beet, cotton, or soybeans, particularly maize, wheat, and soybean, as well as vegetables and ornamentals, said method comprising applying to said plants, to the seeds from which they grow or to the locus in which they grow, a non-phytotoxic, effective plant growth regulating amount of a compound having the formula (I) together with a further active compound selected from the group consisting of acaricides, fungicides, herbicides, insecticides, nematicides or plant growth regulating substances not identical to compounds defined by formula (I). In case that it is intended to apply the compound having formula (I) either alone or together with a further active compound directly to the seed, there are several ways on how to perform such seed treatment, like by "filmcoating" which is characterized by the creation of a liquid formulation containing an applicable polymer which will be applied to the seed, thereby improving the adherence, the coverage and the distribution of the compounds on the seed.

Among the further active compounds to be applied together with a compound having the formula (I), either applied as one further active compound or applied in a combination of several further active compounds, the following compounds are specifically named as examples of such further active compounds: 2-Phenylphenol; 8-Hydroxyquinoline sulfate; Acibenzolar-S-methyl; Actinovate; Aldimorph; Amidoflumet; Ampropylfos; Ampropylfos-potassium; Andoprim; Anilazine; Azaconazole; Azoxystrobin; Benalaxyl; Benodanil; Benomyl; Benthiavalicarb-isopropyl; Benzamacril; Benzamacril-isobutyl; Bilanafos; Binapacryl; Biphenyl; Bitertanol; Blasticidin-S; Boscalid; Bromuconazole; Bupirimate; Buthiobate; Butylamine; Calcium polysulfide; Capsimycin; Captafol; Captan; Carbendazim; Carboxin; Carpropamid; Carvone; Chinomethionat; Chlobenthiazone; Chlorfenazole; Chloroneb; Chlorothalonil; Chlozolinate; cis-1 -(4-chlorophenyl)-2-(1H-1,2,4-triazole-1-yl)-cycloheptanol; Clozylacon; Cyazofamid; Cyflufenamid; Cymoxanil; Cyproconazole; Cyprodinil; Cyprofuram; Dagger G; Debacarb; Dichlofluanid; Dichlone; Dichlorophen; Diclocymet; Diclomezine; Dicloran; Diethofencarb; Difenoconazole; Diflumetorim; Dimethirimol; Dimethomorph; Dimoxystrobin; Diniconazole; Diniconazole-M; Dinocap; Diphenylamine; Dipyrithione; Ditalimfos; Dithianon; Dodine; Drazoxolon; Edifenphos; Epoxiconazole; Ethaboxam; Ethirimol; Etridiazole; Famoxadone; Fenamidone; Fenapanil; Fenarimol; Fenbuconazole; Fenfuram; Fenhexamid; Fenitropan; Fenoxanil; Fenpiclonil; Fenpropidin; Fenpropimorph; Ferbam; Fluazinam; Flubenzimine; Fludioxonil; Flumetover; Flumorph; Fluoromide; Fluoxastrobin; Fluquinconazole; Flurprimidol; Flusilazole; Flusulfamide; Flutolanil; Flutriafol; Folpet; Fosetyl-Al; Fosetyl-sodium; Fuberidazole; Furalaxyl; Furametpyr; Furcarbanil; Furmecyclox; Guazatine; Hexachlorobenzene; Hexaconazole; Hymexazol; Imazalil; Imibenconazole; Iminoctadine triacetate; Iminoctadine tris(albesilate); Iodocarb; Ipconazole; Iprobenfos; Iprodione; Iprovalicarb; Irumamycin; Isoprothiolane; Isovaledione; Kasugamycin; Kresoxim-methyl; Mancozeb; Maneb; Meferimzone; Mepanipyrim; Mepronil; Metalaxyl; Metalaxyl-M; Metconazole; Methasulfocarb; Methfuroxam; methyl 1-(2,3-dihydro-2,2-dimethyl-1H-inden-1-yl)-1H-imidazole-5-carboxylate; Methyl 2-[[[cyclopropyl[(4-methoxyphenyl)imino]methyl]thio]methyl]-.alpha.-(methoxymethylene)-benzeneacetate; Methyl 2-[2-[3-(4-chloro-phenyl)-1-methyl-allylideneaminooxymethyl]-phenyl]-3-methoxy-acrylate; Metiram; Metominostrobin; Metrafenone; Metsulfovax; Mildiomycin; monopotassium carbonate; Myclobutanil; Myclozolin; N-(3-Ethyl-3,5,5-trimethyl-cyclohexyl)-3-formylamino-2-hydroxy-benzamide; N-(6-methoxy-3-pyridinyl)-cyclopropanecarboxamide; N-butyl-8-(1,1-dimethylethyl)-1-oxaspiro[4.5]decan-3-amine; Natamycin; Nitrothal-isopropyl; Noviflumuron; Nuarimol; Ofurace; Orysastrobin; Oxadixyl; Oxolinic acid; Oxpoconazole; Oxycarboxin; Oxyfenthiin; Paclobutrazol; Pefurazoate; Penconazole; Pencycuron; Penthiopyrad; Phosdiphen; Phthalide; Picobenzamid; Picoxystrobin; Piperalin; Polyoxins; Polyoxorim; Probenazole; Prochloraz; Procymidone; Propamocarb; Propanosine-sodium; Propiconazole; Propineb; Proquinazid; Prothioconazole; Pyraclostrobin; Pyrazophos; Pyrifenox; Pyrimethanil; Pyroquilon; Pyroxyfur; Pyrrolnitrine; Quinconazole; Quinoxyfen; Quintozene; Silthiofam; Simeconazole; Sodium tetrathiocarbonate; Spiroxamine; Sulfur; Tebuconazole; Tecloftalam; Tecnazene; Tetcyclacis; Tetraconazole; Thiabendazole; Thicyofen; Thifluzamide; Thiophanate-methyl; Thiram; Tiadinil; Tioxymid; Tolclofos-methyl; Tolylfluanid; Triadimefon; Triadimenol; Triazbutil; Triazoxide; Tricyclamide; Tricyclazole; Tridemorph; Trifloxystrobin; Triflumizole; Triforine; Triticonazole; Uniconazole; Validamycin A; Vinclozolin; Zineb; Ziram; Zoxamide; (2S)-N-[2-[4-[[3-(4-chlorophenyl)-2-propynyl]oxy]-3-methoxyphenyl]ethyl]-3-methyl-2-[(methylsulfonyl)amino]-butanamide; 1-(1-naphthalenyl)-1H-pyrrole-2,5-dione; 2,3,5,6-tetrachloro-4-(methylsulfonyl)-pyridine; 2,4-Dihydro-5-methoxy-2-methyl-4-[[[[1-[3-(trifluoromethyl)-phenyl]-ethylidene]-amino]-oxy]-methyl]-phenyl]-3H-1,2,3-triazol-3-one; 2-amino-4-methyl-N-phenyl-5-thiazolecarboxamide; 2-chloro-N-(2,3-dihydro-1,1,3-trimethyl-1H-inden-4-yl)-3-pyridincarboxamide; 3,4,5-trichloro-2,6-pyridinedicarbonitrile; 3-[(3-Bromo-6-fluoro-2-methyl-1H-indol-1-yl)sulfonyl]-N,N-dimethyl-1H-1,2,4-triazole-1-sulfonamide;

Copper salts and Copper preparations, like Bordeaux mixture; Copper hydroxide; Copper naphthenate; Copper oxychloride; Copper sulfate; Cufraneb; Cuprous oxide; Mancopper; Oxine-copper; Alanycarb, Aldicarb, Aldoxycarb, Allyxycarb, Aminocarb, Bendiocarb, Benfuracarb, Bufencarb, Butacarb, Butocarboxim, Butoxycarboxim, Carbaryl, Carbofuran, Carbosulfan, Cloethocarb, Dimetilan, Ethiofencarb, Fenobucarb, Fenothiocarb, Formetanate, Furathiocarb, Isoprocarb, Metam-sodium, Methiocarb, Methomyl, Metolcarb, Oxamyl, Pirimicarb, Promecarb, Propoxur, Thiodicarb, Thiofanox, Trimethacarb, XMC, Xylylcarb, Acephate, Azamethiphos, Azinphos (-methyl, -ethyl), Bromophosethyl, Bromfenvinfos (-methyl), Butathiofos, Cadusafos, Carbopheno-thion, Chlorethoxyfos, Chlorfenvinphos, Chlormephos, Chlorpyrifos (-methyl/-ethyl), Coumaphos, Cyanofenphos, Cyanophos, Chlorfenvinphos, Demeton-S-methyl, Demeton-S-methylsulphon, Dialifos, Diazinon, Dichlofenthion, Dichlorvos/DDVP, Dicrotophos, Dimethoate, Dimethylvinphos, Dioxabenzofos, Disulfoton, EPN, Ethion, Ethoprophos, Etrimfos, Famphur, Fenamiphos, Fenitrothion, Fensulfothion, Fenthion, Flupyrazofos, Fonofos, Formothion, Fosmethilan, Fosthiazate, Heptenophos, Iodofenphos, Iprobenfos, Isazofos, Isofenphos, Isopropyl O-salicylate, Isoxathion, Malathion, Mecarbam, Methacrifos, Methamidophos, Methidathion, Mevinphos, Monocrotophos, Naled, Omethoate, Oxydemeton-methyl, Parathion (-methyl/-ethyl), Phenthoate, Phorate, Phosalone, Phosmet, Phosphamidon, Phosphocarb, Phoxim, Pirimiphos (-methyl/-ethyl), Profenofos, Propaphos, Propetamphos, Prothiofos, Prothoate, Pyraclofos, Pyridaphenthion, Pyridathion, Quinalphos, Sebufos, Sulfotep, Sulprofos, Tebupirimfos, Temephos, Terbufos, Tetrachlorvinphos, Thiometon, Triazophos, Triclorfon, Vamidothion, Acrinathrin, Allethrin (d-cis-trans, d-trans), Beta-Cyfluthrin, Bifenthrin, Bioallethrin, Bioallethrin-S-cyclopentyl-isomer, Bioethanomethrin, Biopermethrin, Bioresmethrin, Chlovaporthrin, Cis-Cypermethrin, Cis-Resmethrin, Cis-Permethrin, Clocythrin, Cycloprothrin, Cyfluthrin, Cyhalothrin, Cypermethrin (alpha-, beta-, theta-, zeta-), Cyphenothrin, Deltamethrin, Empenthrin (1R-isomer), Esfenvalerate, Etofenprox, Fenfluthrin, Fenpropathrin, Fenpyrithrin, Fenvalerate, Flubrocythrinate, Flucythrinate, Flufenprox, Flumethrin, Fluvalinate, Fubfenprox, Gamma-Cyhalothrin, Imiprothrin, Kadethrin, Lambda-Cyhalothrin, Metofluthrin, Permethrin (cis-, trans-), Phenothrin (1R-trans isomer), Prallethrin, Profluthrin, Protrifenbute, Pyresmethrin, Resmethrin, RU 15525, Silafluofen, Tau-Fluvalinate, Tefluthrin, Terallethrin, Tetramethrin (-1R- isomer), Tralomethrin, Transfluthrin, ZXI 8901, Pyrethrins (pyrethrum), DDT, Indoxacarb, Acetamiprid, Clothianidin, Dinotefuran, Imidacloprid, Nitenpyram, Nithiazine, Thiacloprid, Thiamethoxam, Nicotine, Bensultap, Cartap, Camphechlor, Chlordane, Endosulfan, Gamma-HCH, HCH, Heptachlor, Lindane, Methoxychlor Spinosad, Acetoprole, Ethiprole, Fipronil, Vaniliprole, Avermectin, Emamectin, Emamectin-benzoate, Ivermectin, Milbemycin, Diofenolan, Epofenonane, Fenoxycarb, Hydroprene, Kinoprene, Methoprene, Pyriproxifen, Triprene, Chromafenozide, Halofenozide, Methoxyfenozide, Tebufenozide, Bistrifluron, Chlofluazuron, Diflubenzuron, Fluazuron, Flucycloxuron, Flufenoxuron, Hexaflumuron, Lufenuron, Novaluron, Noviflumuron, Penfluron, Teflubenzuron, Triflumuron, Buprofezin, Cyromazine, Diafenthiuron, Azocyclotin, Cyhexatin, Fenbutatin-oxide, Chlorfenapyr, Binapacyrl, Dinobuton, Dinocap, DNOC, Fenazaquin, Fenpyroximate, Pyrimidifen, Pyridaben, Tebufenpyrad, Tolfenpyrad, Hydramethyinon, Dicofol, Rotenone, Acequinocyl, Fluacrypyrim, Bacillus thuringiensis strains, Spirodiclofen, Spiromesifen, 3-(2,5-Dimethylphenyl)-8-methoxy-2-oxo-1-azaspiro[4.5]dec-3-en-4-yl ethyl carbonate (alias: Carbonic acid, 3-(2,5-dimethylphenyl)-8-methoxy-2-oxo-1-azaspiro [4.5]dec-3-en-4-yl ethyl ester, CAS-Reg.-No.: 382608-10-8) and Carbonic acid, cis-3-(2,5-dimethylphenyl)-8-methoxy-2-oxo-1-azaspiro[4.5]dec-3-en-4-yl ethyl ester (CAS-Reg.-No.: 203313-25-1), Flonicamid, Amitraz, Propargite, N2-[1,1-Dimethyl-2-(methylsulfonyl)ethyl]-3-iodo-N 1 -[2-methyl-4-[1,2,2,2-tetrafluoro-1-(trifluoromethyl)ethyl] phenyl]-1,2-benzenedicarboxamide (CAS-Reg.-No.: 272451-65-7), Thiocyclam hydrogen oxalate, Thiosultap-sodium, Azadirachtin, *Bacillus* spec., *Beauveria* spec., *Codlemone*, *Metarrhizium* spec., *Paecilomyces* spec., *Thuringiensin, Verticillium* spec., Aluminium phosphide, Methyl bromide, Sulfuryl fluoride, Cryolite, Flonicamid, Pymetrozine, Clofentezine, Etoxazole, Hexythiazox, Amidoflumet, Benclothiaz, Benzoximate, Bifenazate, Bromopropylate, Buprofezin, Chinomethionat, Chlordimeform, Chlorobenzilate, Chloropicrin, Clothiazoben, Cycloprene, Dicyclanil, Fenoxacrim, Fentrifanil, Flubenzimine, Flufenerim, Flutenzin, Gossyplure, Hydramethylnone, Japonilure, Metoxadiazone, Petroleum, Piperonyl butoxide, Potassium oleate, Pyridalyl, Sulfluramid, Tetradifon, Tetrasul, Triarathene, Verbutin.

Another aspect of the invention is a method for growth regulation in plant tissue cultures of monocotyledoneous or dicotyledoneous plants said method comprising applying to plant tissue cultures an appropriate amount of a compound having the formula (I) either alone or together with at least one further active compound selected from the group of plant growth regulators or plant hormones.

The compounds of formula (I) can preferably be employed as plant growth regulators in crops of useful monocotyledoneous or dicotyledoneous crop plants, preferably selected from the group of economically important field crops such as, for example wheat, barley, rye, triticale, rice, maize, sugar beet, cotton, or soybeans, particularly maize, wheat, and soybean, as well as vegetables and ornamentals that have been rendered thus by means of genetic engineering.

Traditional ways of generating novel plants which have modified characteristics in comparison with existing plants consist, for example, in traditional breeding methods and the generation of mutants. However, it is also possible to generate novel plants with altered characteristics with the aid of genetic engineering methods (see, for example, EP-A-0221044, EP-A-0131624). For example, several cases have been described of genetic engineering modifications of crop plants with the purpose of modifying the starch synthesized in the plants (for example WO 92/11376, WO 92/14827, WO 91/19806), transgenic crop plants which are resistant to certain herbicides of the glufosinate type (cf., for example, EP-A-0242236, EP-A-242246) or the glyphosate type (WO 92/00377) or the sulfonylurea type (EP-A-0257993, U.S. Pat. No. 5,013,659), transgenic crop plants, for example cotton, which are capable of producing *Bacillus thuringiensis* toxins (Bt toxins) which make the plants resistant to specific pests (EP-A-0142924, EP-A-0193259), transgenic crop plants whose fatty acid spectrum is modified (WO 91/13972).

A large number of techniques in molecular biology by means of which novel transgenic plants with altered characteristics can be generated are known in principle; see, for example, Sambrook et al., 1989, Molecular Cloning, A Laboratory Manual, 2nd Ed., Cold Spring Harbor Laboratory Press, Cold Spring Harbor, N.Y.; or Winnacker "Gene und Klone" [Genes and Clones], VCH Weinheim 2nd Edition 1996, or Christou, "Trends in Plant Science" 1 (1996) 423-431).

In order to perform such genetic engineering manipulations, nucleic acid molecules may be introduced into plasmids which allow mutagenesis or a sequence change by means of recombination of DNA sequences. It is possible, for example, with the aid of the abovementioned standard methods to perform base exchanges, to remove subsequences or to add natural or synthetic sequences. To connect the DNA fragments to each other, adaptors or linkers may be attached to the fragments.

For example, plant cells with a reduced activity of a gene product can be generated by expressing at least one corresponding antisense RNA, a sense RNA to achieve a cosuppressory effect or by expressing at least one ribozyme of suitable construction which specifically cleaves transcripts of the abovementioned gene product.

To this end it is possible to make use of, on the one hand, DNA molecules which encompass the entire coding sequence of a gene product inclusive of any flanking sequences which may be present, on the other hand DNA molecules which only encompass parts of the coding sequence, but these parts must be long enough in order to effect, in the cells, an antisense effect. Use may also be made of DNA sequences which show a high degree of homology to the coding sequences of a gene product, but which are not completely identical.

When nucleic acid molecules are expressed in plants, the protein which has been synthesized may be located in any desired compartment of the plant cell. However, to achieve localization in a particular compartment, it is possible, for example, to link the coding region with DNA sequences which guarantee localization in a particular compartment. Such sequences are known to the skilled worker (see, for example, Braun et al., EMBO J. 11 (1992), 3219-3227; Wolter et al., Proc. Natl. Acad. Sci. USA 85 (1988), 846-850; Sonnewald et al., Plant J.1 (1991), 95-106).

The transgenic plant cells may be regenerated by known techniques to give complete plants. In principle, the transgenic plants can be plants of any desired plant species, that is to say monocotyledonous and also dicotyledonous plants.

This allows transgenic plants to be obtained which exhibit altered characteristics by means of overexpression, suppression or inhibition of homologous (=natural) genes or gene sequences or by means of expression of heterologous (=foreign) genes or gene sequences.

The compounds of formula (I) can preferably be employed in transgenic crops which are resistant to herbicides from the group of the sulfonylureas, glufosinate-ammonium or glyphosate-isopropylammonium and analogous active substances or in analogous showing altered phenotypes, like but not limited to features as for content modification, altered flowering time, male or female sterile plants, environmentally resistant plants due to expression or repression of endogenous or exogenous genes in the transgenic crop.

The use according to the invention for plant growth regulation also includes the case where the compounds of formula (I) are only formed in the plant or the soil from a precursor ("prodrug") after its application to the plant.

The compounds of formula (I) can be employed in the conventional preparations as wettable powders, emulsifiable concentrates, sprayable solutions, dusts or granules. The invention therefore also relates to plant growth regulating compositions which comprise compounds of formula (I).

According to a further feature of the present invention, there is provided a plant growth regulating composition comprising an effective amount of a compound of formula (I) as defined above or an agriculturally acceptable salt thereof, in association with, and preferably homogeneously dispersed in, one or more compatible agriculturally-acceptable diluents or carriers and/or surface active agents [i.e. diluents or carriers and/or surface active agents of the type generally accepted in the art as being suitable for use in herbicidal compositions and which are compatible with compounds of the invention]. The term "homogeneously dispersed" is used to include compositions in which the compounds of formula (I) are dissolved in other components. The term "growth regulating composition" is used in a broad sense to include not only compositions which are ready for use as herbicides but also concentrates which must be diluted before use (including tank mixtures).

The compounds of formula (I) can be formulated in various ways, depending on the prevailing biological and/or chemico-physical parameters. Examples of possible formulations which are suitable are: wettable powders (WP), water-soluble powders (SP), water-soluble concentrates, emulsifiable concentrates (EC), emulsions (EW) such as oil-in-water and water-in-oil emulsions, sprayable solutions, suspension concentrates (SC), dispersions on an oil or water basis, solutions which are miscible with oil, capsule suspensions (CS), dusts (DP), seed-dressing products, granules for broadcasting and soil application, granules (GR) in the form of microgranules, spray granules, coated granules and adsorption granules, water-dispersible granules (WG), water-soluble granules (SG), ULV formulations, microcapsules and waxes.

These individual formulation types are known in principle and described, for example, in: Winnacker-Küchler, "Chemische Technologie" [Chemical Technology], Volume 7, C. Hauser Verlag, Munich, 4th Edition 1986; Wade van Valkenburg, "Pesticide Formulations", Marcel Dekker, N.Y., 1973; K. Martens, "Spray Drying Handbook", 3rd Ed. 1979, G. Goodwin Ltd. London.

The necessary formulation auxiliaries such as inert materials, surfactants, solvents and other additives are also known and described, for example, in: Watkins, "Handbook of Insecticide Dust Diluents and Carriers", 2nd Ed., Darland Books, Caldwell N.J.; H. v. Olphen, "Introduction to Clay Colloid Chemistry", 2nd Ed., J. Wiley & Sons, N.Y.; C. Marsden, "Solvents Guide", 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-active ethylene oxide adducts], Wiss. Verlagsgesell., Stuttgart 1976; Winnacker-Küchler, "Chemische Technologie" [Chemical Technology], Volume 7, C. Hauser Verlag, Munich, 4th Ed. 1986.

Based on these formulations, it is also possible to prepare combinations with pesticidally active substances such as, for example, insecticides, acaricides, herbicides, fungicides, and with safeners, fertilizers and/or growth regulators, for example in the form of a readymix or a tank mix.

Wettable powders are preparations which are uniformly dispersible in water and which, besides the compounds of formula (I), also comprise ionic and/or nonionic surfactants (wetters, dispersants), for example, polyoxyethylated alkylphenols, polyoxyethylated fatty alcohols, polyoxyethylated fatty amines, fatty alcohol polyglycol ether sulfates, alkanesulfonates or alkylbenzenesulfonates, sodium lignosulfonate, sodium 2,2'-dinaphthylmethane-6,6'-disulfonate, sodium dibutyinaphthalenesulfonate or else sodium oleoylmethyltaurinate, in addition to a diluent or inert substance. To prepare the wettable powders, the compounds of formula (I) are, for example, ground finely in conventional apparatuses such as hammer mills, blower mills and air-jet mills and mixed with the formulation auxiliaries, either concomitantly or thereafter.

Emulsifiable concentrates are prepared, for example, by dissolving the compounds of formula (I) in an organic solvent, for example butanol, cyclohexanone, dimethylformamide, xylene or else higher-boiling aromatics or hydrocarbons or mixtures of these, with addition of one or more ionic and/or nonionic surfactants (emulsifiers). Emulsifiers which can be used are, for example: calcium salts of alkylarylsulfonic acids, such as calcium dodecylbenzenesulfonate or nonionic emulsifiers, such as fatty acid polyglycol esters, alkylaryl polyglycol ethers, fatty alcohol polyglycol ethers, propylene oxide/ethylene oxide condensates, alkyl poly-ethers, sorbitan esters such as sorbitan fatty acid esters or polyoxyethylene sorbitan esters such as polyoxyethylene sorbitan fatty acid esters.

Dusts are obtained by grinding the active substance with finely divided solid substances, for example talc or natural clays, such as kaolin, bentonite or pyrophyllite, or diatomaceous earth.

Suspension concentrates may be water- or oil-based. They can be prepared, for example, by wet grinding by means of commercially available bead mills, if appropriate with addition of surfactants, as they have already been mentioned above for example in the case of the other formulation types.

Emulsions, for example oil-in-water emulsions (EW), can be prepared for example by means of stirrers, colloid mills and/or static mixtures using aqueous organic solvents and, if appropriate, surfactants as they have already been mentioned above for example in the case of the other formulation types.

Granules can be prepared either by spraying the compounds of formula (I) onto adsorptive, granulated inert material or by applying active substance concentrates onto the surface of carriers such as sand, kaolinites or of granulated inert material, by means of binders, for example polyvinyl alcohol, sodium polyacrylate or alternatively mineral oils. Suitable active substances can also be granulated in the manner which is conventional for the production of fertilizer granules, if desired in a mixture with fertilizers.

Water-dispersible granules are prepared, as a rule, by the customary processes such as spray-drying, fluidized-bed granulation, disk granulation, mixing in high-speed mixers and extrusion without solid inert material. To prepare disk, fluidized-bed, extruder and spray granules, see, for example, processes in "Spray-Drying Handbook" 3rd ed. 1979, G. Goodwin Ltd., London; J. E. Browning, "Agglomeration", Chemical and Engineering 1967, pages 147 et seq.; "Perry's Chemical Engineer's Handbook", 5th Ed., McGraw-Hill, New York 1973, p. 8-57.

For further details on the formulation of crop protection products, see, for example, G. C. Klingman, "Weed Control as a Science", John Wiley and Sons, Inc., New York, 1961, pages 81-96 and J. D. Freyer, S. A. Evans, "Weed Control Handbook", 5th Ed., Blackwell Scientific Publications, Oxford, 1968, pages 101-103.

As a rule, the agrochemical preparations comprise 0.1 to 99% by weight, in particular 0.1 to 95% by weight, of compounds of formula (I).

The concentration of compounds of formula (I) in wettable powders is, for example, approximately 10 to 90% by weight, the remainder to 100% by weight being composed of customary formulation components. In the case of emulsifiable concentrates, the concentration of compounds of formula (I) can amount to approximately 1 to 90, preferably 5 to 80% by weight. Formulations in the form of dusts usually comprise 1 to 30% by weight of compounds of formula (I), preferably in most cases 5 to 20% by weight of compounds of formula (I), while sprayable solutions comprise approximately 0.05 to 80, preferably 2 to 50% by weight of compounds of formula (I). In the case of water-dispersible granules, the content of compounds of formula (I) depends partly on whether the compounds of formula (I) are in liquid or solid form and on which granulation auxiliaries, fillers and the like are being used. The water-dispersible granules, for example, comprise between 1 and 95% by weight of active substance, preferably between 10 and 80% by weight.

In addition, the formulations of compounds of formula (I) mentioned comprise, if appropriate, the adhesives, wetters, dispersants, emulsifiers, penetrants, preservatives, antifreeze agents, solvents, fillers, carriers, colorants, antifoams, evaporation inhibitors, pH regulators and viscosity regulators which are conventional in each case.

Suitable formulations for plant growth regulating compositions are known. A description of suitable formulations which may be used in the method of the invention can be found in international patent publications WO 87/3781, WO 93/6089, and WO 94/21606 as well as in European patent application EP 295117, and U.S. Pat. No. 5,232,940. Formulations or compositions for plant growth regulating uses can be made in a similar way, adapting the ingredients, if necessary, to make them more suitable to the plant or soil to which the application is to be made.

The compounds of the formula (I) or their salts can be employed as such or in the form of their preparations (formulations) as combinations with other pesticidally active substances, such as, for example, insecticides, acaricides, nematicides, herbicides, fungicides, safeners, fertilizers and/or further growth regulators, for example as a premix or as tank mixes.

It has been found that, surprisingly, the compounds of formula (I) and most especially compounds 1.1; 1.2; 1.3; 1.4; 1.5; 1.6; 1.7; 1.8; 1.9; 1.10; 1.11; 1.12; 1.13; 1.34; 1.35; 1.36; 1.37; 1.65; 1.96; 1.123; 1.133; 1.134; 1.135; 1.136; 1.137; 1.138; 1.139; 1.140; 1.141; 1.142; 1.143; 1.144; 1.145; 1.166; 1.167; 1.168; 1.169; 1.197; 1.228; 1.255; 1.268; 1.3291.399; 1.400; 1.461; 1.532; 1.664; 1.796; 2.1; 2.10; 2.11; 3.2; 3.3; 3.4; and 3.10 display a significant role concerning plant growth properties, which can be different due to an application at various crops. For example, compound 1.136 show significant effects of approximately the same size by being used as plant growth regulator in maize and wheat but at different concentration. Compound 1.141 shows a remarkable effect as plant growth regulator in maize and a superior effect in wheat.

By virtue of the practice of the present invention a wide variety of plant growth responses, including the following (non-ranked listing), may be induced:
 a) more developed root system
 b) tillering increase
 c) increase in plant height
 d) bigger leaf blade
 e) less dead basal leaves
 f) stronger tillers
 g) greener leaf color
 h) less fertilizers needed
 i) less seeds needed
 j) more productive tillers
 k) less third non-productive tillers
 l) earlier flowering
 m) early grain maturity
 n) less plant verse (lodging)
 o) longer panicles
 p) increased shoot growth
 q) improved plant vigour
 r) early germination
 s) more fruit and better yield It is intended that as used in the instant specification the term "method for plant growth regulation" or "method for plant growth regulation" means the achievement of any of the aforementioned nineteen categories of response or any other modification of plant, seed, fruit or vegetable (whether the fruit or vegetable is nor harvested or harvested) so long as the net result is to increase growth or benefit any property of the plant, seed, fruit or vegetable as distinguished from any pesticidal action (unless the present invention is practised in conjunction with or in the presence of a pesticide, for example a herbicide). The term "fruit" as used in the instant specification is to be understood as meaning anything of economic value that is produced by the plant.

Preferably, at least an increase of 10% of one or more of the respective plant growth response is obtained.

The 5-amino-1-arylpyrazole-3-carbocylic acid derivative of formula (I) may be applied for plant growth regulating purposes to the foliage of plants and/or to the soil in which said plants are growing. Applications to the soil are often in the form of granules which are usually applied in sufficient amount to provide a rate of from about 0.00001 kg/ha to about 0.5 kg/ha of active ingredient, preferably between 0.00001 and 0.1 kg/ha, more preferably between 0.00001 kg/ha and 0.01 kg/ha.

A preferred embodiment of the invention is a method for plant growth regulation comprising applying to the seeds from which said plants grow, prior to said seeds, a non-phytotoxic, effective plant growth regulating amount of a compound having the formula (I). The seed may be treated, especially by coating or embedding or impregnation or soaking or dipping in liquid or paste formulations which are known per se and are subsequently dried. Seed comprising 0.1 to 1000 gram per 100 kg of a compound of formula (I), preferably 0.1 to 800 g per 100 kg, most preferably 0.1 to 250 g per 100 kg are particularly appropriate for this purpose.

The precise amount of 5-amino-1-arylpyrazole-3-carbocylic acid derivative of formula (I) to be used will depend, inter alia, upon the particular plant species being treated. A suitable dose may be determined by the man skilled in the art by routine experimentation. The plant response will depend upon the total amount of compound used, as well as the particular plant species which is being treated. Of course, the amount of 5-amino-1-arylpyrazole-3-carbocylic acid derivative of formula (I) should be non-phytotoxic with respect to the plant being treated.

Although the preferred method of application of the compounds used in the process of this invention is directly to the foliage and stems of plants, the compounds can be applied to the soil in which the plants are growing.

The following examples are illustrative of methods of plant growth regulation according to the invention, but should not be understood as limiting the invention as modifications in materials and methods will be apparent to the skilled worker. All measurements of plant growth regulating effects were determined either by using a protoplast screening assay and/or by using a root growth assay and/or by applying the compounds pre-selected the before defined assay system under natural growth conditions in field trials. In all cases, untreated protoplasts, plants or plants parts, or seeds were taken as a control.

B. BIOLOGICAL EXAMPLES

Example 1

Plant Protoplast System

The present invention features a so called high throughput assay for a rapid screening of chemical compounds that modulate cell growth. The assay in general involves: a) plant protoplasts grown in liquid medium, b) a library of chemical compounds, and c) screening the protoplasts to identify the compounds which affect significantly the cell growth and development.

Protoplast Preparation:
Preferably the protoplasts were prepared from cell suspensions derived from maize callus. The protoplasts were obtained by enzymatic digestion of the cell aggregates in the suspension. The cells were digested for 3-6 hours at room temperature in a cellulase-pectolyase mix, Protoplasts were released by gentle shaking, filtered through a 45 µm mesh and collected by centrifugation. After digestion, the protoplasts were washed several times to remove cell debris and enzyme residues and then re-suspended in culture medium. The protoplasts were plated in 50-100 µl aliquots in microtiter wells at a density ranging from 100.000-2,000.000 protoplasts per ml, preferably at a concentration of 800.000 protoplasts/ml.

Screening Assay:

To identify chemical compounds that modulate the cell growth, maize protoplasts were incubated with a library of chemical compounds in 96-well microtiter plates. Following the incubation at 25° C. for 1-14 days, preferably 7-10 days, the protein content was measured by Coomassie dye based colorimetric assays. The growth of the cells treated with the chemical compounds involved in the test was detected by comparison with untreated protoplasts.

Treatment with a section of compounds derived from formula (I) show an increase of more than 50% over the untreated control.

Example 2

Root Growth Assay

Plant roots are a highly proliferative tissue that allows an easy accessible, cheap and short term screening method for plant growth regulators. The results obtained can easily be transferred to the overall effects on a plant of plant growth regulators identified by such a system. By using this root assay one is enabled to determine the effect of a seed treatment to root growth and/or germination and/or changes in habitat of germinated plants in order to identify the possible use as a yield enhancer. Two seeds of wheat (*Triticum aestivum*, variety "TRISO") or 1 seed of maize (*Zea mays*, variety "LORENZO") per hole in a plastic tray which contains an architecture of 8×13 holes were placed on compost soil covered with sand. These seeds were treated with 100 µl/ hole, which creates an application volume of approx. 1200 l/ha, of a compound solution at active ingredient rates equivalent to 100, 10 and 1 g a.i./ha of each compound using an robotic application system (Lizzy Spray Robotics). Six replicates in a row of each compound and concentration were done. The outer rim of the above defined plastic tray was untreated to avoid false negative effects and the middle row (No. 7) was used as untreated control. The treated seeds were allowed to dry for approx. 4 hours and subsequently covered with sand and watered. The trays were stored in climate chambers with 14 hours lighting at a temperature of 24° C. (±2) at daytime and 16° C. (±2) at night and relative humidity (rH) of 60% and daily watered. Assessments were done 16 (±2) days post treatment by counting the germinated plants and assessing the phytotoxicity symptoms and percentage. In addition, the roots were washed out and the shoots were cut directly above the seed and the wet roots were placed on dry paper towels for approximately 30 minutes and weighted afterwards. This procedure provides a similar grade of moisture to the roots so that a comparison of the weights is possible.

Table 4 shows the results of some of the compounds (Cpd) claimed to be effective in plant growth regulation concerning maize. The effects observed concerning Root Growth given in column 2 (Root Growth of "100" is set as the standard) are directed to concentrations that are equivalent to 100, 10, 1 g a.i./ha, each.

TABLE 4

| | Maize (concentration g a.i./ha) | | |
|---|---|---|---|
| Cpd | 100 | 10 | 1 |
| 1.136 | 74 | 131 | 107 |
| 1.141 | 95 | 102 | 111 |
| 1.228 | 186 | 111 | 72 |

Table 5 shows the results of some of the compounds (Cpd) claimed to be effective in plant growth regulation concerning wheat. The effects observed concerning Root Growth given in column 2 (Root Growth of "100" is set as the standard) are directed to concentrations that are equivalent to 100, 10, 1 g a.i./ha, each.

TABLE 5

| | Wheat (concentration g a.i./ha) | | |
|---|---|---|---|
| Cpd | 100 | 10 | 1 |
| 1.136 | 58 | 75 | 124 |
| 1.144 | 110 | 115 | 170 |
| 1.141 | 256 | 160 | 257 |
| 2.10 | 134 | 118 | 158 |

Example 3

Field Trial

Maize seeds of maize hybrid Magister and Zamora were seed treated with compound 1.136 at 1 g/100 kg seeds (0.0003 kg/ha).

Field trials were set up in a split plot design representing the plants treated with compounds of formula (I) as well as the non-treated control plants.

Results showed an increase in grain yield of up to 119% in case of the hybrid Magister and of up to 131 % in case of the hybrid Zamora compared to the yield obtained with an non-treated control plants in each case.

The invention claimed is:

1. A compound as defined by formula (I), or a salt thereof,

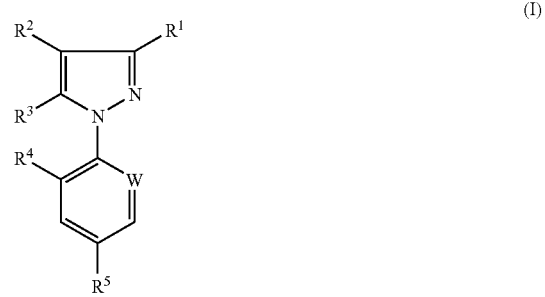

wherein i. $R^1$ is $CO_2R^8$;

$R^2$ is H or $S(O)_mR^9$, wherein m is 0, 1 or 2;

W is C-halogen or N;

$R^3$ is $NR^{10}R^{11}$, halogen, OH, ($C_1$-$C_6$)-alkoxy, ($C_2$-$C_6$)-alkenyloxy or ($C_2$-$C_6$)-alkynyloxy;

$R^4$ is H or halogen;

$R^5$ is $(C_1-C_4)$-haloalkyl or $(C_1-C_4)$-haloalkoxy;
$R^8$ is H; and
$R^9$ is $(C_2-C_6)$-alkyl or $(C_1-C_6)$-haloalkyl;
or
ii. $R^1$ is $CONR^6R^7$;
$R^6$ is $(C_1-C_6)$-alkyl, $(C_1-C_6)$-haloalkyl, $(C_1-C_6)$-alkoxy-$(C_1-C_6)$-alkyl, $(C_2-C_6)$-alkenyl, $(C_2-C_6)$-haloalkenyl, $(C_2-C_6)$-alkynyl, $(C_2-C_6)$-haloalkynyl, $(C_3-C_7)$-cycloalkyl, $(C_3-C_7)$-cycloalkyl-$(C_1-C_6)$-alkyl, $(C_1-C_6)$-alkoxy, $(C_1-C_6)$-alkylthio, $(CH_2)_nR^{12}$, $(CH_2)_pR^{13}$, $(C_1-C_6)$-alkyl-CN, $(C1-C_6)$-alkyl-$NR^{10}R^{11}$ or $(C_1-C_6)$-alkyl-$S(O)_rR^9$;
$R^7$ is H, $(C_1-C_6)$-alkyl, $(C_3-C_6)$-alkenyl or $C_3-C_6$-alkynyl; or
$R^6$ and $R^7$ together with the attached N atom form a five- or six-membered saturated ring which optionally contains an additional hetero atom in the ring which is selected from O, S and N, the ring being unsubstituted or substituted by one or more radicals selected from the group consisting of halogen, $(C_1-C_6)$-alkyl and $(C_1-C_6)$-haloalkyl; and
$R^2$, $R^3$, $R^4$, $R^5$, $R^7$, $R^9$, and W are as defined above;
$R^{10}$ and $R^{11}$ are each independently H, $(C_1-C_6)$-alkyl, $(C_1-C_6)$-haloalkyl, $(C_2-C_6)$-alkenyl, $(C_2-C_6)$-haloalkenyl, $(C_2-C_6)$-alkynyl, $(C_3-C_6)$-cycloalkyl, $(C_3-C_6)$-cycloalkyl-$(C_1-C_6)$-alkyl, $COR^{14}$ or $CO_2R^{15}$; or
$R^{10}$ and $R^{11}$ together with the attached N atom form a five- or six-membered saturated ring which optionally contains an additional hetero atom in the ring which is selected from O, S and N, the ring being unsubstituted or substituted by one or more radicals selected from the group consisting of halogen, $(C_1-C_6)$-alkyl and $(C_1-C_6)$-haloalkyl;
$R^{12}$ is phenyl unsubstituted or substituted by one or more radicals selected from the group consisting of halogen, $(C_1-C_6)$-alkyl, $(C_1-C_6)$-haloalkyl, $(C_1-C_6)$-alkoxy, $(C_1-C_6)$-haloalkoxy, $CO_2R^{16}$, CN, $NO_2$, $S(O)_qR^9$, $COR^{16}$, $CONR^{16}R^{17}$, $NR^{16}R^{17}$ and OH;
$R^{13}$ is heterocyclyl unsubstituted or substituted by one or more radicals selected from the group consisting of halogen, $(C_1-C_4)$-alkyl, $(C_1-C_4)$-haloalklyl, $(C_1-C_4)$-alkoxy, $(C_1-C_4)$-haloalkoxy, $NO_2$, CN, $CO_2R^{16}$, $S(O)_qR^9$, OH and oxo;
$R^{14}$ and $R^{15}$ are each independently H, $(C_1-C_6)$-alkyl, $(C_1-C_6)$-haloalkyl, $(C_2-C_6)$-alkenyl, $(C_2-C_6)$-haloalkenyl, $(C_2-C_6)$-alkynyl or $(C_1-C_6)$-alkoxy-$(C_1-C_4)$-alkyl;
$R^{16}$ and $R^{17}$ are each independently H, $(C_1-C_6)$-alkyl or $(C_1-C_6)$-haloalkyl;
q and r are each independently 0, 1 or 2;
n and p are each independently 0, 1, 2, 3 or 4; and
each heterocyclyl in the above-mentioned radicals is independently a heterocyclic radical having 3 to 7 ring atoms and 1, 2 or 3 heteroatoms in the ring selected from the group consisting of N, O and S;
provided that when $R^1$ is $CONR^6R^7$, then W is C-halogen;
with the exclusion of the compound wherein:
$R^1$ is $CON(CH_3)_2 R^2$ is $CF_3S$; $R^3$ is OH; $R^4$ is Cl; $R^5$ is $CF_3$; and W is C—Cl.

2. The compound of claim 1, wherein W is C-halogen.
3. The compound of claim 2, wherein $R^4$ is halogen.
4. The compound of claim 3, wherein
$R^1$ is $CONR^6R^7$;
W is C-Cl or C-Br
$R^2$ is $S(O)_mR^9$;
$R^3$ is $NR^{10}R^{11}$, halogen, OH, $(C_1-C_3)$-alkoxy, $(C_2-C_6)$-alkenyloxy or $(C_2-C_6)$-alkynyloxy;
$R^4$ is Cl or Br;
$R^5$ is $CF_3$ or $OCF_3$;
$R^6$ is H, $(C_1-C_4)$-alkyl, $(C_1-C_4)$-haloalkyl, $(C_1-C_3)$-alkoxy-$(C_1-C_3)$-alkyl, $(C_3-C_4)$-alkenyl, $(C_3-C_4)$-haloalkenyl, $(C_3-C_4)$-alkynyl, $(C_3-C_4)$-haloalkynyl, $(C_3-C_6)$-cycloalkyl, $(C_3-C_6)$-cycloalkyl-$(C_1-C_3)$-alkyl, $(C_1-C_3)$-alkoxy, $(C_1-C_3)$-alkylthio, $(CH_2)_nR^{12}$ or $(CH_2)_pR^{13}$;
$R^7$ is H, $(C_1-C_4)$-alkyl, $(C_3-C_4)$-alkenyl or $(C_3-C_4)$-alkynyl; or
$R^6$ and $R^7$ together with the attached N atom form a five- or six-membered saturated ring which optionally contains an additional hetero atom in the ring which is selected from O, S and N, the ring being unsubstituted or substituted by one or more radicals selected from the group consisting of halogen, $(C_1-C_3)$-alkyl and $(C_1-C_3)$-haloalkyl;
$R^9$ is $(C_1-C_3)$-alkyl or $(C_1-C_3)$-haloalkyl;
$R^{10}$ and $R^{11}$ are each independently H, $(C_1-C_3)$-alkyl, $(C_1-C_3)$-haloalkyl, $(C_3-C_4)$-alkenyl, $(C_3-C_4)$-haloalkenyl, $(C_3-C_4)$-alkynyl, $(C_3-C_6)$-cycloalkyl, $(C_3-C_6)$-cycloalkyl-$(C_1-C_3)$-alkyl, $COR^{14}$ or $CO_2R^{15}$; or
$R^{10}$ and $R^{11}$ together with the attached N atom form a five- or six-membered saturated ring which optionally contains an additional hetero atom in the ring which is selected from O,S and N; the ring being unsubstituted or substituted by one or more radicals selected from the group consisting of halogen, $(C_1-C_3)$-alkyl and $(C_1-C_3)$-haloalkyl;
$R^{12}$ is phenyl unsubstituted or substituted by one or more radicals selected from the group consisting of halogen, $(C_1-C_3)$-alkyl, $(C_1-C_3)$-haloalkyl, $(C_1-C_3)$-alkoxy, $(C_1-C_3)$ haloalkoxy, $CO_2R^{16}$, CN, $NO_2$, $S(O)_qR^9$, $COR^{16}$, $CONR^{16}R^{17}$, $NR^{16}R^{17}$ and OH;
$R^{13}$ is heterocyclyl unsubstituted or substituted by one or more radicals selected from the group consisting of halogen, $(C_1-C_3)$-alkyl, $(C_1-C_3)$-haloalkyl, $(C_1-C_3)$-alkoxy, $(C_1-C_3)$-haloalkoxy, $NO_2$, CN, $CO_2R^{16}$, $S(O)_qR^9$, OH and oxo;
$R^{14}$ and $R^{15}$ are each independently H, $(C_1-C_3)$-alkyl, $(C_1-C_3)$-haloalkyl, $(C_2-C_3)$-alkenyl, $(C_2-C_3)$-haloalkenyl, $(C_2-C_3)$-alkynyl or $(C_1-C_6)$-alkoxy-$(C1-C4)$-alkyl;
$R^{16}$ and $R^{17}$ are each independently H, $(C_1-C_3)$-alkyl or $(C_1-C_3)$-haloalkyl; and
each heterocyclyl in the above-mentioned radicals is independently a heterocyclic radical having 3 to 6 ring atoms and 1, 2 or 3 hetero atoms in the ring selected from the group consisting of N, O and S.

5. The compound of claim 4, wherein $R^9$ is $CF_3$.
6. The compound of claim 3, wherein W is C-Cl, $R^4$ is Cl, and $R^5$ is $CF_3$.
7. The compound of claim 6, wherein
$R^1$ $CONR^6R^7$;
W is C-Cl;
$R^2$ is H or $S(O)_mR^9$;
$R^3$ is $NR^{10}R^{11}$, halogen, OH or $(C_1-C_3)$-alkoxy;
$R^4$ is Cl;
$R^5$ is CFhd 3;
$R^6$ is H, $(C_1-C_4)$-alkyl, $(C_1-C_3)$-alkoxy-$(C_1-C_2)$-alkyl, $(C_3-C_4)$-alkenyl, $(C_3-C_4)$-alkynyl, $(C_3-C_6)$-cycloalkyl, $(C_3-C_6)$-cycloalkyl-$(C_1-C_2)$-alkyl, $(C_1-C_3)$-alkoxy, $(C_1-C_3)$-alkylthio, $(CH_2)_nR^{12}$ or $(CH_2)_pR^{13}$;
$R^7$ is H, $(C_1-C_3)$-alkyl, $(C_3-C_4)$-alkenyl or $(C_3-C_4)$-alkynyl;
$R^9$ is methyl, ethyl or $CF_3$;

$R^{10}$ and $R^{11}$ are each independently H, $(C_1$-$C_3)$-alkyl, $(C_1$-$C_3)$-haloalkyl, $(C_3$-$C_4)$-alkenyl, $(C_3$-$C_4)$-haloalkenyl, $(C_3$-$C_4)$-alkynyl, $(C_3$-$C_6)$-cycloalkyl, $(C_3$-$C_6)$-cycloalkyl-$(C_1$-$C_3)$-alkyl, $COR^{14}$ or $CO_2R^{15}$; or $R^{12}$ is phenyl unsubstituted or substituted by one or more radicals selected from the group consisting of halogen, $(C_1$-$C_3)$-alkyl, $(C_1$-$C_3)$-haloalkyl, $(C_1$-$C_3)$-alkoxy, $CO_2R^6$, CN and $NO_2$;

$R^{13}$ is heterocyclyl unsubstituted or substituted by one or more radicals selected from the group consisting of halogen, $(C_1$-$C_3)$-alkyl, $(C_1$-$C_3)$-haloalkyl, $(C_1$-$C_3)$-alkoxy, $(C_1$-$C_3)$-haloalkoxy, $NO_2$, CN, $CO_2R^{16}$, $S(O)_qR^9$, OH and oxo;

$R^{14}$ and $R^{15}$ are each independently $(C_1$-$C_3)$-alkyl;

$R^{16}$ and $R^{17}$ are each independently H or $(C_1$-$C_3)$-alkyl; and each heterocyclyl in the above-mentioned radicals is independently a heterocyclic radical having 3 to 6 ring atoms and 1, 2 or 3 hetero atoms in the ring selected from the group consisting of N, O and S.

8. The compound of claim 6, wherein
$R^1$ is $CONR^6R^7$;
$R^2$ is H or $S(O)_mR^9$;
$R^3$ is $NR^{10}$;
$R^6$ is H, $(C_1$-$C_5)$-alkyl, $(C_1$-$C_2)$-alkoxy-$(C_1$-$C_2)$-alkyl, $(C_3$-$C_4)$-alkenyl, $(C_3$-$C_4)$-alkynyl, $(C_3$-$C_6)$-cycloalkyl, $(C_3$-$C_6)$-cycloalkyl-$(C_1$-$C_2)$-alkyl, furfuryl or tetrahydrofurfuryl;
$R^7$ is H or $(C_1$-$C_3)$-alkyl;
$R^9$ is methyl, ethyl or $CF_3$; and
$R^{10}$ is H, methyl or ethyl.

9. The compound of claim 6, wherein
$R^1$ is $CO_2R^8$,
$R^2$ is H, or $S(O)_mR^9$;
$R^3$ is $NR^{10}R^{11}$;
$R^8$ is H, methyl or ethyl;
$R^9$ is methyl, ethyl or $CF_3$;
$R^{10}$ H, methyl or ethyl; and
$R^{11}$ is H.

10. The compound of claim 6, wherein
$R^1$ is $CONR^6R^7$;
$R^2$ is $S(O)_mCF_3$;
$R^3$ is $NR^{10}R^{11}$, halogen, OH or $(C_1$-$C_2)$-alkyl;
$R^6$ is H or $(C_1$-$C_3)$-alkylthio;
$R^7$ is H;
$R^{10}$ is $(C_1$-$C_3)$-alkyl, $COR^{14}$ or $CO_2R^{15}$;
$R^{11}$, $R^{14}$ and $R^{15}$ are each independently $(C_1$-$C_3)$-alkyl.

11. A method for growth regulation in field crop plants, which comprises applying to the site where the action is desired an effective amount of a compound of claim 1 or an agriculturally acceptable salt thereof.

12. The method of claim 11, wherein said site is selected from the group consisting of plants, seeds, and a loci from which said plants and seeds grow.

13. The method of claim 11, wherein said effective amount is a non- phytotoxic amount.

14. The method of claim 13 that results in a yield increase of at least 10% concerning the plants to which it is applied.

15. The method of claim 11, wherein
$R^1$ is $CONR^6R^7$;
W is C—Cl or C—Br;
$R^2$ $S(O)_mR^9$;
$R^3$ is $NR^{10}R^{11}$, halogen, OH, $(C_1$-$C_3)$-alkoxy, $(C_2$-$C_6)$-alkenyloxy or $(C_2$-$C_6)$-alkynyloxy;
$R^4$ is Cl or Br;
$R^5$ is $CF_3$ or $OCF_3$;

$R^6$ is H, $(C_1$-$C_4)$-alkyl, $(C_1$-$C_4)$-haloalkyl, $(C_1$-$C_3)$-alkoxy-$(C_1$-$C_3)$-alkyl, $(C_3$-$C_4)$-alkenyl, $(C_3$-$C_4)$-haloalkenyl, $(C_3$-$C_4)$-alkynyl, $(C_3$-$C_4)$-haloalkynyl, $(C_3$-$C_6)$-cycloalkyl, $(C_3$-$C_6)$-cycloalkyl-$(C_1$-$C_3)$-alkyl, $(C_1$-$C_3)$-alkoxy, $(C_1$-$C_3)$-alkylthio, $(CH_2)_nR^{12}$ or $(CH_2)_pR^{13}$;

$R^7$ is H, $(C_1$-$C_4)$-alkyl, $(C_3$-$C_4)$-alkenyl or $(C_3$-$C_4)$-alkynyl; or $R^6$ and $R^7$ together with the attached N atom form a five- or six-membered saturated ring which optionally contains an additional hetero atom in the ring which is selected from O, S and N, the ring being unsubstituted or substituted by one or more radicals selected from the group consisting of halogen, $(C_1$-$C_3)$-alkyl and $(C_1$-$C_3)$-haloalkyl;

$R^9$ is $(C_1$-$C_3)$-alkyl or $(C_1$-$C_3)$-haloalkyl;

$R_{10}$ and $R_{11}$ are each independently H, (Chd 1-$C_3$)-alkyl, (Chd 1-$C_3$)-haloalkyl, $(C_3$-$C_4)$-alkenyl, $(C_3$-$C_4)$-haloalkenyl, $(C_3$-$C_4)$-alkynyl, $(C_3$-$C_6)$-cycloalkyl, $(C_3$-$C_6)$-cycloalkyl-$(C_1$-$C_3)$-alkyl, $COR^{14}$ or $CO_2R^{15}$; or $R^{10}$ and $R^{11}$ together with the attached N atom form a five- or six-membered saturated ring which optionally contains an additional hetero atom in the ring which is selected from O, S and N; the ring being unsubstituted or substituted by one or more radicals selected from the group consisting of halogen, $(C_1$-$C_3)$-alkyl and $(C_1$-$C_3)$-haloalkyl;

$R^{12}$ is phenyl unsubstituted or substituted by one or more radicals selected from the group consisting of halogen, $(C_1$-$C_3)$-alkyl, $(C_1$-$C_3)$-haloalkyl, $(C_1$-$C_3)$-alkoxy, $(C_1$-$C_3)$-haloalkoxy, $CO_2R^{16}$, CN, $NO_2$, $S(O)_qR^9$, $COR^{16}$, $CONR^{16}R^{17}$, $NR^{16}R^{17}$ and OH;

$R^{13}$ is heterocyclyl unsubstituted or substituted by one or more radicals selected from the group consisting of halogen, $(C_1$-$C_3)$-alkyl, (Chd 1-$C_3$)-haloalkyl, $(C_1$-$C_3)$-alkoxy, $(C_1$-$C_3)$-haloalkoxy, $NO_2$, CN, $CO_2R^{16}$, $S(O)_qR^9$, OH and oxo;

$R^{14}$ and $R^{15}$ are each independently H, $(C_1$-$C_3)$-alkyl, $(C_1$-$C_3)$-haloalkyl, $(C_2$-$C_3)$-alkenyl, $(C_2$-$C_3)$-haloalkenyl, $(C_2$-$C_3)$-alkynyl or $(C_1$-$C_6)$-alkoxy-$(C_1$-$C_4)$-alkyl;

$R^{16}$ and $R^{17}$ are each independently H, $(C_1$-$C_3)$-alkyl or $(C_1$-$C_3)$-haloalkyl; and each heterocyclyl in the above-mentioned radicals is independently a heterocyclic radical having 3 to 6 ring atoms and 1, 2 or 3 hetero atoms in the ring selected from the group consisting of N, O and S.

16. The method of claim 11, wherein
$R^1$ is $CONR^6R^7$;
W is C—Cl;
$R^2$ is H, or $S(O)_mR^9$;
$R^3$ is $NR^{10}R^{11}$, halogen, OH or $(C_1$-$C_3)$-alkoxy;
$R^4$ is Cl;
$R^5$ is $CF_3$;
$R^6$ is H, $(C_1$-$C_4)$-alkyl, $(C_1$-$C_3)$-alkoxy-$(C_1$-$C_2)$-alkyl, $(C_3$-$C_4)$-alkenyl, $(C_3$-$C_4)$-alkynyl, $(C_3$-$C_6)$-cycloalkyl, $(C_3$-$C_6)$-cycloalkyl-$(C_1$-$C_2)$-alkyl, $(C_1$-$C_3)$-alkoxy, $(C_1$-$C_3)$-alkylthio, $(CH_2)_nR^{12}$ or $(CH_2)_pR^{13}$;

$R^7$ is H, $(C_1$-$C_3)$-alkyl, $(C_3$-$C_4)$-alkenyl or $(C_3$-$C_4)$-alkynyl;

$R^9$ is methyl, ethyl or $CF_3$;

$R10$ and $R^{11}$ are each independently H, $(C_1$-$C_3)$-alkyl, $(C_1$-$C_3)$-haloalkyl, $(C_3$-$C_4)$-alkenyl, $(C_3$-$C_4)$-haloalkenyl, $(C_3$-$C_4)$-alkynyl, $(C_3$-$C_6)$-cycloalkyl, $(C_3$-$C_6)$-cycloalkyl-$(C_1$-$C_3)$-alkyl, $COR^{14}$ or $CO_2R^{15}$; or $R^{12}$ is phenyl unsubstituted or substituted by one or more radicals selected from the group consisting of halogen, $(C_1$-$C_3)$-alkyl, $(C_1$-$C_3)$-haloalkyl, (Chd 1-$C_3$)-alkoxy, $CO_2R^{16}$, CN and $NO_2$;

$R^{13}$ is heterocyclyl unsubstituted or substituted by one or more radicals selected from the group consisting of halogen, $(C_1-C_3)$-alkyl, $(Chd\ 1-C_3)$-haloalkyl, $(C_1-C_3)$-alkoxy, $(C_1-C_3)$-haloalkoxy, $NO_2$, $CN$, $CO_2R^{16}$, $S(O)_qR^9$, OH and oxo;

$R^{14}$ and $R^{15}$ are each independently $(C_1-C_3)$-alkyl;

$R^{16}$ and $R^{17}$ are each independently H or $(Chd\ 1-C_3)$-alkyl; and each heterocyclyl in the above-mentioned radicals is independently a heterocyclic radical having 3 to 6 ring atoms and 1, 2 or 3 hetero atoms in the ring selected from the group consisting of N, O and S.

17. The method of claim 11, in which
$R^1$ is $CONR^6R^7$;
W is C—Cl;
$R^2$ is H or $S(O)_mR^9$;
$R^3$ is $NHR^{10}$;
$R^4$ is Cl;
$R^5$ is $CF_3$;
$R^6$ is H, $(C_1-C_4)$-alkyl, $(C_1-C_2)$-alkoxy-$(C_1-C_2)$-alkyl, $(C_3-C_4)$-alkenyl, $(C_3-C_4)$-alkynyl, $(C_3-C_6)$-cycloalkyl, $(C_3-C_6)$-cycloalkyl-$(C_1-C_2)$-alkyl, furfuryl or tetrahydrofurfuryl;
$R^7$ is H or $(C_1-C_3)$-alkyl;
$R^9$ is methyl, ethyl or $CF_3$; and
$R^{10}$ is H, methyl or ethyl.

18. The method of claim 11, in which
$R^1$ is $CO_2R^8$,
W is C—Cl;
$R^2$ is H, or $S(O)_mR^9$;
$R^3$ is $NR^{10}R^{11}$;
$R^4$ is Cl;
$R^5$ is $CF_3$;
$R^8$ is H, methyl or ethyl;
$R^9$ is methyl, ethyl or $CF_3$;
$R^{10}$ is H, methyl or ethyl; and
$R^{11}$ is H.

19. The method of claim 11, in which
$R^1$ is $CONR^6R^7$;
W is C—Cl;
$R^2$ is $S(O)_mCF_3$;
$R^3$ is $NR^{10}R^{11}$, halogen, OH or $(C_1-C_2)$-alkyl;
$R^4$ is Cl;
$R^5$ is $CF_3$;
$R^6$ is H or $(C_1-C_3)$-alkylthio;
$R^7$ is H;
$R^{10}$ is $(C_1-C_3)$-alkyl, $COR^{14}$ or $CO_2R^{15}$;
$R^{11}$, $R^{14}$ and $R^{15}$ are each independently $(C_1-C_3)$-alkyl.

20. A composition for plant growth regulation, comprising one or more compounds of formula (I) as defined in claim 1 or an agriculturally acceptable salt thereof, and one or more carriers or surfactants, or mixtures thereof, useful for plant protection formulations.

21. The composition of claim 20, further comprising one or more active compounds selected from the group consisting of acaricides, fungicides, herbicides, insecticides, nematicides and plant growth regulating substances.

22. The method of claim 11, wherein the plant is a monocotyledoneous or dicotyledoneous crop plant.

23. The method of claim 11, wherein the plant is selected from the group consisting of wheat, barley, rye, triticale, rice, maize, sugar beet, cotton, and soybeans.

* * * * *